(12) United States Patent
Schunck et al.

(10) Patent No.: US 11,130,772 B2
(45) Date of Patent: Sep. 28, 2021

(54) CYP-EICOSANOID DERIVATIVES

(71) Applicants: MAX-DELBRUECK-CENTRUM FUER MOLEKULARE MEDIZIN, Berlin (DE); BOARD OF REGENTS, THE UNIVERSITY OF TEXAS SYSTEM, Austin, TX (US)

(72) Inventors: Wolf-Hagen Schunck, Berlin (DE); Dominik Mueller, Berlin (DE); Robert Fischer, Berlin (DE); Gerd Wallukat, Berlin (DE); Anne Konkel, Berlin (DE); John Russell Falck, Dallas, TX (US)

(73) Assignees: MAX-DELBRUECK-CENTRUM FUER MOLEKULARE MEDIZIN; BOARD OF REGENTS, THE UNIVERSITY OF TEXAS SYSTEM

( * ) Notice: Subject to any disclaimer, the term of this patent is extended or adjusted under 35 U.S.C. 154(b) by 0 days.

(21) Appl. No.: 15/113,139

(22) PCT Filed: Jan. 21, 2015

(86) PCT No.: PCT/EP2015/000105
§ 371 (c)(1),
(2) Date: Jul. 21, 2016

(87) PCT Pub. No.: WO2015/110262
PCT Pub. Date: Jul. 30, 2015

(65) Prior Publication Data
US 2017/0008918 A1  Jan. 12, 2017

Related U.S. Application Data

(60) Provisional application No. 61/930,031, filed on Jan. 22, 2014.

(51) Int. Cl.
| | | |
|---|---|---|
| C07F 9/38 | (2006.01) | |
| C07C 309/21 | (2006.01) | |
| C07C 311/51 | (2006.01) | |
| C07C 323/41 | (2006.01) | |
| C07D 277/82 | (2006.01) | |
| C07D 291/04 | (2006.01) | |
| C07F 9/40 | (2006.01) | |

(52) U.S. Cl.
CPC .......... *C07F 9/3826* (2013.01); *C07C 309/21* (2013.01); *C07C 311/51* (2013.01); *C07C 323/41* (2013.01); *C07D 277/82* (2013.01); *C07D 291/04* (2013.01); *C07F 9/3882* (2013.01); *C07F 9/4015* (2013.01)

(58) Field of Classification Search
CPC .... C07F 9/3826; C07F 9/3882; C07F 9/4015; C07C 309/21; C07C 311/51; C07C 323/41; C07D 277/82; C07D 291/04
USPC ....................................................... 514/119
See application file for complete search history.

(56) References Cited

U.S. PATENT DOCUMENTS

| | | |
|---|---|---|
| 5,753,702 A | 5/1998 | Bednar et al. |
| 8,658,632 B2 | 2/2014 | Brostrom et al. |
| 9,272,991 B2 | 3/2016 | Schunck et al. |
| 2002/0049244 A1 | 4/2002 | Roman et al. |
| 2002/0151734 A1 | 10/2002 | Schwartzman et al. |
| 2008/0095711 A1 | 4/2008 | Falck et al. |
| 2008/0146663 A1 | 6/2008 | Imig et al. |
| 2008/0306155 A1 | 12/2008 | Roman et al. |
| 2011/0059885 A1 | 3/2011 | Lea et al. |
| 2012/0122972 A1 | 5/2012 | Schunck et al. |

FOREIGN PATENT DOCUMENTS

| | | |
|---|---|---|
| CN | 102066412 A | 5/2011 |
| WO | 2004080389 A2 | 9/2004 |
| WO | 2005123079 A2 | 12/2005 |
| WO | 2012138706 A1 | 10/2012 |

OTHER PUBLICATIONS

Kubinyi (3D QSAR in Drug Design: Ligand-Protein Interactions and Molecular Similarity, vol. 2-3, Springer, 1998, 800 pages). pp. 243-244 provided.*
Falck et al. (J. Med. Chem. 2009, 52, 5069-5075).*
Jamieson et al. (Pharmacology & Therapeutics (2017).*
Wermuth, The Practice of Medicinal Chemsitry, 2d ed. (2003), 768 pages. Chs 9-10 provided.*
Lauterbach, B., et al., Cytochrorne P450-dependent eicosapentaenoic acid metabolites are novel BK channel activators, Hypertension, 2002, vol. 39, pp. 609-613.
Lavie, C.J., et al., Omega-3 polyunsaturated fatty acids and cardiovascular diseases, J Am Coll Cardiol, 2009, vol. 54, No. 7, pp. 585-594.
Leaf, A., et al., Clinical prevention of sudden cardiac death by n-3 polyunsaturated fatty acids and mechanism of prevention of arrhythmias by n-3 fish oils, 2003, vol. 107, No. 21, pp. 2646-2652.
Leaf, A., J. Nutr. Health Aging, 2001, vol. 5, pp. 173-178.
Leaf, Clifton, Health Administrator vol. XVII, No. 1: 172-183, 2005.
Li, Yunyuan et al., "Differential Effects of Various Eicosanoids on the Production or Prevention of Arrhythmias in Cultured Neonatal Rat Cardiac Myocytes", Prostagiandins, 1997, vol. 54, pp. 511-530.

(Continued)

*Primary Examiner* — Robert H Havlin
(74) *Attorney, Agent, or Firm* — Agris & Von Natzmer, LLP; Joyce Von Natzmer

(57) ABSTRACT

The present invention relates to compounds according to general formula (I) which are analogues of epoxymetabolites produced by cytochrome P450 (CYP) enzymes from omega-3 (n-3) polyunsaturated fatty acids (PUFAs). The present invention further relates to compositions containing one or more of these compounds and to the use of these compounds or compositions for the treatment or prevention of conditions and diseases associated with inflammation, proliferation, hypertension, coagulation, immune function, pathologic angiogenesis, heart failure and cardiac arrhythmias.

14 Claims, 1 Drawing Sheet

(56) References Cited

OTHER PUBLICATIONS

Lu, T., et al., Stereospecific activation of cardiac ATP-sensitive K(+) channels by epoxyelcosatrienoic acids: a structural determinant study, Mol Pharmacol, 2002, vol. 62, pp. 1076-1083.
Luft, F.C., et al., Hypertension-induced end-organ damage: A new transgenic approach to an old problem, Hypertension, 1999, vol. 33, pp. 212-218.
Luo et al., Cell, 2009, 136, pp. 823-837.
Marchioli, R., et al., Early protection against sudden death by n-3 polyunsaturated fatty acids after myocardial infarction: time-course analysis of the results of the Gruppo Italiano per lo Studio della Sopravvivenza nell'lnfarto Miocardio (GISSI)-Prevenzione, 2002, vol. 105, No. 16, pp. 1897-1903.
McLean, et al., Cardiovasc. Res., 2000, vol. 48, pp. 194-210.
Meddad-Belhabich, N., et al., Design of new potent and slective secretory phospholipase A2 inhibitors. 6-Synthesis, structure-activty relationships and molecular modeling of 1-substituted-4-[4,5-dihydri-1,2,4-(4H)-oxadiazol-5-one-3-yl(methyl)]-functionalized aryl piperazin/one/dione derivatives. Bioorg. Med. Chem., 2010, vol. 18, pp. 3588-3600.
Mori, T.A., Am. J. Clin. Nutr., 2000, vol. 71, pp. 1085-1094.
Morin, C., et al., 17, 18-epoxyeicosatetraenoic acid targets ppargamma and p38 mitogen-activated protein kinase to mediate its anti-inflammatory effects in the lung: Role of soluble epoxide hydrolase, Am J Respir Cell Mol Biol, 2010, vol. 43, pp. 564-575.
Mozaffarian, D., Fish and n-3 fatty acids for the prevention of fatal coronary heart disease and sudden cardiac death, Am J Clin Nutr, 2008, vol. 87, No. 6, pp. 1991S-1996S.
Muller, D.N., et al., A peroxisome proliferator-activated receptor-alpha activator induces renal CYP2C23 activity and protects from angiotensin II-induced renal injury, Am J Pathol, 2004, vol. 164, pp. 521-532.
Nithipatikom, K., et al., Inhibition of cytochrome P450omega-hydroxylase: a novel endogenous cardioprotective pathway, Circ Res, 2004, vol. 95, pp. e65-e71.
Nordoy, A., Lipids, 1999, vol. 34, pp. 19-22.
Oh, D.Y., et al., Cell, 2010, vol. 142, No. 5, pp. 687-698.
Panigrahy, D., et al., Epoxyeicosanoids stimulate multiorgan metastasis and tumor dormancy escape in mice, J Clin Invest, 2012, vol. 122, pp. 178-191.
Raidoo, et al., Immunopharrnacol, 1997, vol. 36, No. 2-3, pp. 153-160.
Rambjor, G.S., et al., Lipid 31, 1996, pp. 45-49.
Ricupero, et al., J. Biol, Chem., 2000, vol. 275, No. 17, pp. 12475-12480.
Roman, R.J., P-450 metabolites of arachidonic acid in the control of cardiovascular function, Physiol Rev, 2002, vol. 82, pp. 131-185.
Romanov, Stepan G. et al., "Total synthesis of (5Z,8Z,11Z,14Z)-18 and 19-oxoeicosa-5,8,11,14-tetraenoic acids", Tetrahedron, 2002, 58, pp. 8483-8487.
Romero, et al., J. Biol. Chem., 2005, vol. 15, pp. 14378-14384.
Salem, N., et al., Lipids, 2001, vol. 36, pp. 945-959.
Schwarz, D. et al., Human CYP1A1 variants lead to differential eicosapentaenoic acid metabolite patterns, Biochem Biophys Res Commun, 2005, vol. 336, pp. 779-783.
Schwarz, D., et al., Arachidonic and eicosapentaenoic acid metabolism by human CYP1A1: highly stereoselective formation of 17(R), 18(S)-epoxyeicosatetraenoic acid, Biochem Pharmacol, 2004, vol. 67, pp. 1445-1457.
Sellmayer, A., et al., Lipids, 1999, vol. 34, pp. 13-18.
Serini, S., et al., Dietary n-3 PUFA vascular targeting and the prevention of tumor growth and age-related macular degeneration, Curr Med Chem, 2009, vol. 16, No. 34, pp. 4511-4526.
Seubert, J., et al., Enhanced postischemic functional recovery in CYP2J2 transgenic hearts involves mitochondrial ATP-sensitive K+ channels and p42/p44 MAPK pathway, Circ Res, 2004, vol. 95, pp. 506-514.
Sharma, et al., Exp. Toxic. Pathol., 1994, vol. 46, pp. 421-433.

Sih, Charles J. et al., "General biochemical synthesis of oxygenated Prostaglandins E", Database CA [Online] Chemical Abstracts Service, Columbus, Ohio, US; STN Database accession No. 1969:427478, XP002578804.
Stadnicki, et al., Am. J. Physiol. Gastrointest Liver Physiol. 2005, vol. 289, No. 2, pp. G361-G366.
Storlien, L.H., et al., Curr. Opin. Clin. Nutr. Metab. Care 1, 1998, pp. 559-563.
Storlien, L.H., et al., Prostaglandins Leukotrienes Essent. Fatty Acids, 1997, vol. 57, pp. 379-385.
Theuer, J., et al., Inducible NOS inhibition, eicosapentaenoic acid supplementation, and angiotensin II-induced renal damage, Kiney Int, 2005, vol. 67, pp. 248-258.
Thiel, O. R., et al., J. Org. Chem., 2008, vol. 73, pp. 3508-3515.
Tiwari, K.P. et al., "Methyl 19-ketodocosanoate from Berberis acanthifolium" Database CA [Online] Chemical Abstracts Service, Columbus, Ohio, US; STN Database accession No. 1978:611923, XP002578653.
Tiwari, K.P. et al., "Methyl 19-ketotetracosanoate from Pavonia zeylanica Cav", Database CA [Onlinie] Chemical Abstracts Service, Columbus, Ohio, US; STN Database accession No. 1979:607389, XP002578651.
Toubiana, Raoul et al., "Long-chaim aliphatic substances related to bacterial lipids", Database CA [Online] Chemical Abstracts Service, Columbus, Ohio, US; STN Database accession No. 1963:408506, XP002578806.
Wallukat, G. et al., A. Biomed Biochim Acta. 1987, vol. 78, pp. 634-639—Abstract.
Wallukat, G., et al., J Clin Invest., 1999, vol. 103, pp. 945-952.
WebMD, Crohn's Disease Health Center, Crohn's Disease—Prevention, obtained from http://www.webmd.com/ibd-crohns-disease/crohns-disease/tc/crohns-disease-prevention on Apr. 5, 2015.
Weinbach, Susan P. et al., "Elucidation of Multilayer Growth of Amphiphiles on Liquid Surfaces", Database CA [Online] Chemical Abstracts Service, Columbus, Ohio, US; STN Database accession No. 1996:256414, XP002578655.
Westphal, C., et al., Cyp-eicosanoids—a new link between omega-3 fatty acids and cardiac disease? Prostaglandins Other Lipid Mediat, 2011, vol. 96, pp. 99-108.
Wong, A., et al., Lipid, Sugar and Liposaccharide Based Delivery Systems, Current Medicinal Chemistry 8, 2001, pp. 1123-1136.
Wu, Naiju et al., "Studies on Chemical constituents of Shi Mang Cao (Polygonum capitatum)", Database CA [Online] Chemical Abstracts Service, Columbus, Ohio, US; STN Database accession No. 1985:476116, XP002578656.
Xiao, Y.F., et al., Cytochrome P450: a novel system modulating Ca2+ channels and contraction in mammalian heart cells, J Physiol, 1998, vol. 508, pt. 3, pp. 777-792.
Yang, Wenqi et al., "Stable 5, 6-Epoxyeicosatrienoic Acid Analog Relaxes Coronary Arteries Through Potassium Channel Activation" in: Hypertension, 2005, No. 45, pp. 681-686.
Yi, Xiu-Yu et al., "Metabolism of adrenic acid to vasodilatory 1.alpha., 1.beta.-dihomo-epoxyeicosatrienoic acids by bovine coronary arteries" American Journal of Physiology, No. 292, 2007, pp. H2265-H2274.
Yonezawa et al. Biochmical Pharmacology 2005, 70, 453-460.
Yu, et al., Bioorganic & Medicinal Chemistry 2003, 11, 2803-2821.
Yu, Quanwei et al., "Lyotropic and Thermotropic Phase Transitions in Films of Ionene-Alkyl Sulfate Complexes" Database CA [Online], Chemical Abstracts Service, Columbus, Ohio, US; STN Database accession No. 2005:539357, XP002578650.
Zhang, G., et al., Epoxy metabolites of docosahexaenoic acid (dha) inhibit angiogenesis, tumor growth, and metastasis, Proc Natl Acad Sci USA, 2013, vol. 110, pp. 6530-6535.
Zhang, Yongde et al., "EET homologs potently dilate coronary microvessels and activate BKCa Channels", American Journal of Physiology, No. 280, 2001, pp. H2430-H2440.
J. Levisalles et al.:"A new catalytic system for the metathesis of functionalised olefins", Journal of Molecular Catalysis, vol. 26, No. 2, Sep. 1984, pp. 231-238, XP055179147.
J. R. Falck et al.:"17(R), 18(S)-Epoxyeicosatetraenoic acid, a potent eicosapentaenoic acid (EPA) derived regulator of cardiomyocyte

(56) References Cited

OTHER PUBLICATIONS contraction: structure-activity relationships and stable analogues", Journal of Medicinal Chemistry, vol. 54, No. 12, Jun. 23, 2011, pp. 4109-4118, XP055178684.
"Expert Scientific Group on Phase One Clinical Trials Final Report", Nov. 30, 2006, pp. C1, C35-C38.
Ali, M et al., "A hydroxyketone from the sedds of Musa balbisiana", Database CA [Online] Chemical Abstracts Service, Columbus, Ohio, US; 1992, STN Database accession No. 55570, XP002578647.
Aliev, E. E. et al., "Relation between the chain-length of tht hydrocarbon radical and the inhibitory efficiency or organci amide Compounds", Chemical Abstracts Service, Columbus, Ohio, US, STN Database accession No. 1976:596754, XP002578648.
Ames, D.E. et al., "Synthetic long-chain aliphatic Compounds. IX. Some antituberculous long-chain amines", Database CA [Online] Chemical Abstracts Service, Columbus, Ohio, US; STN Database accession No. 1953:6172, XP002578807.
Arm, J.P., et al., Clin. Sci., 1993, vol. 84, pp. 501-510.
Arnold, C., et al., Arachidonic acid-metabolizing cytochrome P450 enzymes are targets of {omega}-3 fatty acids, J Biol Chem, 2010, vol. 285, No. 43, pp. 32720-32733.
Ballatore, C., et al., Carboxylic Acid (Bio)Isosteres in Drup Design, ChemMedChem 8, 2013, pp. 385-395.
Barbosa-Sicard, E., et al., Eicosapentaenoic acid metabolism by cytochrome P450 enzymes of the CYP2C subfamily, Biochem Biophys Res Commun, 2005, vol. 329, pp. 1275-1281.
Boggs, J.M. et al., "Do the long fatty acid chains of sphimgolipids interdigitate across the center of a bilayer of shorter chain Symmetrie phopholipids?", Database CA [Online] Chemical Abstracts Service, Columbus, Ohio, US; STN Database accession No. 1994:157109, XP002578654.
Borbas, K. E., et al., A compact water-soluble porphyrin beraing an iodoacetamido bioconjugatable site, Org. Biomol. Chem., 2008, vol. 6, pp. 187-194.
Brechter, et al., Arthr. Rheum., 2007, vol. 56, No. 3, pp. 910-923.
Calder, P.C., Mol. Nutr. Food Res., 2012, vol. 56, pp. 1073-1080.
Calo, L., et al., N-3 fatty acids fro the prevention of atrial fibrillation after coronary artery bypass surgery: a randomized, controlled trial, J Am Coll Cardiol, 2005, vol. 45, No. 10, pp. 1723-1728.
CAS registry entry for Registry No. 83483-64-1, which entered STN on Nov. 16, 1984.
Casim, et al., Pharmacol. Ther., 2002, vol. 94, 1-34.
Connor, K.M., et al., Increased dietary intake of omega-3-polyunsaturated fatty acids reduces pathological retinal angiogenesis, Nat Med, 2007, vol. 13, No. 7, pp. 868-873.
Devani, et al., Am. J. Gastroenerol, 2002, vol. 97, No. 8, pp. 2026-2032.
Devani, et al., Dig. Liv, Disease, 2005, vol. 37, No. 9, pp. 665-673.
Dubois, R.N., et al., FASEB, 1998, vol. 12, pp. 1063-1073.
Duplus, E., et al., 2000, 275, pp. 30749-30752.
Durrani, Aziz A. et al., "Chemical examination of Scripus tuberosus. I" Database CA [Online], Chemical Abstracts Service, Columbus, Ohio, US, STN Database accession No. 1968:10218, XP002578649.
Dussault, Patrick et al., "A Chemoenzymic Approach to Hydroperoxyeicosatetraenoic Acids. Total Synthesis of 5 (S)-HPETE", J. Org. Chem., 1995, 60, pp. 218-226.
Ellingboe, J.W., et al., J.F. Antihyperglycemic activity of novel naphthalenylmethyl-3H-1,2,3,5-oxathiadiazole-2-oxides, J. Med. Chem., 1993, vol. 36, pp. 2485-2493—Abstract.
Falck, J.R. et al., "14, 15-Epoxyeicosa-5,8,11-trienoic Acid (14, 15-EET) Surrogates Containing Epoxide Bioisosteres: Influence upon Vascular Relaxation and Soluble Epoxide Hydrolase Inhibition", Journal of Medicinal Chemistry, 2009, 52(16), vol. 52, pp. 5069-5075.
Falck, J.R. et al., "Comparison of vasodilatory properties of 14, 15-EET analogs: structural requirements for dilation" in: Am J Physiol Heart Circ Physiol, No. 284, pp. H337-H349, 2003, (First published Sep. 19, 2002).

Fischer, R., et al., Angiotensin II-induced sudden arythmic death and electrical remodeling, Am J Physiol Heart Circ Physiol, 2007, vol. 293, pp. H1242-H1253.
Fischer, R., et al., Dietary n-3 polyunsaturated fatty acids and direct renin inhibition improve electrical remodeling in a model of high human renin hypertension, Hypertension, 2007, vol. 51, No. 2, pp. 540-546.
Goldstein, et al., J. Biol. Chem., 1984, vol. 259, No. 14, pp. 9263-9268.
Gross, E.R., et al., Cytochrome P450 omega-hydroxylase inhibition reduces infarct size during reperfusion via the sarcolemmal KATP channel, J Mol Cell Cardiol, 2004, vol. 37, pp. 1245-1249.
Gunstone et al., "Fatty acids. 35. Preparation and properties of the complete series of methyl epoxyoctadecanoates", Database CA [Online] Chemical Abstracts Service, Columbus, Ohio, US; STN Database accession No. 1972:548832, XP002539497.
Gupta, Jyoti et al., "Phytoconstituents of Capparis decidua root barks", Database CA [Online] Chemical Abstracts Service, Columbus, Ohio, US; STN Database accession No. 1998:810591, XP002578803.
Gupta, Madan et al., "Oxo fatty acids from Cryptocoryne sprialis rhizomes", Database CA [Online] Chemical Abstracts Service, Columbus, Ohio, US; STN Database accession No. 1985:42833, XP002578652.
Gura, Science Nov. 7, 1997: vol. 278. No. 5340, pp. 1041-1042.
Hamada, Y., et al., Bioorg. Med. Chem. Lett., 2008, vol. 18, pp. 1649-1653.
Harris, W.S., Am. J. Clin. Nutr. 65, 1997, pp. 1645-1654—Abstract.
Harris, W.S., et al., J. Lipid Res., 1997, vol. 38, pp. 503-515.
Hwang, D., Annu. Rev. Nutr., 2000, vol. 20, pp. 431-456.
Iyer, R.R. et al., "Convergent approaches to the syntheses of long-chain aliphatic hydroxy ketones: potential bioactive Compounds of plant origin", Database CA [Online] Chemical Abstracts Service, Columbus, Ohio, US; STN Database accession No. 1990:178456, XP002578657.
Jatoi et al., Critical Reviews in Oncology/Hematology 2005, 55, 37-43.
Jones, Derrick F. et al., "Misobiological oxidation of long-chain aliphatic Compounds. IV. Alkane derivatives having polar terminal groups", Database CA [Online] Chemical Abstracts Service, Columbus, Ohio, US; STN Database accession No. 1969:11049, XP002578805.
Jump, D.B., et al., Annu. Rev. Nutr., 1999, vol. 19, pp. 63-90.
Jump, D.B., J. Biol. Chem., 2002, vol. 277, pp. 8755-8758.
Jung, F., et al., Effect of cytochrome P450-dependent epoxyeicosanoids on Ristocetin-induced thrombocyte aggregation, Clin Hemorheol Microcirc, 2012, vol. 52, No. 2-4, pp. 403-416.
Kaergel, E., et al., P450-dependent arachidonic acid metabolism and angiotensin II-induced renal damage, Hypertension, 2002, vol. 40, pp. 273-279.
Kamb, Nature Reviews Drug Discovery 4, 161-165 (Feb. 2005).
Kang, J.X., et al., Effects of long-chain polyunsaturated fatty acids on the contraction of neonatal rat cardiac myocytes, Proc Natl Acad Sci USA, 1994, vol. 91, No. 21, pp. 9886-9890.
Kang, Jing X. et al., "Prevention of fatal cardiac arrhythmias by polyunsaturated fatty acids 1'2'3", The American Journal of Clinical Nutrition, 2000, vol. 71, No. 1, pp. 202S-207S.
Keenan, A.H., et al., Basal omega-3 fatty acid status affects fatty acid and oxylipin responses to high-dose n3-HUFA in healthy volunteers, J Lipid Res, 2012, vol. 53, No. 8, pp. 1662-1669.
Kris-Etherton, P.M., et al., Fish consumption, fish oil, omega-3 fatty acids, and cardiovascular disease, Circulation 2002, vol. 106, No. 21, pp. 2747-2757.
Larsson et al., Am. J. Clin. Nutr. 2004, 79, 935-45.
Communication issued in parallel application, EP15702370.6 dated May 8, 2018.
Liu et al., Stable EET urea agonist and soluble epoxide hydrolase inhibitor regulate rat pulmonary arteries through TRPCs, Hypertens Res. May 2011 ; 34(5): 630-639.
Office Action issued by the Indian Patent Office for Indian Patent Application 201647028105 dated Jun. 26, 2019 (bilingual).
Office Action issued by the Mexican Patent Office for Mexican Patent Application MX/a/2016/009507 dated Jun. 11, 2019 including summary by Mexican representative.

(56) References Cited

OTHER PUBLICATIONS

Office Action issued in Brazilian National Stage (BR11201601639-4) dated Jun. 2, 2020 (partial translation provided).
Office Action issued in Chinese National Stage application (CN201580005451.7) (dated May 17, 2018) including English translation.
Office Action issued in Chinese National Stage application (CN201580005451.7), citing CN1022348678A (see US20121222972, previously cited) and WO 2012138706A1 (previously cited) including English translation.

* cited by examiner

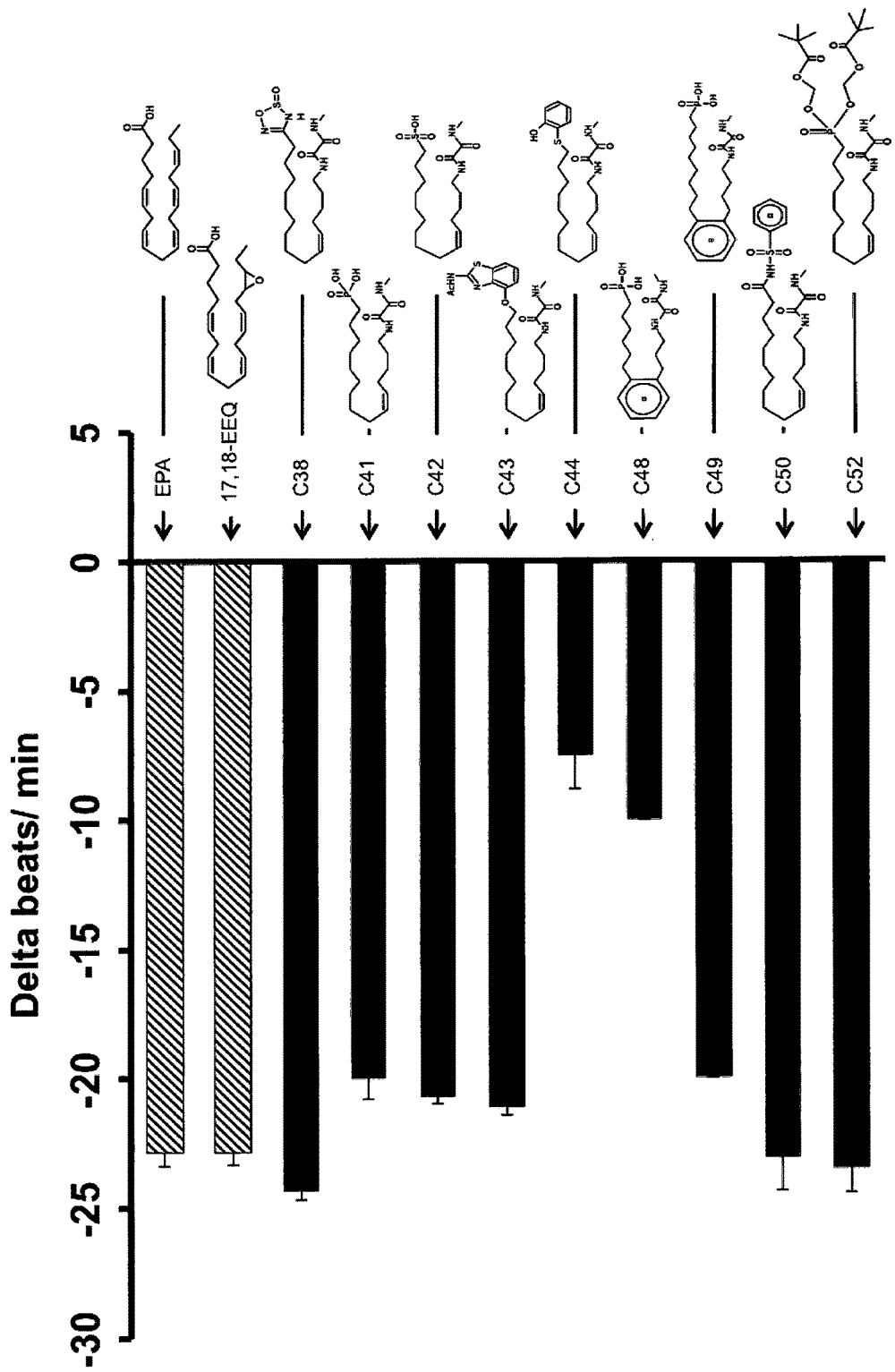

CYP-EICOSANOID DERIVATIVES

This is the U.S. national stage of International application PCT/EP2015/000105, filed Jan. 21, 2015, claiming the benefit of U.S. provisional application 61/930,031, filed Jan. 22, 2014.

STATEMENT REGARDING FEDERALLY SPONSORED RESEARCH OR DEVELOPMENT

This invention was made with government support under grant number GM031278 awarded by The National Institutes of Health. The government has certain rights in the invention.

The present invention relates to compounds according to general formula (I) which are analogues of epoxymetabolites produced by cytochrome P450 (CYP) enzymes from omega-3 (n-3) polyunsaturated fatty acids (PUFAs). The present invention further relates to compositions containing one or more of these compounds and to the use of these compounds or compositions for the treatment or prevention of a condition or disease associated with inflammation, proliferation, hypertension, coagulation, immune function, pathologic angiogenesis, heart failure and cardiac arrhythmias.

BACKGROUND

Omega-6 and omega-3 polyunsaturated fatty acids (n-6 and n-3 PUFAs) are essential components of the mammalian diet. Biologically most important n-3 PUFAs are eicosapentaenoic acid (EPA, 20:5 n-3) and docosahexaenoic acid (DHA, 22:6 n-3). Dietary n-3 PUFAs have effects on diverse physiological processes impacting normal health and chronic disease (for a review, see, for example, Jump, D. B. (2002) *J. Biol. Chem.* 277, 8755-8758), such as the regulation of plasma lipid levels (Rambjor, G. S., Walen, A. I., Windsor, S. L., and Harris, W. S. (1996) *Lipid* 31, 45-49; Harris, W. S. (1997) *Am. J. Clin. Nutr.* 65, 1645-1654; Harris, W. S., Hustvedt, B-E., Hagen, E., Green, M. H., Lu, G., and Drevon, C. A. (1997) *J. Lipid Res.* 38, 503-515; Mori, T. A., Burke, V., Puddey, I. B., Watts, G. F., O'Neal, D. N., Best, J. D., and Beilen, L. J. (2000) *Am. J. Clin. Nutr.* 71, 1085-1094), cardiovascular (Nordoy, A. (1999) *Lipids* 34, 19-22; Sellmayer, A., Hrboticky, N., and Weber, P. C. (1999) *Lipids* 34, 13-18; Leaf, A. (2001) *J. Nutr. Health Aging* 5, 173-178) and immune function (Hwang, D. (2000) *Annu. Rev. Nutr.* 20, 431-456), inflammation (Calder, P. C. (2012) *Mol. Nutr. Food Res.* 56, 1073-1080), insulin action (Storlien, L., Hulbert, A. J., and Else, P. L. (1998) *Curr. Opin. Clin. Nutr. Metab. Care* 1, 559-563; Storlien, L. H., Kriketos, A. D., Calvert, G. D., Baur, L. A., and Jenkins, A. B. (1997) *Prostaglandins Leukotrienes Essent. Fatty Acids* 57, 379-385 ; Oh, D. Y., Talukadar, S., Bae, E. J., Imamura, T., Morinaga, H., Fan, W., Li, P., Lu, W. J., Watkins, S. M., Olefsky, J. M. (2010) *Cell* 142 (5), 687-98), and neuronal development and visual function (Salem, N., Jr., Litman, B., Kim, H-Y., and Gawrisch, K. (2001) *Lipids* 36, 945-959). Ingestion of n-3 PUFA will lead to their distribution to virtually every cell in the body with effects on membrane composition and function, eicosanoid synthesis, and signaling as well as the regulation of gene expression (Salem, N., Jr., Litman, B., Kim, H-Y., and Gawrisch, K. (2001) *Lipids* 36, 945-959; Jump, D. B., and Clarke, S. D. (1999) *Annu. Rev. Nutr.* 19, 63-90; Duplus, E., Glorian, M., and Forest, C. (2000) 275, 30749-30752; Dubois, R. N., Abramson, S. B., Crofford, L., Gupta, R. A., Simon, L. S., Van De Putte, L. B. A., and Lipsky, P. E. (1998) *FASEB J.* 12, 1063-1073).

Epidemiological, clinical and experimental studies demonstrated that fish oil n-3 PUFAs (EPA and DHA) protect against cardiovascular disease (Kris-Etherton P M, Harris W S, Appel L J. Fish consumption, fish oil, omega-3 fatty acids, and cardiovascular disease. Circulation 2002;106(21):2747-57). n-3 PUFAs reduce the mortality from coronary heart disease and the rate of sudden cardiac death (Mozaffarian D. Fish and n-3 fatty acids for the prevention of fatal coronary heart disease and sudden cardiac death. Am J Clin Nutr 2008; 87(6):1991S-6S). Protection against ventricular arrhythmia is probably the main factor responsible for the prevention of sudden cardiac death by n-3 PUFAs after myocardial infarction and in heart failure patients (Leaf A, Kang J X, Xiao Y F, Billman G E. Clinical prevention of sudden cardiac death by n-3 polyunsaturated fatty acids and mechanism of prevention of arrhythmias by n-3 fish oils. Circulation 2003;107(21):2646-52 and Marchioli R, Barzi F, Bomba E, et al. Early protection against sudden death by n-3 polyunsaturated fatty acids after myocardial infarction: time-course analysis of the results of the Gruppo Italiano per lo Studio della Sopravvivenza nell'Infarto Miocardico (GISSI)-Prevenzione. Circulation 2002;105(16):1897-903). Significant antiarrhythmic effects of n-3 PUFAs were also observed in human studies on atrial fibrillation (Cato L, Bianconi L, Colivicchi F, et al. N-3 fatty acids for the prevention of atrial fibrillation after coronary artery bypass surgery: a randomized, controlled trial. J Am Coll Cardiol 2005; 45(10):1723-8). The potential cardiac benefits from n-3 PUFAs extend further to the prevention and treatment of congestive heart failure and atherosclerosis as well as to the reduction of general risk factors such as high plasma levels of triglycerides and pro-inflammatory cytokines (Lavie C J, Milani R V, Mehra M R, Ventura H O. Omega-3 polyunsaturated fatty acids and cardiovascular diseases. J Am Coll Cardiol 2009;54(7):585-94).

Additionally, epidemiological and experimental studies showed that n-3 PUFA consumption is associated with a reduced risk of macular degeneration and a lower incidence of colon, breast, prostate and other cancers (Serini S, Piccioni E, Calviello G. Dietary n-3 PUFA vascular targeting and the prevention of tumor growth and age-related macular degeneration. Curr Med Chem. 2009; 16(34):4511-26). A major common mechanism in protecting against macular degeneration and cancer consists in the capacity of n-3 PUFAs to inhibit pathological angiogenesis. EPA and DHA inhibit abnormal retinal neovascularization, vascular permeability, and inflammation (Connor K M, SanGiovanni J P, Lofqvist C, Aderman C M, Chen J, Higuchi A, Hong S, Pravda E A, Majchrzak S, Carper D, Hellstrom A, Kang J X, Chew E Y, Salem N Jr, Serhan C N, Smith L E. Increased dietary intake of omega-3-polyunsaturated fatty acids reduces pathological retinal angiogenesis. Nat Med. 2007 July;13(7):868-73). Angiogenesis is an essential step in tumor growth and metastasis that is promoted by n-6 PUFAs and n-6 PUFA-derived metabolites but inhibited by n-3 PUFAs and n-3 PUFA-derived metabolites (Kang J X, Liu A. The role of the tissue omega-6/omega-3 fatty acid ratio in regulating tumor angiogenesis. Cancer Metastasis Rev. 2013 June; 32(1-2):201-10).

Furthermore, one of the PUFAs most important biological roles is to supply precursors for the production of bioactive fatty acid metabolites that can modulate many functions (Arm, J. P., and Lee, T. H. (1993) Clin. Sci. 84: 501-510). For instance, arachidonic acid (AA; 20:4, n-6) is metabolized by Cytochrome P450 (CYP) enzymes to several classes of oxygenated metabolites with potent biological activities (Roman R J. P-450 metabolites of arachidonic acid in the control of cardiovascular function. *Physiol Rev.* 2002; 82:131-85). Major metabolites include 20-hydroxyeicosatetraenoic acid (20-HETE) and a series of regio- and stereoisomeric epoxyeicosatrienoic acids (EETs). CYP4A and CYP4F isoforms produce 20-HETE and CYP2C and CYP2J isoforms EETs.

It is known that EPA (20:5, n-3) and DHA (22:6, n-3) may serve as alternative substrates for AA-metabolizing CYP isoforms. CYP2C and CYP2J subfamily members that epoxidize AA to EETs, metabolize EPA to epoxyeicosatetraenoic acids (EEQs), and DHA to epoxydocosapentaenoic acids (EDPs). The ω-3 double bond distinguishing EPA and DHA from AA is the preferred site of attack by most of the epoxygenases resulting in the formation of 17,18-EEQ and 19,20-EDP as main metabolites. CYP4A and CYP4F isoforms, hydroxylating AA to 20-HETE, metabolize EPA to 20-hydroxyeicosapentaenoic acid (20-HEPE) and DHA to 22-hydroxydocosahexaenoic acid (22-HDHA). CYP1A1, CYP2E1 and other isoforms converting AA predominantly to 19-HETE show pronounced ω-3 epoxygenase activities with EPA and DHA (Theuer J, Shagdarsuren E, Muller D N, Kaergel E, Honeck H, Park J K, Fiebeler A, Dechend R, Haller H, Luft F C, Schunck W H. Inducible NOS inhibition, eicosapentaenoic acid supplementation, and angiotensin II-induced renal damage. *Kidney Int.* 2005; 67:248-58; Schwarz D, Kisselev P, Ericksen S S, Szklarz G D, Chernogolov A, Honeck H, Schunck W H, Roots I. Arachidonic and eicosapentaenoic acid metabolism by human CYP1A1: highly stereoselective formation of 17(R),18(S)-epoxyeicosatetraenoic acid. *Biochem Pharmacol.* 2004; 67:1445-57; Schwarz D, Kisselev P, Chernogolov A, Schunck W H, Roots I. Human CYP1A1 variants lead to differential eicosapentaenoic acid metabolite patterns. *Biochem Biophys Res Commun.* 2005; 336:779-83; Lauterbach B, Barbosa-Sicard E, Wang M H, Honeck H, Kargel E, Theuer J, Schwartzman M L, Haller H, Luft F C, Gollasch M, Schunck W H. Cytochrome P450-dependent eicosapentaenoic acid metabolites are novel BK channel activators. *Hypertension.* 2002;39:609-13; Barbosa-Sicard E, Markovic M, Honeck H, Christ B, Muller D N, Schunck W H. Eicosapentaenoic acid metabolism by cytochrome P450 enzymes of the CYP2C subfamily. *Biochem Biophys Res Commun.* 2005;329:1275-81). A remarkable feature of CYP-dependent n-3 PUFA metabolism is the preferred epoxidation of the n-3 double bond, which distinguishes EPA and DHA from AA. The resulting metabolites—17,18-EEQ from EPA and 19,20-EDP from DHA—are unique in having no homolog within the series of AA products. In line with the substrate specificity of the CYP isoforms, dietary EPA/DHA supplementation causes a profound shift from AA- to EPA- and DHA-derived epoxy- and ω-hydroxy-metabolites in all major organs and tissues of the rat and presumably also in human (Arnold C, Markovic M, Blossey K, Wallukat G, Fischer R, Dechend R, Konkel A, von Schacky C, Luft F C, Muller D N, Rothe M, Schunck W H. Arachidonic acid-metabolizing cytochrome P450 enzymes are targets of {omega}-3 fatty acids. J Biol Chem. 2010 October 22;285 (43):32720-33 and Keenan A H, Pedersen T L, Fillaus K, Larson M K, Shearer G C, Newman J W. Basal omega-3 fatty acid status affects fatty acid and oxylipin responses to high-dose n3-HUFA in healthy volunteers. J Lipid Res. 2012 August; 53(8):1662-9). EETs and 20-HETE play important roles in the regulation of various cardiovascular functions (Roman R J. P-450 metabolites of arachidonic acid in the control of cardiovascular function. *Physiol Rev.* 2002;82: 131-85). It has been shown that Ang II-induced hypertension is associated with a down-regulation of CYP-dependent AA metabolism (Kaergel E, Muller D N, Honeck H, Theuer J, Shagdarsuren E, Mullally A, Luft F C, Schunck W H. P450-dependent arachidonic acid metabolism and angiotensin II-induced renal damage. *Hypertension.* 2002;40:273-9) in a double-transgenic rat (dTGR) model of Ang II-induced hypertension and end-organ damage (Luft F C, Mervaala E, Muller D N, Gross V, Schmidt F, Park J K, Schmitz C, Lippoldt A, Breu V, Dechend R, Dragun D, Schneider W, Ganten D, Haller H. Hypertension-induced end-organ damage: A new transgenic approach to an old problem. *Hypertension.* 1999;33:212-8). The transgenic rats harbor the human renin and angiotensinogen genes, produce Ang II locally and develop significant hypertension, myocardial infarction and albuminuria. The animals die of myocardial and renal failure before the eighth week of age. The model shows severe features of Ang II-induced inflammation. Reactive oxygen species are generated, the transcription factors NF-κB and AP-1 are activated, and genes harboring binding sites for these transcription factors are activated.

Recently, it has been shown that eicosapentaenoic acid (EPA) supplementation significantly reduced the mortality of dTGR (Theuer J, Shagdarsuren E, Muller D N, Kaergel E, Honeck H, Park J K, Fiebeler A, Dechend R, Haller H, Luft F C, Schunck W H. Inducible NOS inhibition, eicosapentaenoic acid supplementation, and angiotensin II-induced renal damage. *Kidney Int.* 2005;67:248-58). Additionally, it has been shown that dTGR develop ventricular arrhythmias based on Ang II-induced electrical remodeling (Fischer R, Dechend R, Gapelyuk A, Shagdarsuren E, Gruner K, Gruner A, Gratze P, Qadri F, Wellner M, Fiebeler A, Dietz R, Luft F C, Muller D N, Schirdewan A. Angiotensin II-induced sudden arrhythmic death and electrical remodeling. Am J Physiol Heart Circ Physiol. 2007; 293:H1242-1253). Treatment of the dTGR rats with a PPAR-alpha activator strongly induced CYP2C23-dependent EET production and protected against hypertension and end-organ damage (Muller D N, Theuer J, Shagdarsuren E, Kaergel E, Honeck H, Park J K, Markovic M, Barbosa-Sicard E, Dechend R, Wellner M, Kirsch T, Fiebeler A, Rothe M, Haller H, Luft F C, Schunck W H. A peroxisome proliferator-activated receptor-alpha activator induces renal CYP2C23 activity and protects from angiotensin II-induced renal injury. Am J Pathol. 2004;164: 521-32).

Long-term feeding of dTGR (from week 4 to 7 of age) with a mixture of pure EPA- and DHA-ethyl esters (Omacor from Solvay Arzneimittel, Hannover, Germany) improved the electrical remodeling of the heart in this model of angiotensin II-induced hypertension. In particular, EPA and DHA reduced the mortality, suppressed the inducibility of cardiac arrhythmias and protected against connexin 43-gap junctional remodeling (Fischer R, Dechend R, Qadri F, Markovic M, Feldt S, Herse F, Park J K, Gapelyuk A, Schwarz I, Zacharzowsky U B, Plehm R, Safak E, Heuser A, Schirdewan A, Luft F C, Schunck W H, Muller D N. Dietary n-3 polyunsaturated fatty acids and direct renin inhibition improve electrical remodeling in a model of high human renin hypertension. Hypertension. 2008 February;51(2): 540-6). In general, CYP-dependent eicosanoids have to be considered as second messengers: EETs and 20-HETE are produced by CYP enzymes after extracellular signal induced release of AA from membrane phospholipids (by phospholipase A2) and exert their function in the context of signaling pathways modulating ion transport, cell proliferation and inflammation. Depending on the diet, n-3 PUFAs partially replace AA at the sn2-position of phospholipids and may thus become involved as alternative molecules in the subsequent signaling pathways.

The few studies on the biological activities of CYP-dependent eicosanoids in the heart indicate important roles for EETs and 20-HETE in the regulation of L-type $Ca^{2+}$ and sarcolemmal and mitochondrial ATP-sensitive potassium ($K_{ATP}$) channels. In cardiac myocytes, L-type $Ca^{2+}$ currents and cell shorting are reduced upon inhibition of EET generation and these effects can be reversed by adding 11,12-EET (Xiao Y F, Huang L, Morgan J P. Cytochrome P450: a novel system modulating Ca2+ channels and contraction in mammalian heart cells. *J Physiol.* 1998;508 (Pt 3):777-92). EETs were also shown to activate cardiac $K_{ATP}$ channels. This effect is highly stereoselective: only the S,R but not the R,S-enantiomer of 11,12-EET was effective (Lu T, VanRollins M, Lee H C. Stereospecific activation of cardiac ATP-sensitive K(+) channels by epoxyeicosatrienoic acids: a structural determinant study. *Mol Pharmacol.* 2002;62: 1076-83). Overexpression of the EET-generating human CYP2J2 resulted in an improved postischemic functional recovery of the transgenic mouse heart via activation of $K_{ATP}$ channels (Seubert J, Yang B, Bradbury J A, Graves J, Degraff L M, Gabel S, Gooch R, Foley J, Newman J, Mao L, Rockman H A, Hammock B D, Murphy E, Zeldin D C. Enhanced postischemic functional recovery in CYP2J2 transgenic hearts involves mitochondrial ATP-sensitive K+ channels and p42/p44 MAPK pathway. *Circ Res.* 2004;95: 506-14). 20-HETE appears to play an opposite role by acting as an endogenous $K_{ATP}$ channel blocker (Gross E R, Nithipatikom K, Hsu A K, Peart J N, Falck J R, Campbell W B, Gross G J. Cytochrome P450 omega-hydroxylase inhibition reduces infarct size during reperfusion via the sarcolemmal KATP channel. *J Mol Cell Cardiol.* 2004;37:1245-9; Nithipatikom K, Gross E R, Endsley M P, Moore J M, Isbell M A, Falck J R, Campbell W B, Gross G J. Inhibition of cytochrome P450omega-hydroxylase: a novel endogenous cardioprotective pathway. *Circ Res.* 2004;95:e65-71).

The currently known biological activities of EPA- and DHA-derived CYP metabolites partially resemble those of their AA-derived counterparts, appear in part unique or may even produce opposite effects (Westphal C, Konkel A, Schunck W H. Cyp-eicosanoids—a new link between omega-3 fatty acids and cardiac disease? *Prostaglandins Other Lipid Mediat.* 2011;96:99-108). The epoxy-metabolites of all three PUFAs share vasodilatory properties, whereby the potencies of EEQs and EDPs may exceed those of EETs in some vascular beds (Lauterbach B, Barbosa-Sicard E, Wang M H, Honeck H, Kargel E, Theuer J, Schwartzman M L, Haller H, Luft F C, Gollasch M, Schunck W H. Cytochrome P450-dependent eicosapentaenoic acid metabolites are novel BK channel activators. *Hypertension.* 2002;39:609-13). Anti-inflammatory effects were first revealed for 11,12- and 14,15-EET but are also exerted by EPA epoxides as exemplified by 17,18-EEQ (Morin C, Sirois M, Echave V, Albadine R, Rousseau E. 17,18-epoxyeicosatetraenoic acid targets ppargamma and p38 mitogen-activated protein kinase to mediate its anti-inflammatory effects in the lung: Role of soluble epoxide hydrolase. *Am J Respir Cell Mol Biol.* 2010;43:564-575). 17,18-EEQ and 19,20-EDP inhibit the $Ca^{2+}$—and isoproterenol-induced increased contractility of neonatal cardiomyocytes indicating that these metabolites may act as endogenous mediators of the antiarrhythmic effects of EPA and DHA described above (Arnold C, Markovic M, Blossey K, Wallukat G, Fischer R, Dechend R, Konkel A, von Schacky C, Luft F C, Muller D N, Rothe M, Schunck W H. Arachidonic acid-metabolizing cytochrome P450 enzymes are targets of {omega}-3 fatty acids. *J Biol Chem.* 2010 Oct. 22;285(43): 32720-33). Chemically synthesized compounds were recently described that share the antiarrhythmic properties of 17,18-EEQ in neonatal cardiomyocytes and reduce ventricular tachyarrhythmia in a rat model of myocardial infarction (Falck J R, Wallukat G, Puli N, Goli M, Arnold C, Konkel A, Rothe M, Fischer R, Müller D N, Schunck W H, 17(R),18(S)-epoxyeicosatetraenoic acid, a potent eicosapentaenoic acid (EPA) derived regulator of cardiomyocyte contraction: structure-activity relationships and stable analogues. *J Med Chem.* 2011 Jun. 23;54(12):4109-18; WO 2010/081683 A1, also published as US Pat. Pub. 2012/ 0122972, which is incorporated herein by reference in its entirety as are all other patent and non-patent publications referenced herein). The formation of 17,18-EEQ and 19,20-EDP may additionally contribute to the anti-thrombotic effects of n-3 PUFAs (Jung F, Schulz C, Blaschke F, Muller D N, Mrowietz C, Franke R P, Lendlein A, Schunck W H. Effect of cytochrome P450-dependent epoxyeicosanoids on Ristocetin-induced thrombocyte aggregation. *Clin Hemorheol Microcirc.* 2012;52(2-4):403-16). Moreover, there is evidence for an important role of CYP-dependent epoxymetabolites in mediating the opposite effects of n-6 and n-3 PUFAs in the processes of pathological angiogenesis described above. Thus, AA derived EETs promote tumor angiogenesis and metastasis (Panigrahy D, Edin M L, Lee C R, Huang S, Bielenberg D R, Butterfield C E, Barnes C M, Mammoto A, Mammoto T, Luria A, Benny O, Chaponis D M, Dudley A C, Greene E R, Vergilio J A, Pietramaggiori G, Scherer-Pietramaggiori S S, Short S M, Seth M, Lih F B, Tomer K B, Yang J, Schwendener R A, Hammock B D, Falck J R, Manthati V L, Ingber D E, Kaipainen A, D'Amore P A, Kieran M W, Zeldin D C. Epoxyeicosanoids stimulate multiorgan metastasis and tumor dormancy escape in mice. *J Clin Invest.* 2012;122:178-191). In contrast, 19,20-EDP and other regioisomeric DHA-epoxides inhibit these crucial events in cancerogenesis (Zhang G, Panigrahy D, Mahakian L M, Yang J, Liu J Y, Stephen Lee K S, Wettersten H I, Ulu A, Hu X, Tam S, Hwang S H, Ingham E S, Kieran M W, Weiss R H, Ferrara K W, Hammock B D. Epoxy metabolites of docosahexaenoic acid (dha) inhibit angiogenesis, tumor growth, and metastasis. *Proc Natl Acad Sci USA.* 2013;110: 6530-6535).

Although n-3 PUFA-derived CYP metabolites, such as 17,18-EEQ and 19,20-EDP, play important roles in mediating the beneficial effects of n-3 PUFAs in the mammalian body, they are not used as therapeutics due to their limited bioavailability as well as chemical and metabolic instability. These epoxymetabolites of n-3 PUFAs are prone to autoxidation, rapid inactivation by the soluble epoxide hydrolase, and degradation by β-oxidation. Finally, new agents for the treatment or prevention of conditions and diseases associated with inflammation, proliferation, pathological angiogenesis, hypertension, coagulation, immune function, heart failure and cardiac arrhythmias are of considerable interest as these conditions account for a significant number of death in patients and administration of many of the presently employed drugs is associated with complex drug interactions and many adverse side effects.

Therefore, the problem underlying the present invention is to provide new analogues of n-3 PUFA metabolites, which are more stable against deactivation by soluble epoxide hydrolase and/or are less prone to auto-oxidation, and which have anti-inflammatory, anti-proliferative, anti-hypertension, anti-coagulation, anti-angiogenic or immune-modulat-

SUMMARY OF THE INVENTION

The present invention relates to a compound of the general formula (I):

P-E-I    (I)

or a pharmaceutically acceptable salt thereof,
wherein
P is a group represented by the general formula (II):

—(CH$_2$)$_n$—B—(CH$_2$)$_k$—X    (II)

wherein
B represents a carbon-carbon bond; —O—; or —S—;
n is 0 or an integer of from 3 to 8; and
k is 0 or 1; provided that when n is 0 k is 1;
X represents a group:

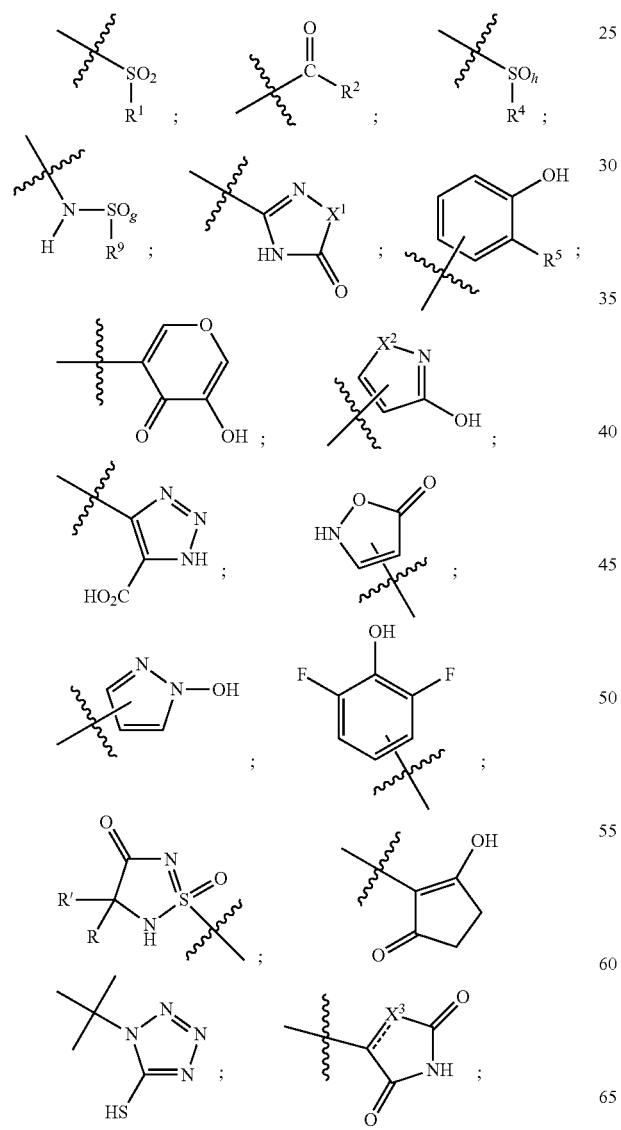

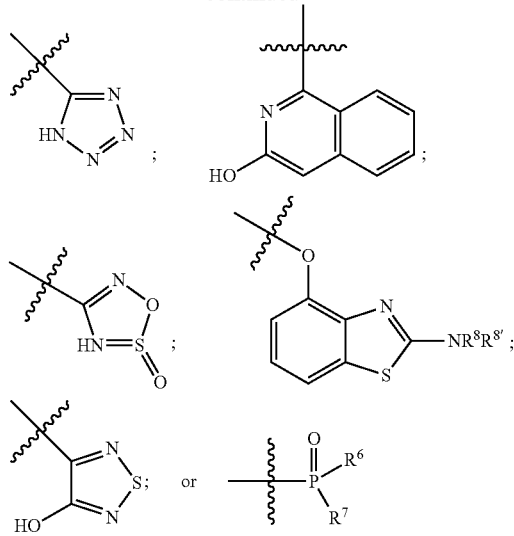

wherein
R and R' each independently represents a hydrogen atom; or a C$_1$-C$_6$alkyl group which may be substituted with one or more fluorine or chlorine atom(s) or hydroxyl group(s);

R$^1$ represents a hydroxyl group, C$_1$-C$_6$alkoxy, —NHCN, —NH(C$_1$-C$_6$alkyl), —NH(C$_3$-C$_6$cycloalkyl), —NH(aryl), or —O(C$_1$-C$_6$alkyldiyl)O(C=O)R$^{11}$; R$^{11}$ is a C$_1$-C$_6$alkyl group which is optionally substituted with one or more fluorine or chlorine atom(s); or a C$_3$-C$_6$cycloalkyl group which is optionally substituted with one or more fluorine or chlorine atom(s) or hydroxyl group(s);

R$^2$ represents —NHR$^3$; —NR$^{20}$R$^{21}$; —OR$^{22}$; —(OCH$_2$—CH$_2$)$_i$—R$^{23}$; —Xaa$_o$; a mono-, or disaccharide, or a derivative thereof, which is joined to —C(O) by an ester bond via the 1-O-, 3-O-, or 6-O-position of the saccharide;

or is selected from the group consisting of:

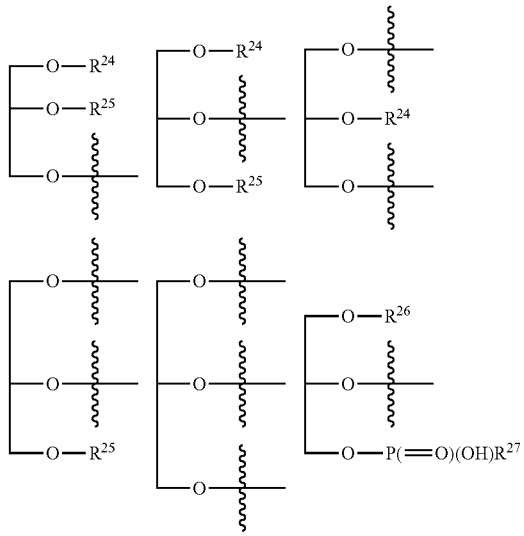

-continued

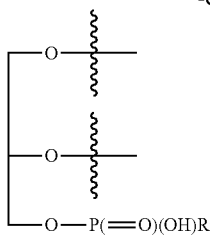

wherein
R³ represents (SO₂R³⁰); (OR³¹); —C₁-C₆alkanediyl (SO₂R³²); or —C₁-C₆alkanediyl(CO₂H);
R³⁰ is a C₁-C₆alkyl, or an aryl group, wherein the C₁-C₆alkyl group is optionally substituted with —NH₂, —NH(C₁-C₆)alkyl, —N(C₁-C₆)dialkyl, C₁-C₆alkyl-carbonyloxy-, C₁-C₆alkoxycarbonyloxy-, C₁-C₆alkyl-carbonylthio-, C₁-C₆alkylaminocarbonyl-, di(C₁-C₆)alkylaminocarbonyl-, one, two or three fluorine or chlorine atoms, or a hydroxyl group; and wherein the aryl group is optionally substituted with one, two or three substituents independently selected from the group consisting of C₁-C₆alkyl, C₁-C₆alkoxy, C₁-C₆alkylthio, fluorine or chlorine atom, hydroxyl group, amino group, —NH(C₁-C₆alkyl), and —N(C₁-C₆)dialkyl;
R³¹ is a C₁-C₆alkyl group which is optionally substituted with one or more fluorine or chlorine atom(s) or hydroxyl group(s); or a C₃-C₆cycloalkyl group which is optionally substituted with one or more fluorine or chlorine atom(s) or hydroxyl group(s);
R³² is a C₁-C₆alkyl group which is optionally substituted with one or more fluorine or chlorine atom(s) or hydroxyl group(s); or a C₃-C₆cycloalkyl group which is optionally substituted with one or more fluorine or chlorine atom(s) or hydroxyl group(s); R²⁰ and R²¹ each independently represents a hydrogen atom; a C₁-C₆alkyl group which may be substituted with one or more fluorine or chlorine atom(s) or hydroxyl group(s); a C₃-C₆cycloalkyl group which may be substituted with one or more fluorine or chlorine atom(s) or hydroxyl group(s); or —C₁-C₆alkyldiyl(CO₂H);
R²² is a hydrogen atom, a C₁-C₆alkyl group; or a C₃-C₆cycloalkyl group; wherein the C₁-C₆alkyl group or the C₃-C₆cycloalkyl group is optionally substituted with —NH2, —NH(C₁-C₆)alkyl, —N(C₁-C₆)dialkyl, —NH(C₁-C₆)alkyldiyl-C₁-C₆alkoxy, one, two or three fluorine or chlorine atom(s), hydroxy, or C₁-C₆alkoxy;
R²³ is —OH, —O(C₁-C₃)alkyl, or —N(C₁-C₃)dialkyl; i is an integer of from 1 to 10; R²⁴ R²⁵, and R²⁶ each independently represents a hydrogen atom; —C(=O)C₁₁-C₂₁alkyl; or —C(=O)C₁₁-C₂₁alkenyl;
R²⁷ represents —OH; —O(CH₂)₂NH₂, —OCH₂—[CH(NH₂)(CO₂H)], —O(CH₂)₂N(CH₃)₃; or

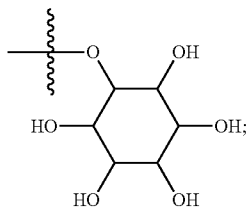 [SMILES: *OC1C(O)C(O)C(O)C(O)C1O]

Xaa represents Gly, a conventional D,L-, D- or L-amino acid, a non-conventional D,L-, D- or L-amino acid, or a 2- to 10-mer peptide; and is joined to —C(O) by an amide bond; o is an integer of from 1 to 10;
R⁴ represents

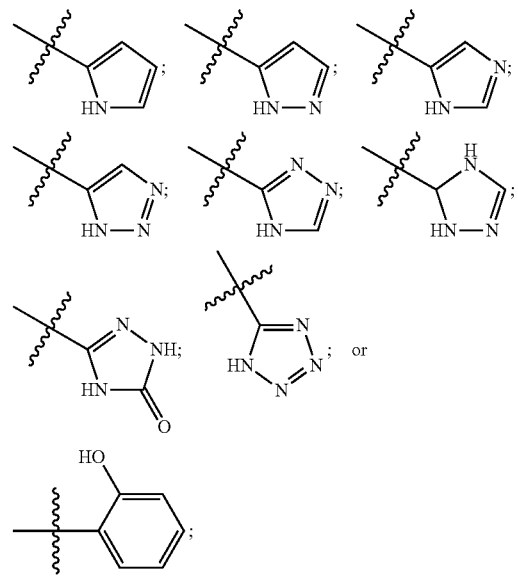

h is 0, 1, or 2;
R⁵ represents a hydrogen atom; a fluorine or chlorine atom; —CF₃; —C(=O)OR⁵¹; —NHC(=O)R⁵²; —C(=O)NR⁵³R⁵⁴; or —S(O₂)OH;
R⁵¹ represents a hydrogen atom; a C₁-C₆alkyl group; or a C₃-C₆cycloalkyl group; wherein the C₁-C₆alkyl group or the C₃-C₆cycloalkyl group is optionally substituted with —NH2, —NH(C₁-C₆)alkyl, —N(C₁-C₆)dialkyl, —NH(C₁-C₆)alkyldiyl-C₁-C₆alkoxy, one, two or three fluorine or chlorine atom(s), hydroxy, or C₁-C₆alkoxy;
R⁵², R⁵³ and R⁵⁴ each independently represents a C₁-C₆alkyl group which is optionally substituted with one or more fluorine or chlorine atom(s); a C₃-C₆cycloalkyl group which is optionally substituted with one or more fluorine or chlorine atom(s); or an aryl group which is optionally substituted with one, two or three substituents independently selected from the group consisting of C₁-C₆alkyl, C₁-C₆haloalkyl, C₁-C₆alkoxy, C₁-C₆alkylthio, fluorine or chlorine atom, hydroxyl group, amino group, —NH(C₁-C₆alkyl), —N(C₁-C₆)dialkyl, and an oxo substituent;
R⁶ and R⁷ each independently represents a hydroxyl group; an —O(C₁-C₆)alkyl group, an —O(C₂-C₆)alkenyl group, a, —O(C₁-C₆)alkyldiylO(C=O)(C₁-C₆) alkyl group, or a —O(C₁-C₆)alkyldiylO(C=O)(C₂-C₆) alkenyl group; wherein the C₁-C₆alkyl group and the C₂-C₆alkenyl group may be substituted with NH₂, —NH(C₁-C₆)alkyl, —N(C₁-C₆)dialkyl, C₁-C₆alkylcarbonyloxy-, C₁-C₆alkoxycarbonyloxy-, C₁-C₆alkylcarbonylthio-, C₁-C₆ alkylaminocarbonyl-, di(C₁-C₆)alkylaminocarbonyl-, or one, two or three fluorine or chlorine atom(s); or R⁶ represents a hydroxyl group and R⁷ represents a group:

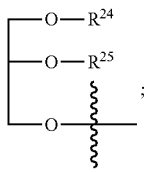

R⁸ and R⁸' each independently represents a hydrogen atom; a $C_1$-$C_6$alkyl group; —C(=O)$C_1$-$C_6$alkyl; —C(=O)$C_3$-$C_6$cycloalkyl; —C(=O)aryl; or —C(=O)heteroaryl; wherein the $C_1$-$C_6$alkyl, the $C_3$-$C_6$cycloalkyl, the aryl, or the heteroaryl group may be substituted with one, two or three substituents selected from the group consisting of fluorine or chlorine atom, hydroxy, —$NH_2$, —NH($C_1$-$C_6$)alkyl, —N($C_1$-$C_6$)dialkyl, —NH($C_1$-$C_6$)alkanediyl-$C_1$-$C_6$alkoxy, and $C_1$-$C_6$alkoxy;

$R^9$ represents $C_1$-$C_6$alkyl, or aryl; wherein the $C_1$-$C_6$alkyl is optionally substituted with —NH2, —NH($C_1$-$C_6$)alkyl, —N($C_1$-$C_6$)dialkyl, —NH($C_1$-$C_6$)alkyldiyl-$C_1$-$C_6$alkoxy, one, two or three fluorine or chlorine atom(s), hydroxy, $C_1$-$C_6$alkoxy, aryl, aryloxy, —C(=O)-aryl, —C(=O)$C_1$-$C_6$alkoxy; and wherein the aryl group is optionally substituted with one, two or three substituents independently selected from the group consisting of $C_1$-$C_6$alkyl, $C_1$-$C_6$alkoxy, $C_1$-$C_6$alkylthio, fluorine or chlorine atom, hydroxyl group, amino group, —NH($C_1$-$C_8$alkyl), —N($C_1$-$C_6$) dialkyl, and an oxo substituent;

g is 1 or 2;

$X^1$ represents an oxygen atom; sulfur atom; or NH;

$X^2$ represents an oxygen atom; sulfur atom; NH; or N($CH_3$);

$X^3$ represents an oxygen atom; sulfur atom; nitrogen atom; carbon atom; or C—OH; and the dashed line represents a carbon-carbon bond or a carbon-carbon double bond;

E is a group represented by the general formula (III) or (IV):

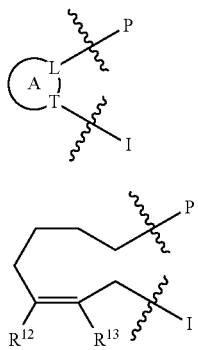

wherein ring A represents a 5-membered or 6-membered carbocyclic or heterocyclic ring containing at least one double bond; and L and T each independently represents a ring atom, wherein L and T are adjacent to another;

$R^{12}$ and $R^{13}$ each independently represents a hydrogen atom, a fluorine atom, hydroxy, —NH2, $C_1$-$C_6$alkyl, $C_1$-$C_6$alkoxy, —C(=O)-aryl, —C(=O)$C_1$-$C_6$alkyl, or —$SO_2$($C_1$-$C_6$alkyl); or —$SO_2$aryl; wherein any of the foregoing $C_1$-$C_6$alkyl, $C_1$-$C_6$alkoxy, or aryl are optionally substituted with one, two or three substituents independently selected from the group consisting of —$NH_2$, —NH($C_1$-$C_6$)alkyl, —N($C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, fluorine or chlorine atom, and hydroxy; or $R^{12}$ and $R^{13}$ are taken together to form a 5-membered or 6-membered ring, which ring is optionally substituted with one, two or three substituents independently selected from the group consisting of —$NH_2$, —NH($C_1$-$C_6$)alkyl, —N($C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, fluorine or chlorine atom, and hydroxy;

I is —$(CH_2)_m$—Y, wherein m is an integer of from 3 to 6, provided that m is an integer of from 3 to 5 when E is a group according to general formula (III);

Y represents a group:

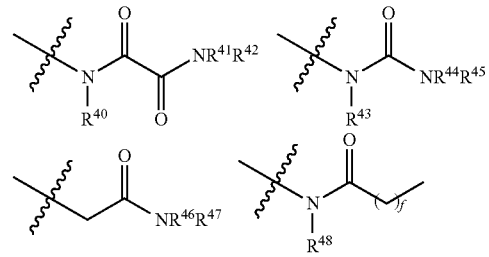

wherein $R^{40}$, $R^{41}$, $R^{43}$, $R^{44}$, $R^{46}$, and $R^{48}$ each independently represents a hydrogen atom, hydroxy, —$NH_2$, —$C_1$-$C_6$alkyl, —$C_3$-$C_6$cycloalkyl, —$C_1$-$C_6$alkoxy, —C(=O)aryl, or —C(=O)$C_1$-$C_6$alkyl, wherein any of the foregoing $C_1$-$C_6$alkyl, $C_3$-$C_6$cycloalkyl, $C_1$-$C_6$alkoxy, or aryl are optionally substituted with one, two or three substituents independently selected from the group consisting of —$NH_2$, —NH($C_1$-$C_6$)alkyl, —N($C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, fluorine or chlorine atom, and hydroxy; or $R^{40}$ and $R^{41}$, or $R^{43}$ and $R^{44}$, are taken together to form a 5-membered or 6-membered ring, which ring may be substituted with one, two or three substituents independently selected from the group consisting of —$NH_2$, —NH($C_1$-$C_6$)alkyl, —N($C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$) alkylaminocarbonyl-, fluorine or chlorine atom, and hydroxy;

$R^{42}$, $R^{45}$, and $R^{47}$ each independently represents a —$C_1$-$C_6$alkyl, wherein the $C_1$-$C_6$alkyl may be substituted with one, two or three substituents independently selected from the group consisting of —$NH_2$, —NH($C_1$-$C_6$)alkyl, —N($C_1$-$C_6$)dialkyl, $C_1$-$C_6$alkylcarbonyloxy-, $C_1$-$C_6$alkoxycarbonyloxy-, $C_1$-$C_6$alkyl-carbonylthio-, $C_1$-$C_6$alkylaminocarbonyl-, di($C_1$-$C_6$)alkylaminocarbonyl-, fluorine or chlorine atom, and hydroxy; or $R^{41}$ and $R^{42}$; $R^{44}$ and $R^{45}$; or $R^{46}$ and $R^{47}$ are taken together to form a 5-membered or 6-membered ring, which ring may be substituted with one, two or three substituents independently selected from the group consisting of —NH$_2$, —NH(C$_1$-C$_6$)alkyl, —N(C$_1$-C$_6$)dialkyl, C$_1$-C$_6$alkylcarbonyloxy-, C$_1$-C$_6$alkoxycarbonyloxy-, C$_1$-C$_6$alkylcarbonylthio-, C$_1$-C$_6$alkylaminocarbonyl-, di(C$_1$-C$_6$)alkylaminocarbonyl-, fluorine or chlorine atom, and hydroxy;

f is an integer of from 0 to 6;

with the provisio that (i) when n is 3, B is O or S, k is 1, E is a group according to general formula (IV), and each of R$^{12}$ and R$^{13}$ is a hydrogen atom; or when n is 5, 6, 7, or 8, B and k are as defined above, E is a group according to general formula (IV), and each of R$^{12}$ and R$^{13}$ is a hydrogen atom;

P represents a group:

—(CH$_2$)$_3$—O—(CH$_2$)—X$^{81}$; —(CH$_2$)$_5$—O—(CH$_2$)—X$^{81}$; —(CH$_2$)$_3$—S—(CH$_2$)—X$^{81}$; —(CH$_2$)$_5$—S—(CH$_2$)—X$^{81}$; —(CH$_2$)$_5$—O—X$^{82}$; —(CH$_2$)$_7$—O—X$^{82}$; —S—X$^{82}$; —O—X$^{82}$; —(CH$_2$)$_5$X$^{83}$ or —(CH$_2$)$_7$X$^{83}$;

wherein

X$^{81}$ A represents a group:

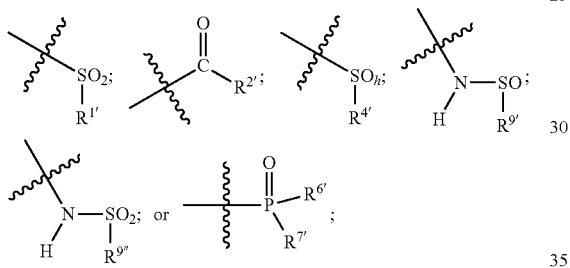

X$^{82}$ A represents a group:

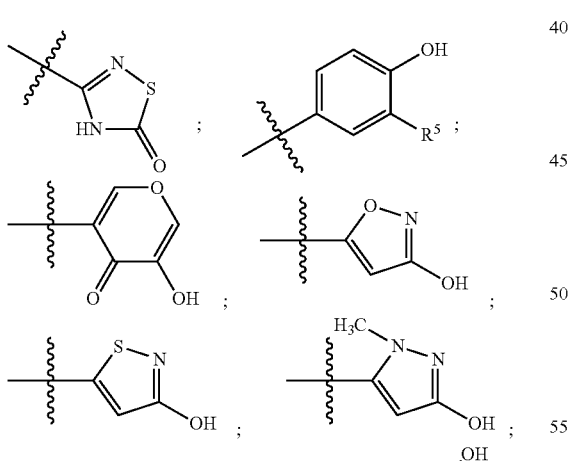

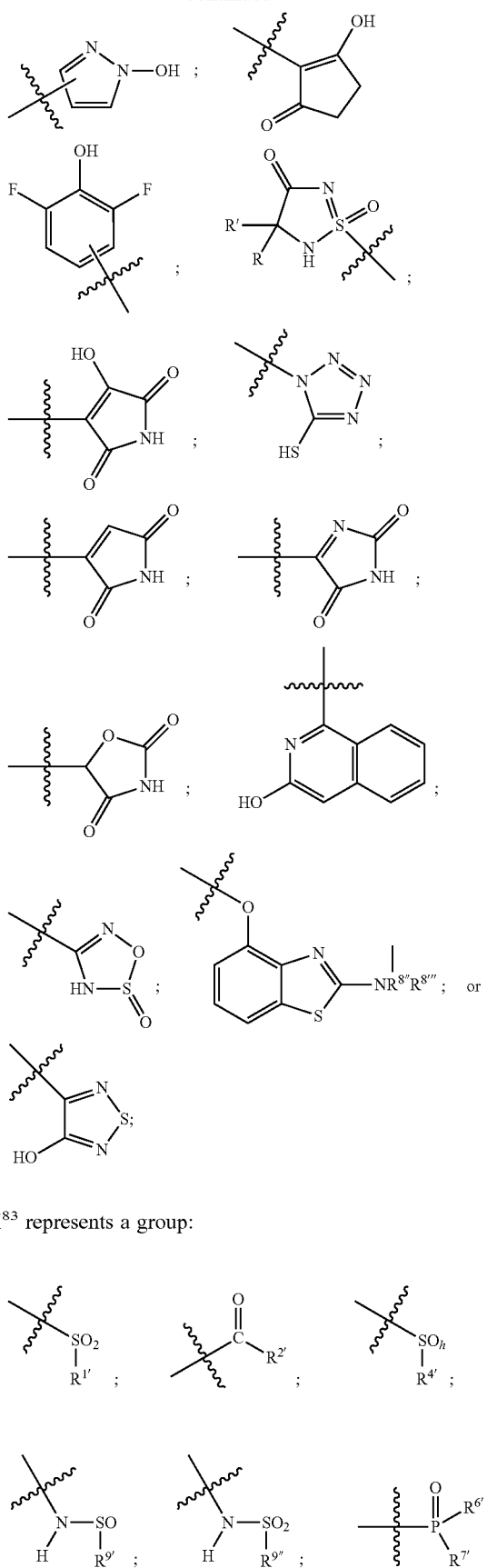

X$^{83}$ represents a group:

-continued

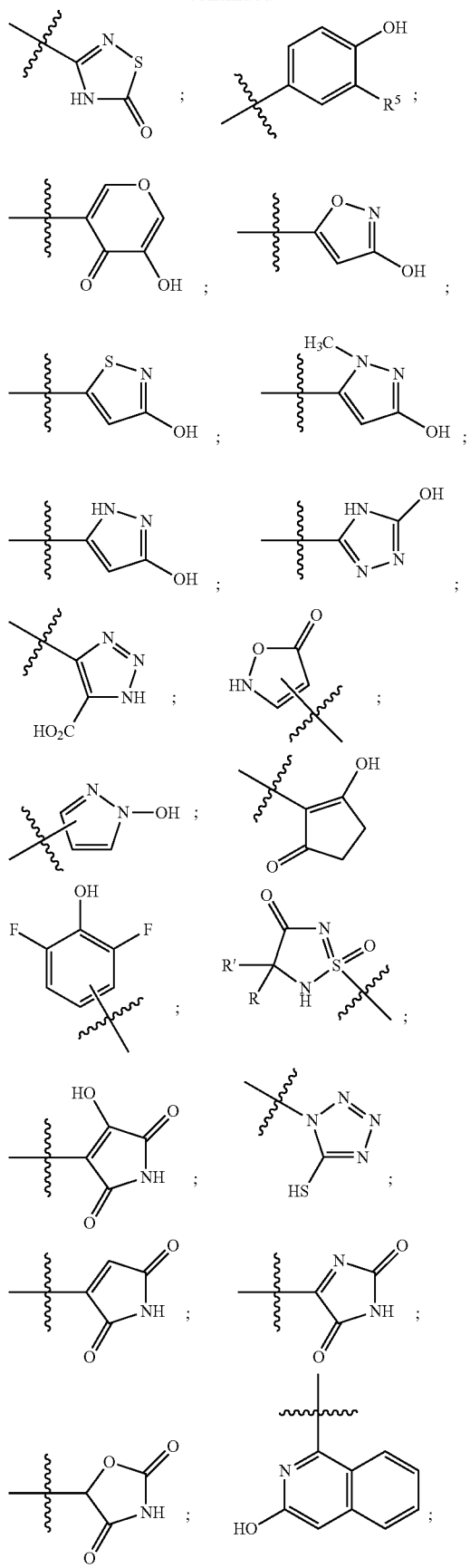

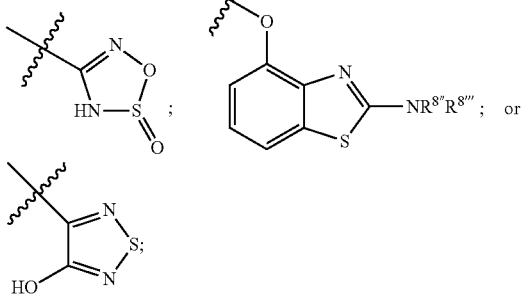

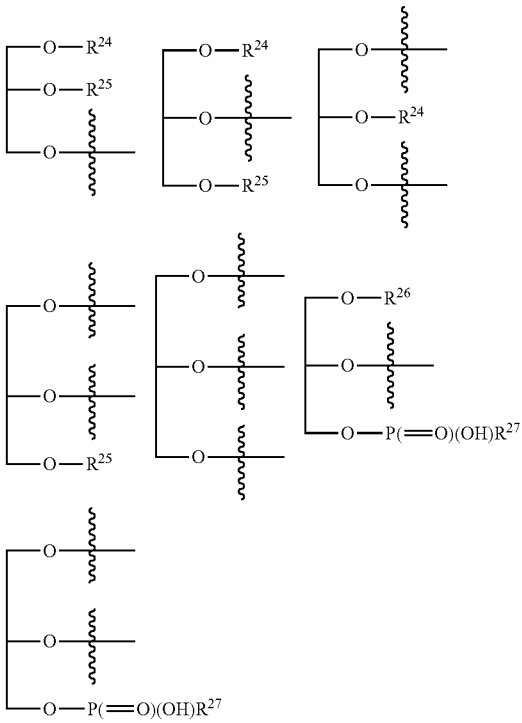

R and R' are defined as above;
R$^{1'}$ is defined as R$^1$ above;
R$^{2'}$ represents —NHR$^{3'}$; —OR$^{22'}$; —(OCH$_2$—CH$_2$)$_i$—R$^{23}$; a mono-, or disaccharide, or a derivative thereof, which is joined to —C(O) by an ester bond via the 1-O-, 3-O-, or 6-O-position of the saccharide; or is selected from the group consisting of:

wherein
R$^{3'}$ represents (SO$_2$R$^{30}$); (OR$^{31}$); —C$_1$-C$_6$alkanediyl (SO$_2$R$^{32}$); or —C$_2$-C$_6$alkanediyl(CO$_2$H);
R$^{22'}$ is a C$_3$-C$_6$cycloalkyl group, which is optionally substituted with —NH2, —NH(C$_1$-C$_6$)alkyl, —N(C$_1$-C$_6$dialkyl, —NH(C$_1$-C$_6$)alkyldiyl- C$_1$-C$_6$alkoxy, one, two or three fluorine or chlorine atom(s), hydroxy, or C$_1$-C$_6$alkoxy;
R$^{23}$ and i are as defined above, provided that when i=3 R$^{23}$ is not —OH;
R$^{24}$, R$^{25}$, R$^{26}$, and R$^{27}$ are as defined above;
R$^{4'}$ is defined as R$^4$ above; and h is defined as above;
R$^{6'}$ and R$^{7'}$ are defined as R$^6$ and R$^7$ above;
R$^{8''}$ and R$^{8'''}$ are defined as R$^8$ and R$^{8'}$ above;

$R^{9'}$ is defined as $R^9$ above; $R^{9''}$ represents aryl which is optionally substituted with one, two or three substituents independently selected from the group consisting of $C_1$-$C_6$alkyl, $C_1$-$C_6$alkoxy, $C_1$-$C_6$alkylthio, fluorine or chlorine atom, hydroxyl group, amino group, —NH($C_1$-$C_6$alkyl), —N($C_1$-$C_6$)dialkyl, and an oxo substituent; and (ii) the compounds (A) and (B) depicted below

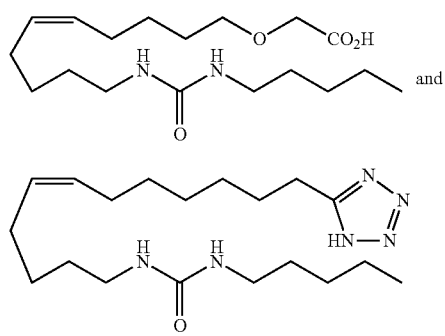

are excluded

Compounds are generally described herein using standard nomenclature. For compounds having asymmetric centers, it should be understood that, unless otherwise specified, all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

Compounds according to the formulas provided herein, which have one or more stereogenic center(s), have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors, biosynthesis, e.g. using modified CYP102 (CYP BM-3) or by resolution of the racemates, e.g. enzymatic resolution or resolution by conventional methods such as crystallization in the presence of a resolving agent, or chromatography, using, for example, a chiral HPLC column.

Certain compounds are described herein using a general formula that includes variables such as, e.g. P, E, I, B, $R^1$-$R^{54}$, X—$X^{83}$, and Y. Unless otherwise specified, each variable within such a formula is defined independently of any other variable, and any variable that occurs more than one time in a formula is defined independently at each occurrence. Thus, for example, if a group is shown to be substituted with 0-2 R*, the group may be unsubstituted or substituted with up to two R* groups, and R* at each occurrence is selected independently from the definition of R*. Also, combinations of substituents and/or variables are permissible only if such combinations result in stable compounds, i.e., compounds that can be isolated, characterized and tested for biological activity.

As used herein, "comprising", "including", "containing", "characterized by", and grammatical equivalents thereof are inclusive or open-ended terms that do not exclude additional, unrecited elements or method steps. "Comprising", etc. is to be interpreted as including the more restrictive term "consisting of".

As used herein, "consisting of" excludes any element, step, or ingredient not specified in the claim.

When trade names are used herein, it is intended to independently include the trade name product formulation, the generic drug, and the active pharmaceutical ingredient(s) of the trade name product.

In general, unless defined otherwise, technical and scientific terms used herein have the same meaning as commonly understood by one of ordinary skill in the art to which this invention belongs, and are consistent with general textbooks and dictionaries.

A "pharmaceutically acceptable salt" of a compound disclosed herein is an acid or base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids.

Suitable pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzenesulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is any integer from 0 to 6, i.e. 0, 1, 2, 3, 4, 5 or 6, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

It will be apparent that each compound of formula (I) may, but need not, be present as a hydrate, solvate or non-covalent complex. In addition, the various crystal forms and polymorphs are within the scope of the present invention.

A "substituent," as used herein, refers to a molecular moiety that is covalently bonded to an atom within a molecule of interest. For example, a "ring substituent" may be a moiety such as a halogen, alkyl group, haloalkyl group or other substituent described herein that is covalently bonded to an atom, preferably a carbon or nitrogen atom, that is a ring member.

The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated, characterized and tested for biological activity. When a substituent is oxo, i.e., =O, then 2 hydrogens on the atom are replaced. An oxo group that is a substituent of an aromatic carbon atom results in a conversion of —CH— to —C(=O)— and a loss of aromaticity. For example a pyridyl group substituted by oxo is a pyridone.

The expression "optionally substituted" refers to a group in which one, two, three or more hydrogen atoms may have been replaced independently of each other by the respective substituents.

As used herein, the term "amino acid" refers to any organic acid containing one or more amino substituents, e.g. α-, β- or γ-amino, derivatives of aliphatic carboxylic acids. In the polypeptide notation used herein, e.g. $Xaa_5$, i.e. $Xaa_1Xaa_2Xaa_3Xaa_4Xaa_5$, wherein $Xaa_1$ to $Xaa_5$ are each and independently selected from amino acids as defined, the lefthand direction is the amino terminal direction and the righthand direction is the carboxy terminal direction, in accordance with standard usage and convention.

The term "conventional amino acid" refers to the twenty naturally occurring amino acids, which are selected from the group consisting of Glycine, Leucine, Isoleucine, Valine, Alanine, Phenylalanine, Tyrosine, Tryptophan, Aspartic acid, Asparagine, Glutamic acid, Glutamine, Cysteine, Methionine, Arginine, Lysine, Proline, Serine, Threonine and Histidine, and encompasses all stereomeric isoforms, i.e. D,L-, D- and L-amino acids thereof. These conventional amino acids can herein also be referred to by their conventional three-letter or one-letter abbreviations and their abbreviations follow conventional usage (see, for example, *Immunology—A Synthesis*, $2^{nd}$ Edition, E. S. Golub and D. R. Gren, Eds., Sinauer Associates, Sunderland Mass. (1991)).

The term "non-conventional amino acid" refers to unnatural amino acids or chemical amino acid analogues, e.g. α,α-disubstituted amino acids, N-alkyl amino acids, homoamino acids, dehydroamino acids, aromatic amino acids (other than phenylalanine, tyrosine and tryptophan), and ortho-, meta- or para-aminobenzoic acid. Non-conventional amino acids also include compounds which have an amine and carboxyl functional group separated in a 1,3 or larger substitution pattern, such as β-alanine, γ-amino butyric acid, Freidinger lactam, the bicyclic dipeptide (BTD), aminomethyl benzoic acid and others well known in the art. Statine-like isosteres, hydroxyethylene isosteres, reduced amide bond isosteres, thioamide isosteres, urea isosteres, carbamate isosteres, thioether isosteres, vinyl isosteres and other amide bond isosteres known to the art may also be used. The use of analogues or non-conventional amino acids may improve the stability and biological half-life of the added peptide since they are more resistant to breakdown under physiological conditions. The person skilled in the art will be aware of similar types of substitution which may be made. A non limiting list of non-conventional amino acids which may be used as suitable building blocks for a peptide and their standard abbreviations (in brackets) is as follows: α-aminobutyric acid (Abu), L-N-methylalanine (Nmala), α-amino-α-methylbutyrate (Mgabu), L-N-methylarginine (Nmarg), aminocyclopropane (Cpro), L-N-methylaspara-gine (Nmasn), carboxylate L-N-methylaspartic acid (Nmasp), aniinoisobutyric acid (Aib), L-N-methylcysteine (Nmcys), aminonorbornyl (Norb), L-N-methylglutamine (Nmgln), carboxylate L-N-methylglutamic acid (Nmglu), cyclohexylalanine (Chexa), L-N-methylhistidine (Nmhis), cyclopentylalanine (Cpen), L-N-methylisolleucine (Nmile), L-N-methylleucine (Nmleu), L-N-methyllysine (Nmlys), L-N-methylmethionine (Nmmet), L-N-methylnorleucine (Nmnle), L-N-methylnorvaline (Nmnva), L-N-methylornithine (Nmorn), L-N-methylphenylalanine (Nmphe), L-N-methylproline (Nmpro), L-N-methylserine (Nmser), L-N-methylthreonine (Nmthr), L-N-methyltryptophan (Nmtrp), D-ornithine (Dorn), L-N-methyltyrosine (Nmtyr), L-N-methylvaline (Nmval), L-N-methylethylglycine (Nmetg), L-N-methyl-t-butylglycine (Nmtbug), L-norleucine (Nle), L-norvaline (Nva), α-methyl-aminoisobutyrate (Maib), α-methyl-γ-aminobutyrate (Mgabu), D-α-methylalanine (Dmala), α-methylcyclohexylalanine (Mchexa), D-α-methylarginine (Dmarg), α-methylcylcopentylalanine (Mcpen), D-α-methylasparagine (Dmasn), α-methyl-α-napthylalanine (Manap), D-α-methylaspartate (Dmasp), α-methylpenicillamine (Mpen), D-α-methylcysteine (Dmcys), N-(4-aminobutyl)glycine (Nglu), D-α-methylglutamine (Dmgln), N-(2-aminoethyl)glycine (Naeg), D-α-methylhistidine (Dmhis), N-(3-aminopropyl)glycine (Norn), D-α-methylisoleucine (Dmile), N-amino-α-methylbutyrate (Nmaabu), D-α-methylleucine (Dmleu), α-napthylalanine (Anap), D-α-methyllysine (Dmlys), N-benzylglycine (Nphe), D-α-methylmethionine (Dmmet), N-(2-carbamylethyl)glycine (Ngln), D-α-methylornithine (Dmorn), N-(carbamylmethyl)glycine (Nasn), D-α-methylphenylalanine (Dmphe), N-(2-carboxyethyl)glycine (Nglu), D-α-methylproline (Dmpro), N-(carboxymethyl)glycine (Nasp), D-α-methylserine (Dmser), N-cyclobutylglycine (Ncbut), D-α-methylthreonine (Dmthr), N-cycloheptylglycine (Nchep), D-α-methyltryptophan (Dmtrp), N-cyclohexylglycine (Nchex), D-α-methyltyrosine (Dmty), N-cyclodecylglycine (Ncdec), D-α-methylvaline (Dmval), N-cylcododecylglycine (Ncdod), D-N-methylalanine (Dnmala), N-cyclooctylglycine (Ncoct), D-N-methylarginine (Dnmarg), N-cyclopropylglycine (Ncpro), D-N-methylasparagine (Dnmasn), N-cycloundecylglycine (Ncund), D-N-methylaspartate (Dnmasp), N-(2,2-diphenylethyl)glycine (Nbhm), D-N-methylcysteine (Dnmcys), N-(3,3-diphenylpropyl)glycine (Nbhe), D-N-methylglutamine (Dnmgln), N-(3-guanidinopropyl)glycine (Narg), D-N-methylglutamate (Dnmglu), N-(1-hydroxyethyl)glycine (Ntbx), D-N-methylhistidine (Dnmhis), N-(hydroxyethyl))glycine (Nser), D-N-methylisoleucine (Dnmile), N-(imidazolylethyl))glycine (Nhis), D-N-methylleucine (Dnmleu), N-(3-indolylyethyl)glycine (Nhtrp), D-N-methyllysine (Dnnilys), N-methyl-γ-aminobutyrate (Nmgabu), N-methylcyclohexylalanine (Nmchexa), D-N-methylmethionine (Dnmmet), D-N-methylornithine (Dnmorn), N-methylcyclopentylalanine (Nmcpen), N-methylglycine (Nala), D-N-methylphenylalanine (Dnmphe), N-methylaminoisobutyrate (Nmaib), D-N-methylproline (Dnmpro), N-(1-methylpropyl)glycine (Nile), D-N-methylserine (Dnmser), N-(2-methylpropyl)glycine (Nleu), D-N-methylthreonine (Dnmthr), D-N-methyltryptophan (Dnmtrp), N-(1-methylethyl)glycine (Nval), D-N-methyltyrosine (Dnmtyr), N-methyla-napthylalanine (Nmanap), D-N-methylvaline (Dnmval), N-methylpenicillamine (Nmpen), γ-aminobutyric acid (Gabu), N-(p-hydroxyphenyl)glycine (Nhtyr), L-/-butylglycine (Tbug), N-(thiomethyl)glycine (Ncys), L-ethylglycine (Etg), penicillamine (Pen), L-homophenylalanine (Hphe), L-α-methylalanine (Mala), L-α-methylarginine (Marg), L-α-methylasparagine (Masn), L-α-methylaspartate (Masp), L-α-methyl-t-butylglycine (Mtbug), L-α-methylcysteine (Mcys), L-methylethylglycine (Metg), L-α-methylglutamine (Mgln), Lα-methylglutamate (Mglu), L-α-methylhistidine (Mhis), L-α-methylhomophenylalanine (Mhphe), L-α-methylisoleucine (Mile), N-(2-methylthioethyl)glycine (Nmet), L-α-methylleucine (Mleu), L-α-methyllysine (Mlys), L-α-methylmethionine (Mmet), L-α-methylnorleucine (Mnle), L-α-methylnorvaline (Mnva), L-α-methylornithine (Morn), L-α-methylphenylalanine (Mphe), L-α-methylproline (Mpro), L-α-methylserine (Mser), L-α-methylthreonine (Mthr), L-α-methyltryptophan (Mtrp), L-α-methyltyrosine (Mtyr), L-α-methylvaline (Mval), L-N-methylhomophenylalanine (Nmhphe), N—(N-(2,2-diphenylethyl)carbamylmethyl)glycine (Nnbhm), N—(N-(3,3-diphenylpropyl)carbamylmethyl)glycine (Nnbhe), 1-carboxy-1-(2,2-diphenyl-ethylamino)cyclopropane (Nmbc), L-O-methyl serine (Omser), L-O-methyl homoserine (Omhser).

The expression alkyl refers to a saturated, straight-chain or branched hydrocarbon group that contains from 1 to 20 carbon atoms, preferably from 1 to 10 carbon atoms, e.g. a n-octyl group, especially from 1 to 6, i.e. 1, 2, 3, 4, 5, or 6, carbon atoms, for example a methyl, ethyl, propyl, iso-propyl, n-butyl, iso-butyl, sec-butyl, tert-butyl, n-pentyl, iso-pentyl, n-hexyl, or 2,2-dimethylbutyl.

The expression alkenyl refers to an at least partially unsaturated, straight-chain or branched, hydrocarbon group that contains from 2 to 21 carbon atoms, preferably from 2 to 6 carbon atoms, i.e. 2, 3, 4, 5 or 6 carbon atoms, for example an ethenyl (vinyl), propenyl (allyl), iso-propenyl, butenyl, ethinyl, propinyl, butinyl, acetylenyl, propargyl, isoprenyl or hex-2-enyl group, or from 11 to 21 carbon atoms, i.e. 11, 12, 13, 14, 15, 16, 17, 18, 19, 20 or 21 carbon atoms, for example a hydrocarbon group comprising a methylene chain interrupted by one double bond as, for example, found in monounsaturated fatty acids or a hydrocarbon group comprising methylene-interrupted polyenes, e.g. hydrocarbon groups comprising two or more of the following structural unit —[CH=CH—CH$_2$]—, as, for example, found in polyunsaturated fatty acids. Alkenyl groups have one or more, preferably 1, 2, 3, 4, 5, or 6 double bond(s).

The expression alkoxy refers to an alkyl group singular bonded to oxygen.

The expression alkylthio refers to an alkyl group singular bonded to sulfur.

The expressions cycloalkyl and carbocyclic ring refer to a saturated cyclic group of hydrocarbons that contains one or more rings, preferably 1 or 2), and contains from 3 to 14 ring carbon atoms, preferably from 3 to 10, especially 3, 4, 5, 6 or 7 ring carbon atoms, e.g. a cyclopropyl, cyclobutyl, cyclopentyl, spiro[4,5]decanyl, norbornyl, cyclohexyl, decalinyl, bicyclo[4.3.0]nonyl, tetraline, or cyclopentylcyclohexyl group.

The expression aryl refers to an aromatic group that contains one or more rings containing from 6 to 14 ring carbon atoms, preferably from 6 to 10, especially 6, ring carbon atoms.

The expression heteroaryl refers to an aromatic group that contains one or more rings containing from 5 to 14 ring atoms, preferably from 5 to 10, especially 5 or 6, ring atoms, and contains one or more, preferably 1, 2, 3 or 4, oxygen, nitrogen, phosphorus or sulfur ring atoms, preferably O, S or N. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The expression heterocyclic ring refers to heteroaryl group as defined above as well as to a cycloalkyl group or carbocyclic ring as defined above in which one or more (preferably 1, 2 or 3) ring carbon atoms, each independently, have been replaced by an oxygen, nitrogen, silicon, selenium, phosphorus or sulfur atom, preferably by an oxygen, sulfur or nitrogen atom. A heterocyclic ring has preferably 1 or 2 ring(s) containing from 3 to 10, especially 3, 4, 5, 6 or 7 ring atoms, preferably selected from C, O, N and S. Examples are a aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, tetrahydrofuranyl, thiolanyl, phospholanyl, silolanyl, azolyl, thiazolyl, isothiazolyl, imidazolidinyl, pyrazolidinyl, oxazolidinyl, isoxazolidinyl, thiazolidinyl, isothiazolidinyl, dioxolanyl, dithiolanyl, piperazinyl, morpholinyl, thiopmorpholinyl, trioxanyl, azepanyl, oxepanyl, thiepanyl, homopiperazinyl, or urotropinyl group.

The general term ring as used herein, unless defined otherwise, includes cycloalkyl groups or carbocyclic rings, heterocyclic rings, aryl groups, and heteroaryl groups.

The expressions "halo", "halogen" or "halogen atom" as used herein means fluorine, chlorine, bromine, or iodine, preferably fluorine and/or chlorine.

The expression mono- or disaccharide, and derivatives thereof as used herein means a carbohydrate or sugar belonging to or derived from the group of monosaccharides or disaccharides.

Examples of mono-, disaccharides, and derivatives include glucose, 3-O-methyl-glucose, 1-deoxy-glucose, 6-deoxy-glucose, galactose, mannose, fructose, xylose, ribose, cellobiose, maltose, lactose, gentiobiose, saccharose, trehalose and mannitol, sorbitol and ribitol. Preferably, the saccharides are D-form saccharides, e.g. D-glucose, 3-O-methyl-D-glucose, 1-deoxy-D-glucose, or 6-deoxy-D-glucose, D-galactose, D-mannose.

As used herein a wording defining the limits of a range of length such as, e. g., "from 1 to 5" means any integer from 1 to 5, i. e. 1, 2, 3, 4 and 5. In other words, any range defined by two integers explicitly mentioned is meant to comprise and disclose any integer defining said limits and any integer comprised in said range.

According to the invention, the compound of formula (I) may be a compound, wherein E is a group represented by the general formula (IV); one of $R^{12}$ and $R^{13}$ represents a hydrogen atom and the other represents a fluorine atom, hydroxy, —NH2, $C_1$-$C_6$alkyl, $C_1$-$C_6$alkoxy, —C(=O)-aryl, —C(=O)$C_1$-$C_6$alkyl, or —SO$_2$($C_1$-$C_6$alkyl); or —SO$_2$aryl; wherein any of the foregoing $C_1$-$C_6$alkyl, $C_1$-$C_6$alkoxy, or aryl are optionally substituted with one, two or three substituents independently selected from the group consisting of —NH$_2$, —NH($C_1$-$C_6$)alkyl, —N($C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, fluorine or chlorine atom, and hydroxy; or $R^{12}$ and $R^{13}$ are taken together to form a 5-membered or 6-membered ring, which ring is optionally substituted with one, two or three substituents independently selected from the group consisting of —NH$_2$, —NH($C_1$-$C_6$) alkyl, —N($C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, fluorine or chlorine atom, and hydroxy; and P and I are defined as above.

According to the invention, the compound of formula (I) can also be a compound, wherein E is a group represented by the general formula (IV); $R^{12}$ and $R^{13}$ each independently represents a fluorine atom, hydroxy, —NH2, $C_1$-$C_6$alkyl, $C_1$-$C_6$alkoxy, —C(=O)-aryl, —C(=O)$C_1$-$C_6$alkyl, or —$SO_2$($C_1$-$C_6$alkyl); or —$SO_2$aryl; wherein any of the foregoing $C_1$-$C_6$alkyl, $C_1$-$C_6$alkoxy, or aryl are optionally substituted with one, two or three substituents independently selected from the group consisting of —$NH_2$, —NH($C_1$-$C_6$)alkyl, —N($C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, fluorine or chlorine atom, and hydroxy; or $R^{12}$ and $R^{13}$ are taken together to form a 5-membered or 6-membered ring, which ring is optionally substituted with one, two or three substituents independently selected from the group consisting of —$NH_2$, —NH($C_1$-$C_6$)alkyl, —N($C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, fluorine or chlorine atom, and hydroxy; and P and I are defined as above.

Preferably, the compound of formula (I) can be a compound, wherein E is a group represented by the general formula (IV); I is defined as above; and P represents a group: —$(CH_2)_3$—O—$(CH_2)$—$X^{81}$; —$(CH_2)_5$—O—$(CH_2)$—$X^{81}$; —$(CH_2)_3$—S—$(CH_2)$—$X^{81}$; —$(CH_2)_5$—S—$(CH_2)$—$X^{81}$; —$(CH_2)_5$—O—$X^{82}$; —$(CH_2)_7$—O—$X^{82}$; —S—$X^{82}$; —O—$X^{82}$; —$(CH_2)_5$$X^{83}$ or —$(CH_2)_7$$X^{83}$; wherein $X^{81}$, $X^{82}$ and $X^{83}$ are defined as above.

In the compound according to the invention, P can represent a group —$(CH_2)_5$-$X^{83}$ or —$(CH_2)_7$-$X^{83}$; wherein $X^{83}$ is defined as above.

The compound according to the invention can be a compound, wherein $X^{83}$ represents a group selected from the groups consisting of:

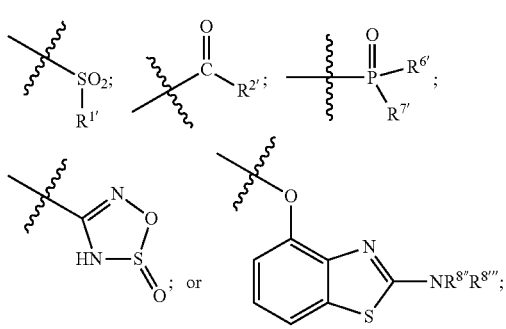

wherein $R^{1'}$, $R^{2'}$, $R^{6'}$, $R^{7'}$, $R^{8'''}$, and $R^{8''''}$ are defined as above.

Preferably, the compound of the invention can be a compound, wherein $R^{1'}$ is a hydroxyl group; and $R^{2'}$ represents —$NHR^{3'}$ or the group

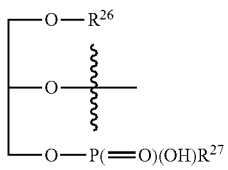

wherein
$R^{3'}$ is ($SO_2R^{30}$), $R^{30}$ is —$C_1$-$C_6$alkyl or phenyl; $R^{26}$ is defined as above; $R^{27}$ is —$OCH_2$—[CH($NH_2$)($CO_2H$)], —O($CH_2$)$_2$N($CH_3$)$_3$; or

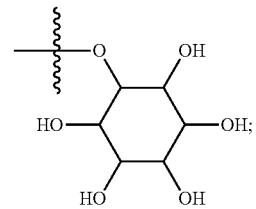 [SMILES: *OC1C(O)C(O)C(O)C(O)C1O]

$R^{6'}$ and $R^{7'}$ each independently represents a hydroxyl group; an —O($C_1$-$C_6$)alkyl group; or an —O($CH_2$)O(C=O)($C_1$-$C_6$)alkyl group; and $R^{8'''}$ is hydrogen atom; and $R^{8''''}$ is C(=O)$C_1$-$C_6$alkyl.

The compound of formula (I) can also be a compound, wherein E is a group represented by the general formula (III); and P, and I are defined as above.

The compound of formula (I) may be a compound, wherein E is a group represented by the general formula (III); L and T each independently represents a carbon, nitrogen, or sulfur atom; at least one of L and T represents a carbon atom; P, and I are defined as above.

Preferably, L and T each independently represents a carbon or nitrogen atom with at least one of L and T being a carbon atom. L and T may both represent a carbon atom.

Preferably, the compound of formula (I) can be a compound, wherein E is

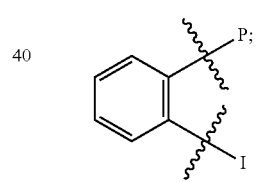

and

P and I are as defined above; preferably P represents a group —$(CH_2)_6$-X, —$(CH_2)_7$-X, —$(CH_2)_8$-X, or —$(CH_2)_9$-X; more preferably P represents a group —$(CH_2)_6$-X, or —$(CH_2)_9$-X; and most preferably P represents a group —$(CH_2)_9$-X; wherein X is defined as above; more preferably X is

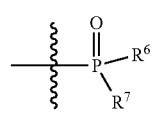

with $R^6$ and $R^7$ being defined as above; more preferably $R^6$ and $R^7$ each independently represents an —O($CH_2$)O(C=O)($C_1$-$C_6$)alkyl group.

In the compound according to the invention, I can be —$(CH_2)_m$—Y with m being 3; and Y representing a group:

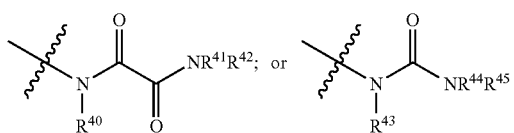

wherein
$R^{40}$, $R^{41}$, $R^{43}$, and $R^{44}$ each represents a hydrogen atom; and $R^{42}$ and $R^{45}$ each independently represents a —$C_1$-$C_6$alkyl group.

In a compound according to the invention, wherein E is a group represented by the general formula (III); I is preferably —$(CH_2)_m$—Y; m is 4; and Y represents a group:

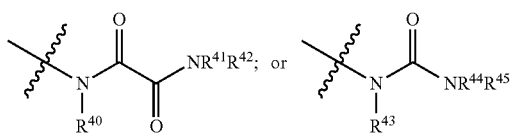

wherein
$R^{40}$, $R^{41}$, $R^{43}$, and $R^{44}$ each represents a hydrogen atom; and $R^{42}$ and $R^{45}$ each independently represents a —$C_1$-$C_6$alkyl group.

In a compound according to the invention, $R^{42}$ can preferably be a methyl group; and $R^{45}$ can preferably be an ethyl group.

In a compound according to the invention, $R^{24}$, $R^{25}$, and $R^{26}$ can each independently represent a hydrogen atom; —C(=O)$(CH_2)_{10}CH_3$, —C(=O)$(CH_2)_{12}CH_3$, —C(=O)$(CH_2)_{14}CH_3$, —C(=O)$(CH_2)_{16}CH_3$, —C(=O)$(CH_2)_{18}CH_3$, —C(=O)$(CH_2)_{20}CH_3$; —C(=O)$(CH_2)_7$CH=CH$(CH_2)_3CH_3$, —C(=O)$(CH_2)_7$CH=CH$(CH_2)_5CH_3$, —C(=O)$(CH_2)_4$CH=CH$(CH_2)_8CH_3$, —C(=O)$(CH_2)_7$CH=CH$(CH_2)_5CH_3$, —C(=O)$(CH_2)_9$CH=CH$(CH_2)_5CH_3$, —C(=O)$(CH_2)_{11}$CH=CH$(CH_2)_7CH_3$, —C(=O)$(CH_2)_7$CH=CHCH$_2$CH=CH$(CH_2)_4CH_3$, —C(=O)$(CH_2)_7$(CH=CHCH$_2$)$_3CH_3$, —C(=O)$(CH_2)_3$(CH=CHCH$_2$)$_4$(CH$_2$)$_3CH_3$, —C(=O)$(CH_2)_3$(CH=CHCH$_2$)$_5CH_3$, or —C(=O)$(CH_2)_2$(CH=CHCH$_2$)$_6CH_3$. Preferably, $R^{24}$, $R^{25}$, and $R^{26}$ can each independently represent a hydrogen atom; —C(=O)$(CH_2)_{10}CH_3$, —C(=O)$(CH_2)_{12}CH_3$, —C(=O)$(CH_2)_{14}CH_3$, —C(=O)$(CH_2)_{16}CH_3$; —C(=O)$(CH_2)_7$CH=CH$(CH_2)_5CH_3$, —C(=O)$(CH_2)_7$CH=CH$(CH_2)_7CH_3$, —C(=O)$(CH_2)_7$CH=CHCH$_2$CH=CH$(CH_2)_4CH_3$, —C(=O)$(CH_2)_7$(CH=CHCH$_2$)$_3CH_3$, —C(=O)$(CH_2)_3$(CH=CHCH$_2$)$_4$(CH$_2$)$_3CH_3$, —C(=O)$(CH_2)_3$(CH=CHCH$_2$)$_5CH_3$, or —C(=O)$(CH_2)_2$(CH=CHCH$_2$)$_6CH_3$.

The compound according to the invention can be a compound selected from the group consisting of: from the group consisting of:

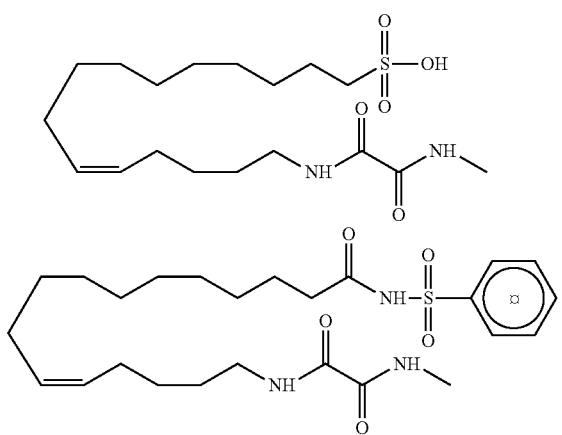

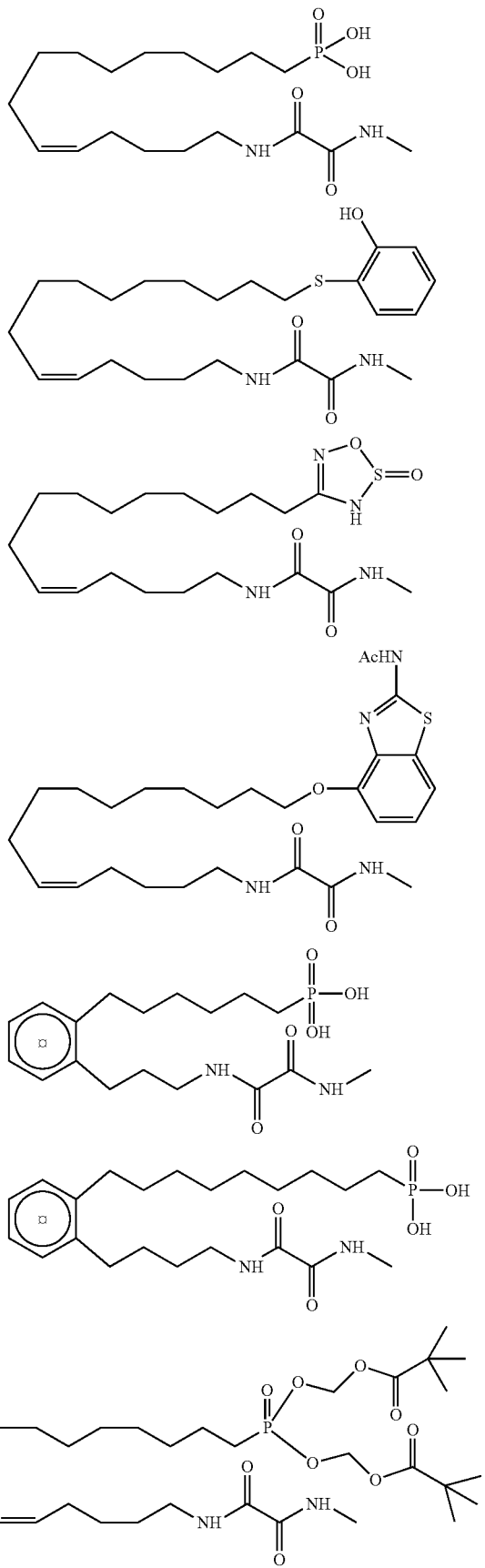

It is especially preferred to combine the preferred embodiments of the individual generic groups of formula (I) in any possible manner.

Those skilled in the art will readily recognize that some of the n-3 PUFA analogues of general formula (I) of the present invention represent "bioisosteres" of the naturally occurring epoxymetabolites produced by cytochrome P450 (CYP) enzymes from omega-3 (n-3) polyunsaturated fatty acids (PUFAs). A bioisostere is a compound resulting from the exchange of an atom or of a group of atoms with an alternative, broadly similar, atom or group of atoms, thereby creating a new compound with similar biological properties to the parent compound. Bioisosterism has, for example, been used by medicinal chemists for improving desired biological or physical properties of a compound, e.g. to attenuate toxicity, modify activity, alter pharmacokinetics and/or metabolism of a compound. For example, the replacement of a hydrogen atom with fluorine at a site of metabolic oxidation in a compound may prevent such metabolism from taking place. Because fluorine is similar in size to the hydrogen atom the overall topology of the molecule is not significantly affected, leaving the desired biological activity unaffected. However, with a blocked pathway for metabolism, said compound may have a longer half-life. Another example is the bioisosteric replacement of carboxylic acid groups which has resulted in analogues showing improved bioavailability, enhanced blood-brain barrier penetration, increased activity, better chemical stability and/or selectivity towards the target (see, e.g. the textbook "The practice of medicinal chemistry", edited by Camille Georges Wermuth, $3^{rd}$ edition, Academic Press, 2008, e.g. p. 303-310; Ballatore C. et al. "Carboxylic Acid (Bio)Isosteres in Drug Design", Chem Med Chem 8, 385-395 (2013)). Further, bioisosterism can also be used to provide a "prodrug" of a compound, i.e. a compound that is initially administered to a subject or patient in an inactive (or less active) form, and then becomes modified in vivo to its active form through the normal metabolic processes of the body. For example, conjugation of a compound with lipid and/or sugar units has resulted in analogues (prodrugs) showing increased drug delivery compared to the parent compound (see, e.g. Wong A. and Toth I. "Lipid, Sugar and Liposaccharide Based Delivery Systems", Current Medicinal Chemistry 8, 1123-1136 (2001)).

The n-3 PUFA analogues of general formula (I) of the present invention can be prepared in a number of ways well known to one skilled in the art of organic synthesis. For example, the compounds of the present invention can be synthesized according to the general Reaction Schemes 1 to 4 shown below using synthetic methods known in the art of synthetic organic chemistry, or variations thereon as appreciated by those skilled in the art. Unless indicated otherwise, all variables, e.g. n, k, $R^2$ (also referred to as $R_2$), $R^6$, $R^7$, $R^8$, $R^{41}$, $R^{42}$, $R^{44}$ and $R^{45}$, have the above defined meaning. As starting materials reagents of standard commercial grade can be used without further purification, or can be readily prepared from such materials by routine methods. Those skilled in the art of organic synthesis will recognize that starting materials and reaction conditions may be varied including additional steps employed to produce compounds encompassed by the present invention.

Reaction Scheme 1

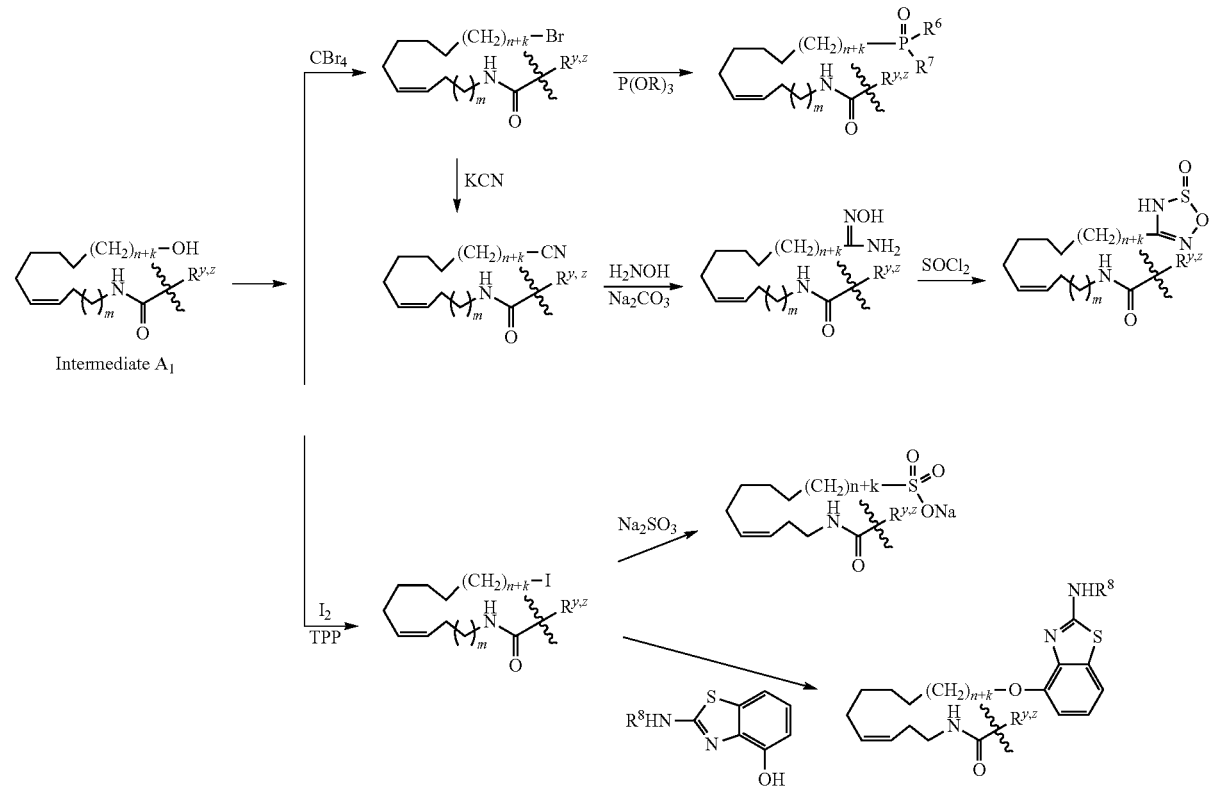

m = 3-6

$R^y$ and $R^z$ defined as shown here are equally defined in Reaction Schemes 2 to 10
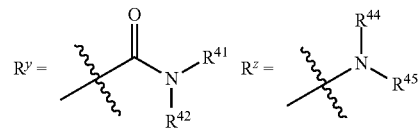
Reaction Scheme 2
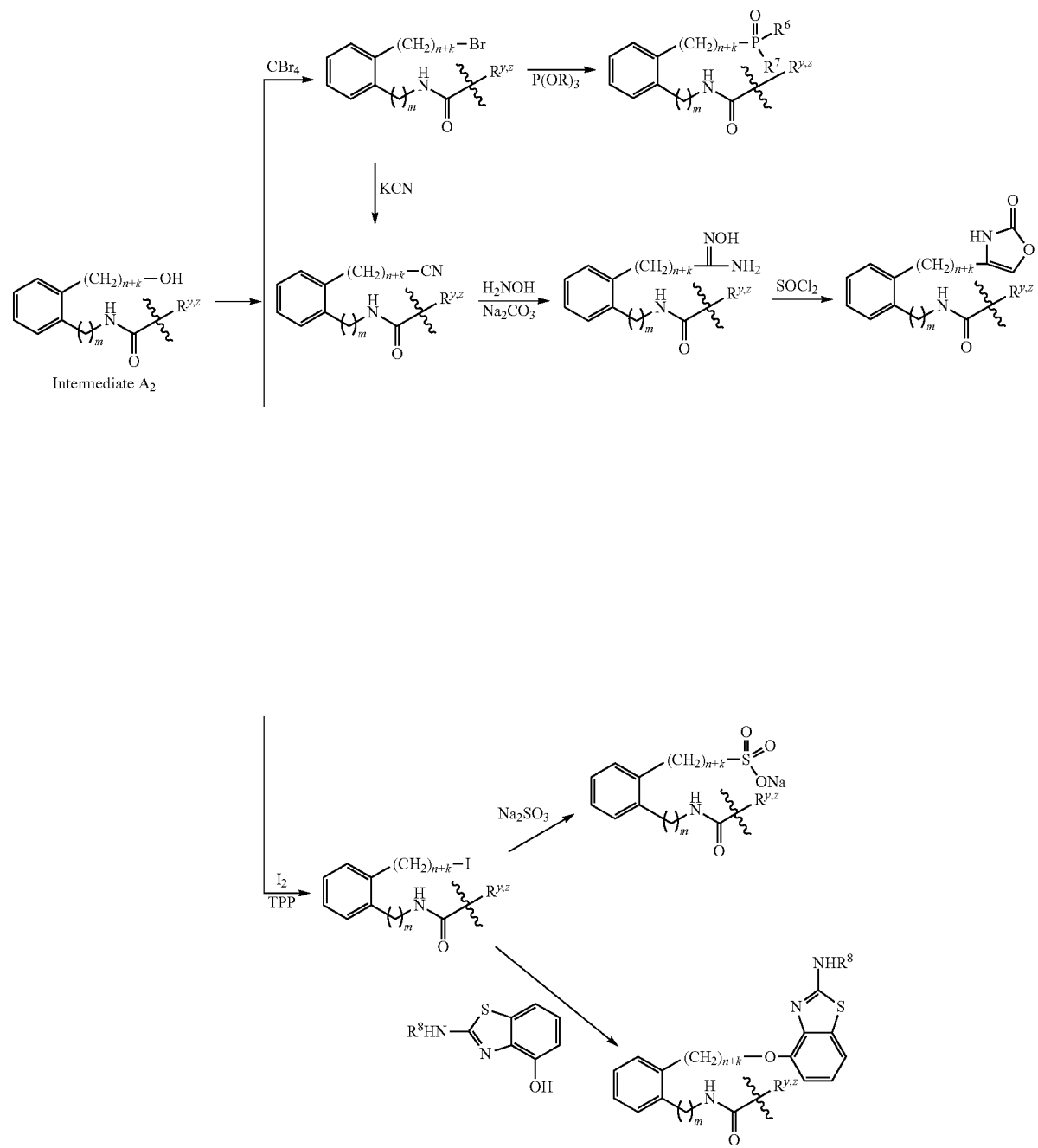
Intermediate A$_2$
m = 3-5

Reaction Scheme 3

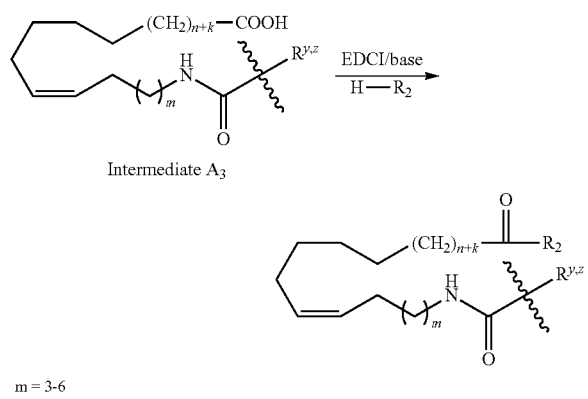

Intermediate A$_3$ m = 3-6

Reaction Scheme 4

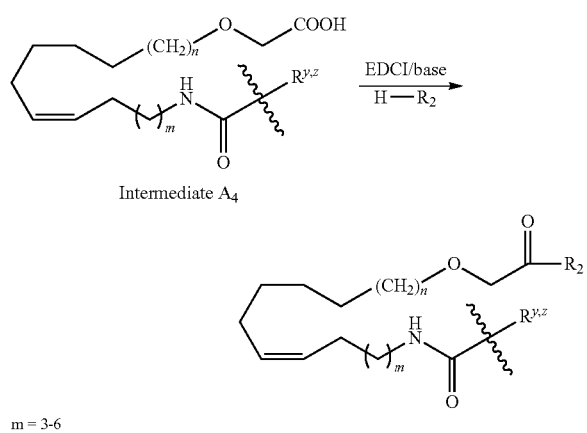

Intermediate A$_4$ m = 3-6

Reaction Scheme 5

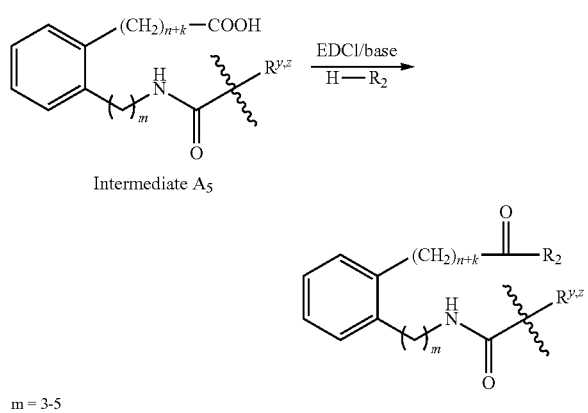

Intermediate A$_5$ m = 3-5

The above Intermediates A$_1$ to A$_5$ can, for example, be synthesized according to the general Reaction Schemes 6 to 10 shown below using synthetic methods known in the art of synthetic organic chemistry, or variations thereon as appreciated by those skilled in the art.

Reaction Scheme 6

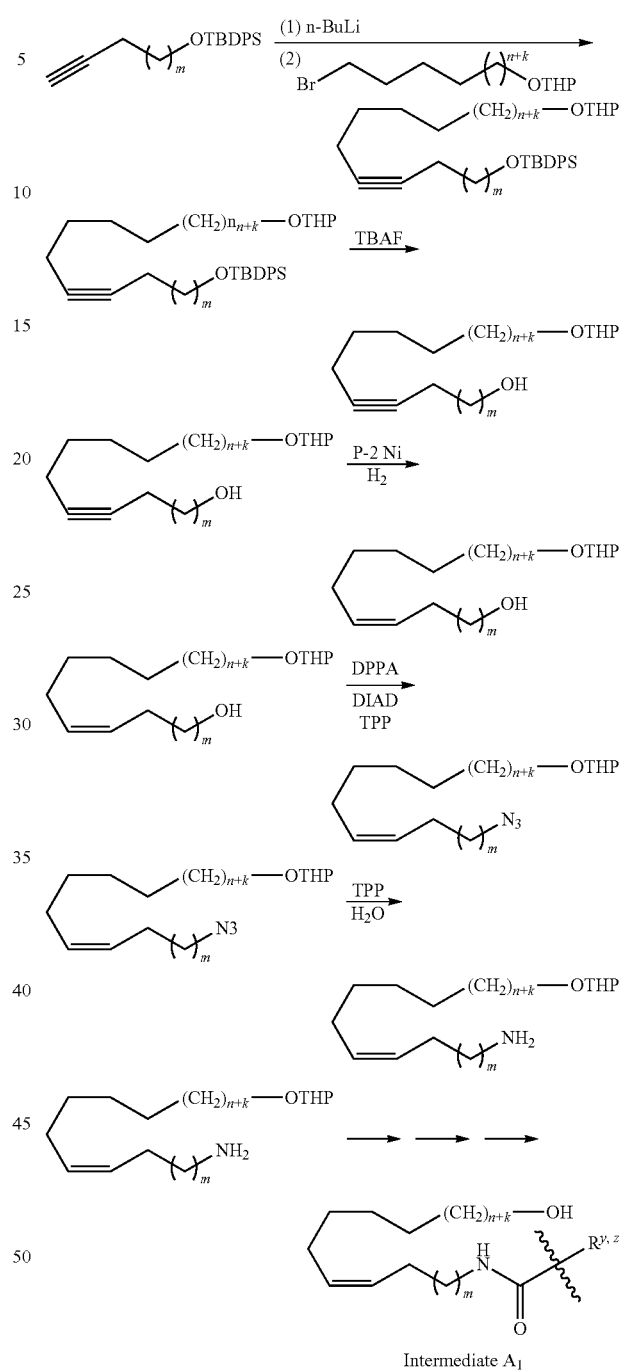

m = 3-6
B represents a carbon-carbon bond

Reaction Scheme 7

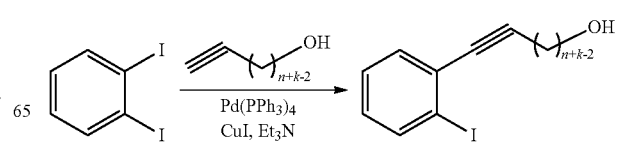

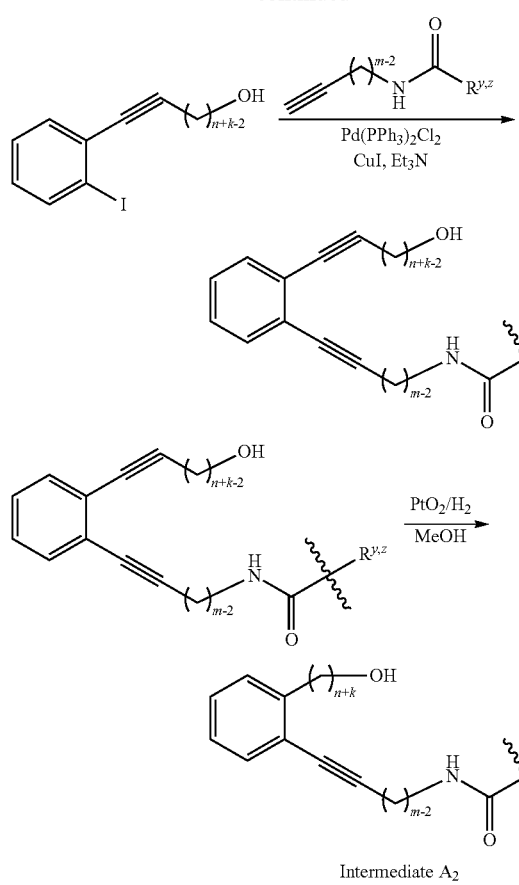
m = 3-5
B represents a carbon-carbon bond
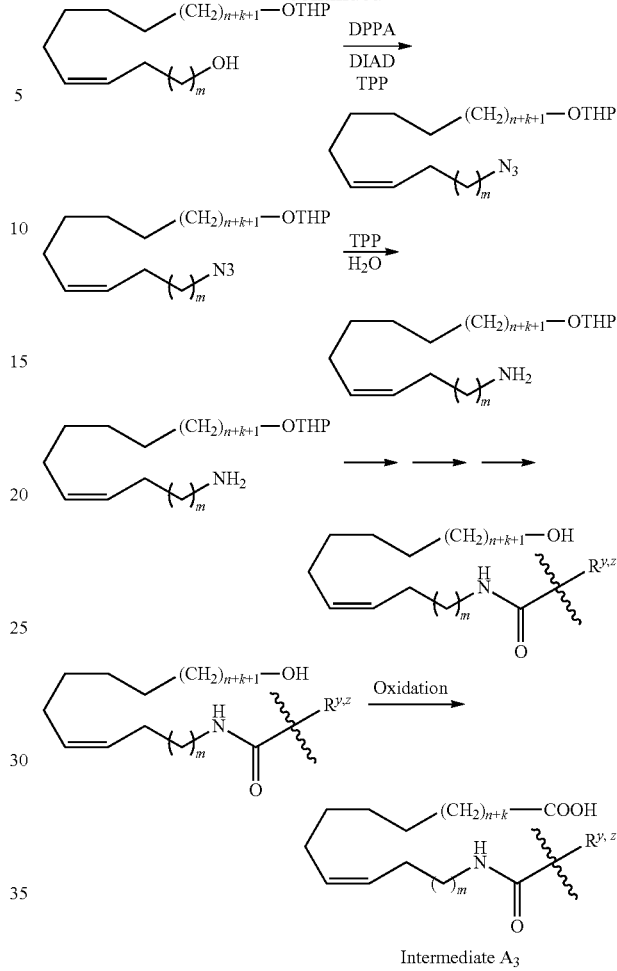
Intermediate A₃
m = 3-6
B represents a carbon-carbon bond
Reaction Scheme 8
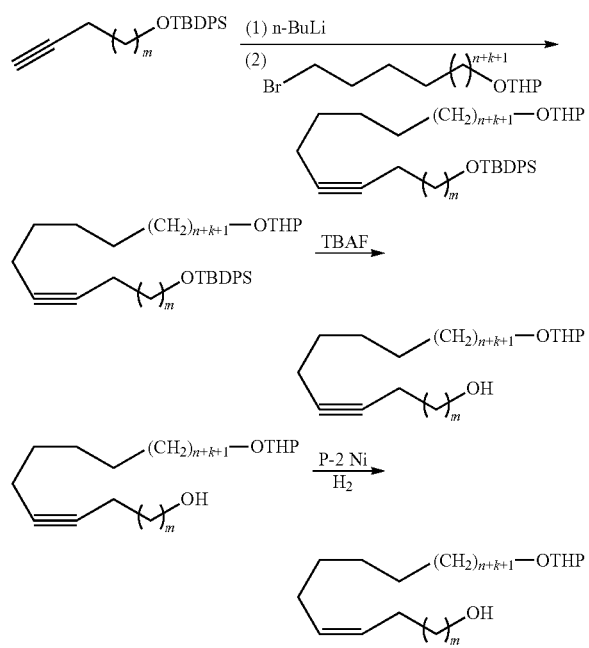
Reaction Scheme 9
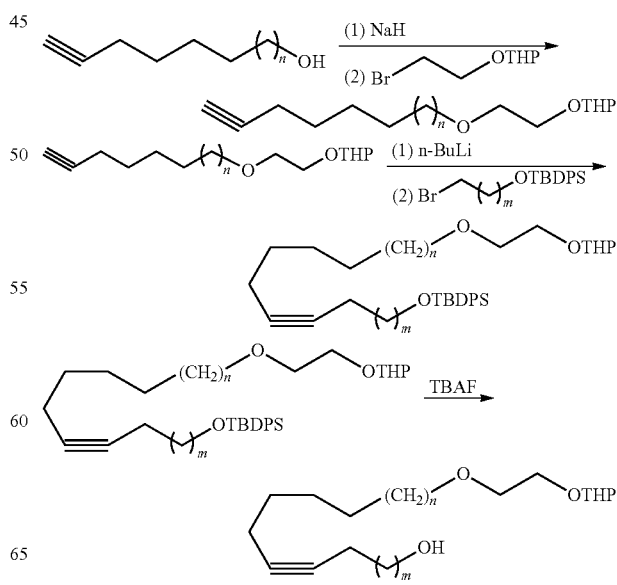

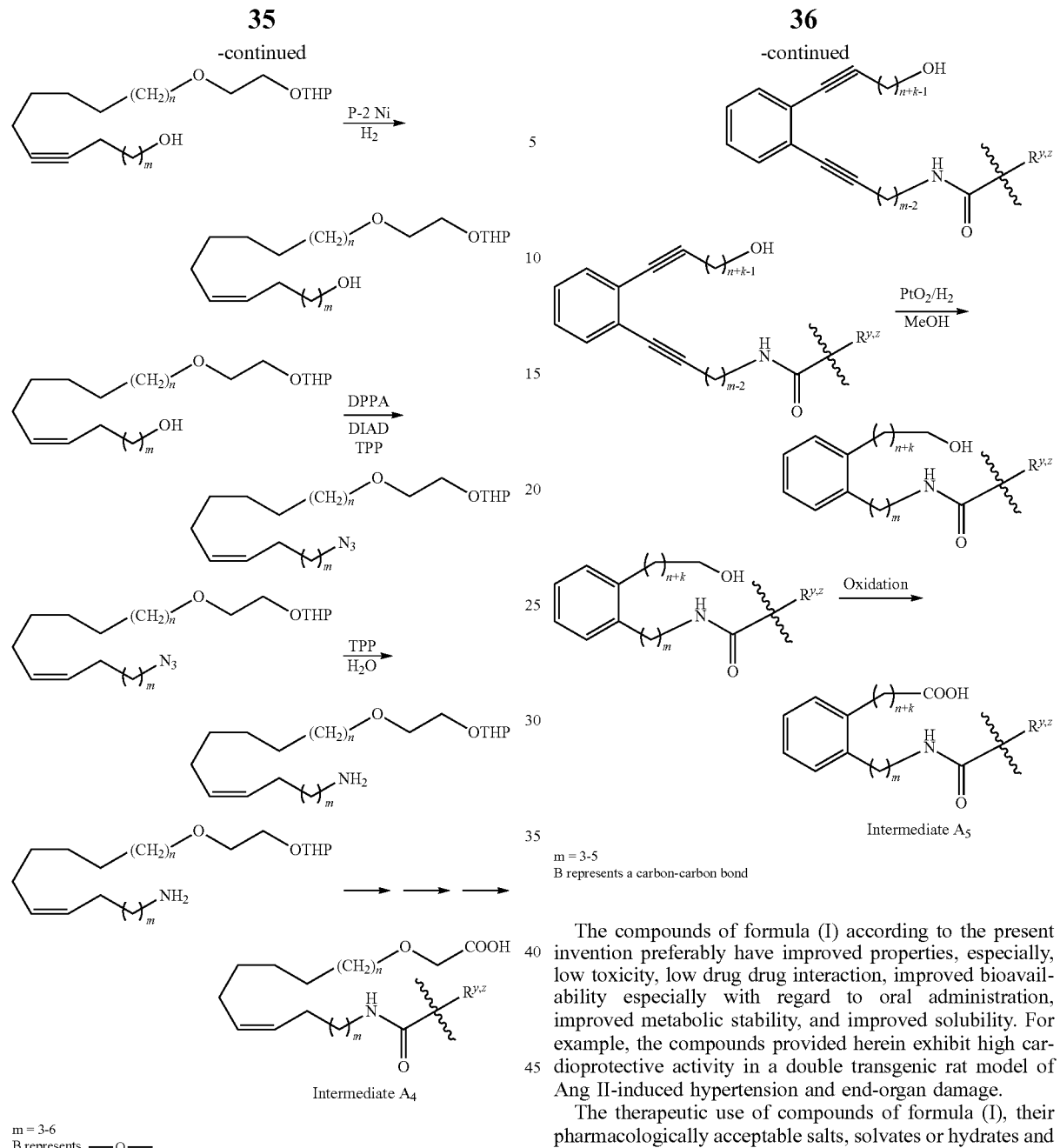

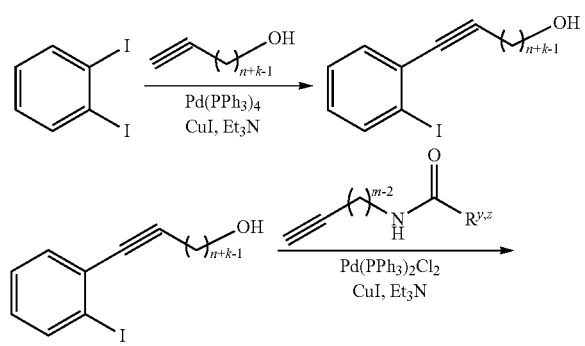

m = 3-6
B represents —O—

Reaction Scheme 10

The compounds of formula (I) according to the present invention preferably have improved properties, especially, low toxicity, low drug drug interaction, improved bioavailability especially with regard to oral administration, improved metabolic stability, and improved solubility. For example, the compounds provided herein exhibit high cardioprotective activity in a double transgenic rat model of Ang II-induced hypertension and end-organ damage.

The therapeutic use of compounds of formula (I), their pharmacologically acceptable salts, solvates or hydrates and also formulations and pharmaceutical compositions lie within the scope of the present invention. The present invention also relates to the use of those compounds of formula (I) as active ingredients in the preparation of medicaments and also to their use as well as the use of a pharmaceutical composition according to the invention in the treatment or prevention of a condition and/or disease associated with inflammation, proliferation, hypertension, coagulation, immune function, pathologic angiogenesis, or cardiac disease.

The compound or pharmaceutical composition of the present invention can be used in the treatment or prevention of a cardiac disease. The cardiac disease can be selected from the group consisting of heart failure, coronary artery disease, myocardial infarction, acute and chronic inflammatory cardiac damage, maladaptive cardiac hypertrophy, and cardiac arrhythmias.

Preferably, the compound or pharmaceutical composition of the present invention can be used in the treatment or prevention of cardiac arrhythmias, including ventricular tachycardia and supraventricular arrhythmia. More preferably, the compound or pharmaceutical composition of the present invention can be used in the treatment or prevention of supraventricular arrhythmia, especially in the treatment or prevention of atrial fibrillation.

The pharmaceutical compositions according to the present invention comprise at least one compound of formula (I) and, optionally, one or more carrier substances, e.g. cyclodextrins such as hydroxypropyl β-cyclodextrin, micelles or liposomes, excipients and/or adjuvants. Pharmaceutical compositions may additionally comprise, for example, one or more of water, buffers such as, e.g., neutral buffered saline or phosphate buffered saline, ethanol, mineral oil, vegetable oil, dimethylsulfoxide, carbohydrates such as e.g., glucose, mannose, sucrose or dextrans, mannitol, proteins, adjuvants, polypeptides or amino acids such as glycine, antioxidants, chelating agents such as EDTA or glutathione and/or preservatives. Furthermore, one or more other active ingredients may, but need not, be included in the pharmaceutical compositions provided herein. For instance, the compounds of the invention may advantageously be employed in combination with an antibiotic, anti-fungal, or anti-viral agent, an anti-histamine, a non-steroidal anti-inflammatory drug, a disease modifying anti-rheumatic drug, an anti-inflammatory drug to treat an autoimmune disease, a cytostatic drug, a drug with smooth muscle activity modulatory activity, an antihypertensive drug, a betablocker, an antiarrhythmic drug, a drug to treat heart failure, an antithrombotic drug, an antiplatelet drug, or mixtures of the aforementioned. Preferably, the invention relates to a combination preparation or kit-of-parts comprising at least one compound according to the invention and at least one drug from the group comprising an antihypertensive drug, a betablocker, an antiarrhythmic drug, a drug to treat heart failure, an antithrombotic drug, an antiplatelet drug, an anti-rheumatic drug, and/or an anti-inflammatory drug to treat an autoimmune disease.

Pharmaceutical compositions may be formulated for any appropriate route of administration, including, for example, topical such as, e.g., transdermal or ocular, oral, buccal, nasal, vaginal, rectal or parenteral administration. The term parenteral as used herein includes subcutaneous, intradermal, intravascular such as, e.g., intravenous, intramuscular, spinal, intracranial, intrathecal, intraocular, periocular, intraorbital, intrasynovial and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. Formulation for topical administration may be preferred for certain conditions such as, e.g., in the treatment of skin conditions such as burns or itch.

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents such as, e.g., calcium carbonate, sodium carbonate, lactose, calcium phosphate or sodium phosphate, granulating and disintegrating agents such as, e.g., corn starch or alginic acid, binding agents such as, e.g., starch, gelatin or acacia, and lubricating agents such as, e.g., magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent such as, e.g., calcium carbonate, calcium phosphate or kaolin, or as soft gelatin capsules wherein the active ingredient is mixed with water or an oil medium such as, e.g., peanut oil, liquid paraffin or olive oil.

Aqueous suspensions contain the active ingredient(s) in admixture with excipients suitable for the manufacture of aqueous suspensions. Such excipients include suspending agents such as, e.g., sodium carboxymethylcellulose, methylcellulose, hydropropylmethylcellulose, sodium alginate, polyvinylpyrrolidone, gum tragacanth and gum acacia; and dispersing or wetting agents such as, e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil such as, e.g., arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil such as, e.g., olive oil or arachis oil, a mineral oil such as, e.g., liquid paraffin, or a mixture thereof. Suitable emulsifying agents include naturally-occurring gums such as, e.g., gum acacia or gum tragacanth, naturally-occurring phosphatides such as, e.g., soy bean lecithin, and esters or partial esters derived from fatty acids and hexitol, anhydrides such as, e.g., sorbitan monoleate, and condensation products of partial esters derived from fatty acids and hexitol with ethylene oxide such as, e.g., polyoxyethylene sorbitan monoleate. An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Compounds may be formulated for local or topical administration, such as for topical application to the skin or mucous membranes, such as in the eye. Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols such as, e.g., ethanol or isopropyl alcohol or glycerin; glycols such as, e.g., butylene, isoprene or propylene glycol; aliphatic alcohols such as, e.g., lanolin; mixtures of water and organic solvents and mixtures of organic solvents such as alcohol and glycerin; lipid-based materials such as fatty acids, acylglycerols including oils, such as, e.g., mineral oil, and fats of natural or synthetic origin, phosphoglycerides, sphingolipids and waxes; protein-based materials such as collagen and gelatin; silicone-based materials, both non-volatile and volatile; and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatin-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids, emulsions, sprays, eye-drops and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations.

Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate.

Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included in a topical formulation include, but are not limited to, abrasives, absorbents, anti-caking agents, anti-foaming agents, anti-static agents, astringents such as, e.g., witch hazel, alcohol and herbal extracts such as chamomile extract, binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%); Quaternium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying including mist, aerosol or foam spraying; dropper application; sprinkling; soaking; and rinsing. Controlled release vehicles can also be used, and compositions may be formulated for transdermal administration as a transdermal patch.

A pharmaceutical composition may be formulated as inhaled formulations, including sprays, mists, or aerosols. Such formulations are particularly useful for the treatment of asthma or other respiratory conditions. For inhalation formulations, the compounds provided herein may be delivered via any inhalation methods known to those skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Formulations or compositions suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation.

Pharmaceutical compositions may also be prepared in the form of suppositories such as e.g., for rectal administration. Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations such as, i.e., a formulation such as a capsule that creates a slow release of modulator following administration. Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

For the treatment of cardiac damage, especially cardiac arrhythmias, the dose of the biologically active compound according to the invention may vary within wide limits and may be adjusted to individual requirements. Active compounds according to the present invention are generally administered in an effective amount, e.g., in a therapeutically effective amount. Preferred doses range from about 0.1 mg to about 140 mg per kilogram of body weight per day, about 0.5 mg to about 7 g per patient per day. The daily dose may be administered as a single dose or in a plurality of doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination, i.e. other drugs being used to treat the patient, and the severity of the particular disease undergoing therapy.

Preferred compounds of the invention will have certain pharmacological properties. Such properties include, but are not limited to oral bioavailability, such that the preferred oral dosage forms discussed above can provide therapeutically effective levels of the compound in vivo.

n-3 PUFA derivatives provided herein are preferably administered to a patient such as, e.g., a human, orally or parenterally, and are present within at least one body fluid or tissue of the patient. Accordingly, the present invention further provides methods for treating patients suffering from conditions and diseases associated with inflammation, proliferation, hypertension, coagulation, immune function, pathologic angiogenesis, or, cardiac disease, including cardiac arrhythmias. As used herein, the term "treatment" encompasses any type of disease-modifying treatment including symptomatic treatment, i.e., a treatment after the onset of symptoms. However, disease-modifying treatment may involve administration before the onset of symptoms, in order to at least delay or reduce the severity of symptoms after onset. A disease-modifying treatment may also be therapeutic, i.e., after the onset of symptoms, in order to reduce the severity and/or duration of symptoms. A treatment after onset of symptoms may also simply involve stopping progressing of the disease (stable disease). In certain embodiment, the n-3 PUFA derivatives provided herein are administered prophylactically, i.e., before the onset of the disease and/or symptoms, ideally, but not necessarily, to actually prevent the diseases and/or symptoms. It is to be understood that the term prophylaxis and prophylactic in the context of the present invention, simply describes that the compound(s) of the present invention are administered before the onset of symptoms. A prophylactic administration may an administration before the onset of symptoms that are clearly associated with a disease discussed herein: the n-3 PUFA derivatives provided herein may, e.g., be administered to a subject prophylactically when he or she displays certain conditions that may indicate a propensity to develop one of the conditions or diseases that can be treated with one of the n-3 PUFA derivatives of the present invention. Such indicative conditions are, e.g. high blood pressure or diabetes. Such a prophylactic treatment is called primary prophylaxis. In another embodiment, the n-3 PUFA derivatives provided herein may be administered to a subject prophylactically when he or she has previously suffered from a condition or disease that can be treated with the the n-3 PUFA derivatives of the present invention, but currently does not display any symptoms. Such a prophylactic treatment is called secondary prophylaxis. Patients receiving the n-3 PUFA derivatives for the purpose of primary or secondary prophylaxis are considered to be in need of such a treatment. Patients may include but are not limited to primates, especially humans, domesticated companion animals such as dogs, cats, horses, and livestock such as cattle, pigs, sheep, with dosages as described herein.

As the person skilled in the art will appreciate, a wide variety of condition and diseases will benefit from the administration of the n-3PUFA derivatives of the present invention, the most prominent of which are cardiac diseases.

In one example, a patient suffering from cardiac arrhythmias receives orally two daily doses of 10 mg of a n-3PUFA derivative disclosed herein. During a 6 months treatment period the patient's disease does not progress.

In another example, a patient that previously suffered from cardiac arrhythmias receives orally a single daily dose 5mg of a n-3PUFA derivative disclosed herein. During a 6 months treatment period the patient remains disease free.

Examples of conditions and diseases associated with proliferation include tumors or neoplasms, where proliferation of cells is uncontrolled and progressive. Some such uncontrolled proliferating cells are benign, but others are termed "malignant" and may lead to death of the organism. Malignant neoplasms or "cancers" are distinguished from benign growths in that, in addition to exhibiting aggressive cellular proliferation, they may invade surrounding tissues and metastasize. Moreover, malignant neoplasms are characterized in that they show a greater loss of differentiation (greater "dedifferentiation"), and greater loss of their organization relative to one another and their surrounding tissues. This property is also called "anaplasia". Neoplasms treatable by the present invention also include solid phase tumors/malignancies, i. e., carcinomas, locally advanced tumors and human soft tissue sarcomas. Carcinomas include those malignant neoplasms derived from epithelial cells that infiltrate (invade) the surrounding tissues and give rise to metastatic cancers, including lymphatic metastases. Adenocarcinomas are carcinomas derived from glandular tissue, or which form recognizable glandular structures. Another broad category or cancers includes sarcomas, which are tumors whose cells are embedded in a fibrillar or homogeneous substance like embryonic connective tissue. The invention also enables treatment of cancers of the myeloid or lymphoid systems, including leukemias, lymphomas and other cancers that typically do not present as a tumor mass, but are distributed in the vascular or lymphoreticular systems. The type of cancer or tumor cells that may be amenable to treatment according to the invention include, for example, breast, colon, lung, and prostate cancers, gastrointestinal cancers including esophageal cancer, stomach cancer, colorectal cancer, polyps associated with colorectal neoplasms, pancreatic cancer and gallbladder cancer, cancer of the adrenal cortex, ACTH-producing tumor, bladder cancer, brain cancer including intrinsic brain tumors, neuroblastomas, astrocytic brain tumors, gliomas, and metastatic tumor cell invasion of the central nervous system, Ewing's sarcoma, head and neck cancer including mouth cancer and larynx cancer, kidney cancer including renal cell carcinoma, liver cancer, lung cancer including small and non-small cell lung cancers, malignant peritoneal effusion, malignant pleural effusion, skin cancers including malignant melanoma, tumor progression of human skin keratinocytes, squamous cell carcinoma, basal cell carcinoma, and hemangiopericytoma, mesothelioma, Kaposi's sarcoma, bone cancer including osteomas and sarcomas such as fibrosarcoma and osteosarcoma, cancers of the female reproductive tract including uterine cancer, endometrial cancer, ovarian cancer, ovarian (germ cell) cancer and solid tumors in the ovarian follicle, vaginal cancer, cancer of the vulva, and cervical cancer; breast cancer (small cell and ductal), penile cancer, retinoblastoma, testicular cancer, thyroid cancer, trophoblastic neoplasms, and Wilms' tumor.

Examples of conditions and diseases associated with inflammation and immune function include inflammatory disorders such as acute-phase reaction, local and systemic inflammation and inflammation caused by other diseases whatever type, etiology or pathogenesis and caused by inflammatory diseases exemplified below, and immunological disorders such as hyperesthesia, autoimmune disorders, graft rejection in transplantation, transplant toxicity, granulomatous inflammation/tissue remodelling, myasthenia gravis, immunosuppression, immune-complex diseases, over- and underproduction of antibodies, and vasculitis. In particular, examples of such conditions and diseases include inflammatory bowel disease including Crohn's disease and ulcerative colitis (Stadnicki et al., *Am. J. Physiol. Gastrointest Liver Physiol.* 2005, 289(2), G361-6; Devani et al., *Am. J. Gastroenerol* 2002, 97(8), 2026-32; Devani et al., *Dig. Liv. Disease* 2005, 37(9), 665-73), irritable bowel syndrome, enterocolitis, liver diseases, pancreatitis, nephritis, cystitis (interstitial cystitis), uveitis, retinitis, glaucoma, otitis media, peridontitis, inflammatory skin disorders such as psoriasis, eczema, atopic diseases, dermatitis, itching, juvenile or adult onset rheumatoid arthritis and gouty arthritis (Cassim et al., *Pharmacol. Ther.* 2002, 94, 1-34; Sharma et al., *Exp. Toxic Pathol.* 1994, 46, 421-433; Brechter et al., *Arthr. Rheum.* 2007, 56(3), 910-923), ankylosing spondylitis, adult onset or pediatric (systemic onset juvenile idiopathic arthritis) Still's disease, psoriatic arthritis, osteoarthritis and edema associated with burns, sprains or fracture, cerebral edema, closed head injury, angioedema, vasculitis, diabetic vasculopathy, type I diabetes, diabetic nephropathy, diabetic neuropathy, diabetic retinopathy, post capillary resistance or diabetic syndromes associated with insulits (e.g. hyperglycemia, diuresis, proteinuria and increased nitrite and kallikrein urinary excretion), gall bladder diseases, smooth muscle relaxants for the treatment of spasms of the gastrointestinal tract or uterus, multiple sclerosis, epilepsy, amyotrophic lateral sclerosis, Alzheimer's disease, stroke, Parkinson's disease, systemic inflammatory response syndrome (SIRS), ischemia-reperfusion injury and atherosclerosis (Raidoo et al., *Immunopharmacol* 1997, 36(2-3), 153-60; McLean et al., *Cardiovasc. Res.* 2000, 48, 194-210), septic shock, antihypovolemic and/or anti-hypotensive agents, headache including cluster headache, migraine including prophylactic and acute use, closed head trauma, cancer, sepsis, gingivitis, osteoporosis, benign prostatic hyperplasia, hyperactive bladder, fibrotic diseases such as pulmonary fibrosis, renal fibrosis, liver fibrosis, progressive sclerosis and recurrent stricture formation in Crohn's disease (Goldstein et al., *J. Biol. Chem.* 1984, 259(14), 9263-8; Ricupero et al., *J. Biol. Chem.* 2000, 275(17), 12475-80; Romero et al., *J. Biol. Chem.* 2005, 15, 14378-14384), disorders of the respiratory pathways in asthma, atopic or non-atopic asthma, occupational asthma, exercise-induced bronchoconstriction, bronchitis, pneumoconiosis including aluminosis, anhracosis, asbestosis, chalicosis, ptilosis, siderosis, silicosis, tabaccosis and byssinosis, chronic obstructive pulmonary disease including emphysema, adult respiratory distress syndrome, pneumonia, allergic rhinitis, vasomotor rhinitis and pleurisy, auto-inflammatory diseases such as familial Mediterranean fever (FMF), tumor-necrosis factor receptor associated periodic syndrome (TRAPS), neonatal onset multisystem inflammatory disease (NOMID), familial cold autoinflammatory syndrome (FCAS) including familial cold urticaria (FCU), pyogenic arthritis pyoderma gangrenosum acne (PAPA) syndrome and Muckle-Wells disease.

Examples of conditions and diseases associated with pathological angiogenesis include tumor development and metastasis as described above, age-related macular degeneration, and diabetic retinopathy.

Examples of conditions and diseases associated with cardiac disease include heart failure, coronary artery disease, myocardial infarction, acute and chronic inflammatory cardiac damage, maladaptive cardiac hypertrophy, and cardiac arrhythmias including ventricular tachycardia, malignant ventricular tachycardia and atrial fibrillation, dilatative cardiomyopathy, myocarditis, hypertensive heart disease, inflammatory cardiomyopathy.

Preferably, the method of preventing and/or treating any one of the above conditions or diseases comprises administering to a subject in need thereof at least an effective amount of an inventive n-3 PUFA analogue or of a pharmaceutical composition according to the invention. The method of preventing or treating said conditions or disorders may, moreover, be characterized in that the active inventive n-3 PUFA analogue or composition is intended to be administered by one of the above routes of administration, preferably orally or by injection.

The n-3 PUFA analogue according to the invention may also be used as a research tool. For instance, the mutein conjugate according to the invention may be used as a diagnostic agent or theranostic, whereby such diagnostic agent may be used for the diagnosis of the diseases and conditions which can be addressed by the n-3 PUFA analogues of the present invention for therapeutic purposes as disclosed herein. For instance, for use as a research tool, the n-3 PUFA analogue of the invention can be labelled by isotopes, fluorescence or luminescence markers, or any other affinity label. The labelled compounds of the invention are, for example, useful for mapping the location of receptors in vivo, in vitro and in situ (e.g. in tissue sections via autoradiography) and as radiotracers for positron emission tomography (PET) imaging, single photon emission computerized tomography (SPECT) and the like to characterize those receptors in living subjects or other materials, e.g. tissue samples. Such uses and their respective conditions are known to those skilled in the art.

The activity of the n-3 PUFA analogues according to the invention can, for example, be determined in appropriate in vitro and/or in vivo assays. For instance, the biological activity of the n-3 PUFA analogues according to the present invention may be determined using the established cell model of Kang and Leaf (Proc Natl Acad Sci USA, 1994. 91(21): p. 9886-90.) known to those skilled in the art.

BRIEF DESCRIPTION OF THE FIGURES

FIG. 1: Examples of n-3 PUFA analogues according to the present invention and their effect on an established in vitro cardiac arrhythmia model using spontaneously beating neonatal rat cardiomyocytes (NRCMs) compared to eicosapentaenoic acid (EPA) and 17,18-epoxyeicosatetraenoic acid (17,18-EEQ). As demonstrated, spontaneous beating of the cells under basal conditions was reduced by the application of the example analogs.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Specific examples for the preparation of compounds of formula (I) are provided in the following examples. Unless otherwise specified all starting materials and reagents are of standard commercial grade, and are used without further purification, or are readily prepared from such materials by routine methods. Those skilled in the art of organic synthesis will recognize that starting materials and reaction conditions may be varied including additional steps employed to produce compounds encompassed by the present invention. Preferred methods include but are not limited to those methods described below. Each of the references cited in connection with the described route of synthesis is hereby incorporated herein by reference.

Example 1

Preparation of Intermediate 10

Step A. Synthesis of tert-butyldiphenyl((15-((tetrahydro-2H-pyran-2-yl)oxy)pentadec-5-yn-1-yl)oxy)silane (3)

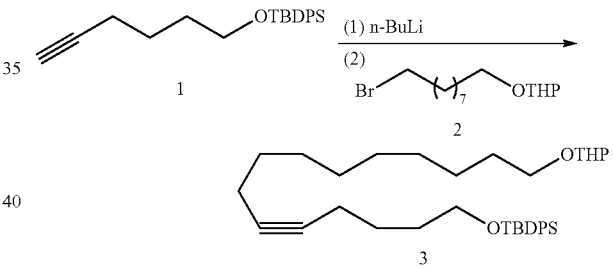

n-BuLi (2.5 M in hexanes, 1 eqiv) was added dropwise to a −78° C. solution of 1 (1 eqiv) in anhydrous THF and freshly distilled HMPA (3:1). The reaction was stirred at −78° C. for 30 min and at 0° C. for 2 h. The reaction was re-cooled to −78° C. and 2 (1.2 eqiv) in dry THF was added slowly. After 40 min at −78° C. and at rt overnight (14 h), the reaction was quenched with sat. NH$_4$Cl solution, water was added and the reaction was extracted twice with EtOAc. The combined organic extracts were washed twice with water, dried over Na$_2$SO$_4$, filtered and concentrated under vacuum. Purification via SiO$_2$ column chromatography using 2% EtOAc/hexanes afforded 3 (89%) as a colorless oil.

$^1$H NMR (500 MHz, CDCl$_3$) δ 7.70-7.63 (m, 4H), 7.47-7.30 (m, 6H), 4.61-4.54 (m, 1H), 3.92-3.82 (m, 1H), 3.78-3.70 (m, 1H), 3.67 (t, J=6.2 Hz, 1H), 3.56-3.45 (m, 1H), 3.44-3.33 (m, 1H), 2.22-2.07 (m, 2H), 1.90-1.39 (m, 10H), 1.39-1.23 (m, 9H), 1.04 (s, 9H), 0.92-0.81 (m, 2H); $^{13}$C NMR (125 MHz, CDCl$_3$) δ 135.80 (4), 134.26 (2), 129.76 (2), 127.84 (4), 99.08, 80.67, 80.22, 67.90, 63.73, 62.57, 31.99, 31.05, 30.01, 29.75, 29.73, 29.41, 29.39, 29.13, 27.12 (3), 26.48, 25.82, 25.77, 19.97, 19.47, 19.02, 18.81.

Step B. Synthesis of 15-((tetrahydro-2H-pyran-2-yl)oxy)pentadec-5-yn-1-ol (4)

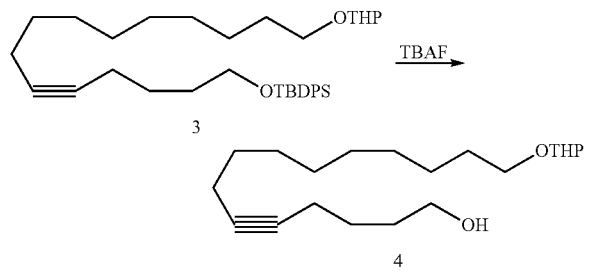

To a solution of 3 in dry THF was added tetra-n-butylammonium fluoride (TBAF, 1.0 M soln in THF, 1.3 equiv). After 39 h, the THF was evaporated, the residue was suspended in water, and extracted twice with Et$_2$O. The organic extracts were dried over MgSO$_4$, filtered, and concentrated in vacuo. The residue was purified using a Teledyne Isco Combiflash® RF chromatographic system to give alcohol 4 (61%) as a colorless oil.

$^1$H NMR (500 MHz, CDCl$_3$) δ 4.57 (dd, J=4.5, 2.8 Hz, 1H), 3.91-3.83 (m, 1H), 3.72 (dt, J=9.5, 6.9 Hz, 1H), 3.67 (t, J=6.4 Hz, 2H), 3.54-3.44 (m, 1H), 3.37 (dt, J=9.5, 6.7 Hz, 1H), 2.19 (tt, J=6.9, 2.4 Hz, 2H), 2.13 (tt, J=7.1, 2.4 Hz, 2H), 1.89-1.77 (m, 1H), 1.77-1.40 (m, 13H), 1.40-1.24 (m, 10H); $^{13}$C NMR (125 MHz, CDCl$_3$) δ 98.98, 80.75, 79.96, 67.86, 62.50 (2), 32.03, 30.93, 29.90, 29.61, 29.26 (2), 29.01, 26.39, 25.67, 25.60 (2), 19.83, 18.90, 18.73.

Step C. Synthesis of 15-(tetrahydro-2H-pyran-2-yloxy)pentadec-5(Z)-en-1-ol (5)

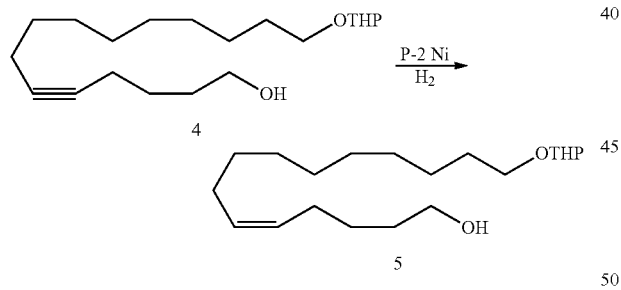

To a suspension of Ni(OAc)$_2$ (0.6 equiv) in absolute ethanol in a two necked flask under H$_2$ (1 atm) was added NaBH$_4$ (0.8 equiv) in one portion. After 25 min, distilled ethylenediamine (EDA, 3 equiv) was added neat followed by a solution of 4 in absolute EtOH. After 2 h, the reaction mixture was filtered through a pad of silica gel. The pad was washed with EtOAc. The combined organic filtrates were concentrated to give olefin 5 (98%), obtained as a colorless oil.

TLC: 20% EtOAc/hexanes, R$_f$~0.35. $^1$H NMR (500 MHz, CDCl$_3$) δ 5.41-5.31 (m, 2H), 4.59-4.56 (m, 1H), 3.89-3.85 (m, 1H), 3.73 (dt, J=9.7, 6.9 Hz, 1H), 3.65 (t, J=6.5 Hz, 2H), 3.53-3.47 (m, 1H), 3.38 (dt, J=9.7, 6.9 Hz, 1H), 2.06 (dt, J=7.0, 6.5 Hz, 2H), 2.01 (dt, J=7.0, 6.5 Hz, 2H), 1.87-1.79 (m, 1H), 1.75-1.68 (m, 1H), 1.64-1.48 (m, 9H), 1.46-1.38 (m, 2H), 1.38-1.24 (m, 11H); $^{13}$C NMR (125 MHz, CDCl$_3$) δ 130.5, 129.6, 99.0, 67.9, 62.8 (2), 62.5, 32.6, 30.9, 29.9, 29.8(2), 29.7, 29.5, 27.4, 27.2, 26.4, 26.1, 25.6, 19.8.

Step D. Synthesis of 2-(15-azidopentadec-10(Z)-enyloxy)tetrahydro-2H-pyran (6)

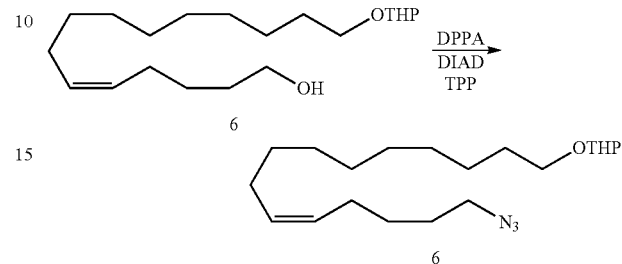

To a −25° C. solution of triphenylphosphine (TPP, 1.2 equiv) in dry THF was added dropwise diisopropyl azodicarboxylate (DIAD, 1.2 equiv). Ten minutes later, a solution of alcohol 5 in dry THF was added dropwise at the same temperature to form a yellow suspension. After 30 min, the reaction mixture was warmed to 0° C. and then diphenylphosphoryl azide (DPPA, 1.2 equiv) was added dropwise. The reaction mixture was warmed to rt and stirred. After 16 h, the reaction mixture was quenched with H$_2$O and extracted with Et$_2$O three times. The combined ethereal extracts were dried over Na$_2$SO$_4$, filtered, and concentrated under vacuum. The crude product was purified via SiO$_2$ column chromatography using 2% EtOAc/hexanes as eluant to give 6 (>97%) as a light yellow oil. An analytical sample was further purified using preparative TLC to give 6 as a colorless oil.

TLC: 20% EtOAc/hexanes, R$_f$~0.8. $^1$H NMR (400 MHz, CDCl$_3$) δ 5.43-5.28 (m, 2H), 4.59-4.56 (m, 1H), 3.91-3.84 (m, 1H), 3.77-3.69 (m, 1H), 3.54-3.46 (m, 1H), 3.41-3.35 (m, 1H), 3.27 (t, J=6.8 Hz, 2H), 2.10-1.95 (m, 4H), 1.88-1.78 (m, 1H), 1.76-1.68 (m, 1H), 1.65-1.48 (m, 6H), 1.46-1.38 (m, 2H), 1.38-1.24 (m, 14H); $^{13}$C NMR (100 MHz, CDCl$_3$) δ 130.9, 129.0, 99.0, 67.8, 62.4, 51.5, 31.0, 29.9, 29.8, 29.7, 29.6 (2), 29.5, 28.6, 27.4, 26.9, 26.8, 26.4, 25.7, 19.9.

Step E. Synthesis of 15-(tetrahydro-2H-pyran-2-yloxy)pentadec-5(Z)-en-1-amine (7)

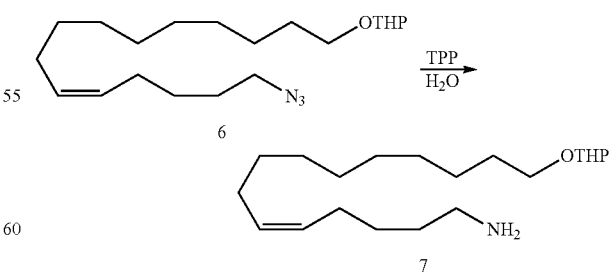

To a rt solution of the above crude azide 6 in THF was added triphenylphosphine (TPP, 1.3 equiv) in one portion. After 2 h, H$_2$O was added and the reaction was stirred at rt. After 12 h, the reaction mixture was diluted with EtOAc followed by brine and the biphasic mixture was extracted with EtOAc three times. The combined organic extracts were dried over Na$_2$SO$_4$, filtered, and concentrated under vacuum. The crude product was triturated in Et$_2$O and filtered through a fritted funnel. The filtrate was concentrated in vacuo and the crude 7 was utilized in the next step without further purification. TLC: 5% MeOH/CH$_2$Cl$_2$, R$_f$~0.1.

Step F. Synthesis of N$^1$-methyl-N$^2$-(15-(tetrahydro-2H-pyran-2-yloxy)pentadec-5(Z)-enyl)oxalamide (9)

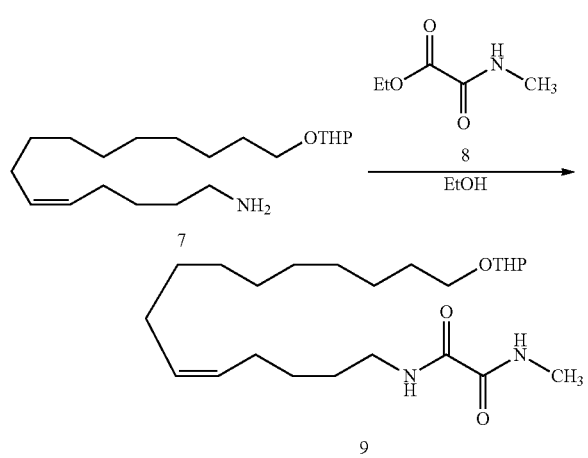

Following literature precedent,[1] the above crude amine 7 and 8 (1.2 equiv) in anhydrous absolute ethanol were heated at 85° C. in a sealed tube. After 15 h, the reaction mixture was concentrated in vacuo and the crude product was purified via SiO$_2$ column chromatography using 25% EtOAc/hexanes to give 9 (70%) as a white solid, mp 69.9-70.2° C.

TLC: 50% EtOAc/hexanes, R$_f$~0.65. $^1$H NMR (500 MHz, CDCl$_3$) δ 7.56-7.46 (br s, 2H), 5.42-5.28 (m, 2H), 4.59-4.56 (m, 1H), 3.91-3.84 (m, 1H), 3.72 (dt, J=9.6, 6.9 Hz, 1H), 3.54-3.46 (m, 1H), 3.37 (dt, J=9.6, 6.7 Hz, 1H), 3.30 (app q, J=6.9 Hz, 2H), 2.91 (d, J=5.5 Hz, 3H), 2.04 (dt, J=7.5, 7.0 Hz, 2H), 1.98 (app q, J=7.0, 2H), 1.88-1.78 (m, 1H), 1.76-1.68 (m, 1H), 1.64-1.47 (m, 7H), 1.44-1.22 (m, 15H); $^{13}$C NMR (125 MHz, CDCl$_3$) δ 160.8, 159.9, 130.9, 129.1, 99.1, 67.9, 62.6, 39.8, 31.0, 29.9(2), 29.8, 29.7(2), 29.5, 29.0, 27.5, 27.1, 26.9, 26.5, 26.4, 25.7, 19.9.

Step G. Synthesis of N$^1$-(15-hydroxypentadec-5(Z)-enyl)-N$^2$-methyloxalamide (10)

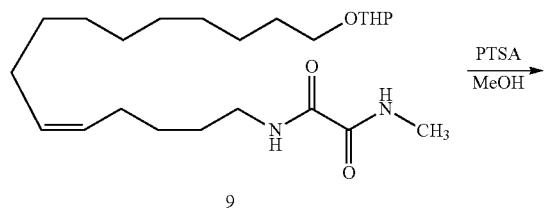

To a solution of 9 in methanol was added p-toluenesulfonic acid (PTSA, 0.07 eqiv). After 2 h, the solvent was evaporated in vacuo and the residue was re-dissolved in EtOAc. Passage of the crude product through a short silical gel pad using EtOAc as eluant gave 10 (>95%) as a white solid, mp 115.4-115.7° C.

TLC: 50% EtOAc/hexanes, R$_f$~0.25. $^1$H NMR (400 MHz, CDCl$_3$) δ 7.45 (br s, 2H), 5.42-5.28 (m, 2H), 3.71-3.55 (m, 2H), 3.31 (app q, J=6.8 Hz, 2H), 2.91 (d, J=5.2 Hz, 3H), 2.12-1.91 (m, 4H), 1.61-1.52 (m, 6H), 1.44-1.23 (m, 12H); $^{13}$C NMR (125 MHz, CDCl$_3$) δ 160.8, 159.9, 130.9, 129.1, 63.3, 39.8, 33.0, 29.8, 29.7, 29.6(2), 29.4, 29.0, 27.4, 27.1, 26.9, 26.4, 25.9.

Example 2

Preparation of Example Compound C41

Step A. Synthesis of N$^1$-(15-bromopentadec-5(Z)-enyl)-N$^2$-methyloxalamide (11)

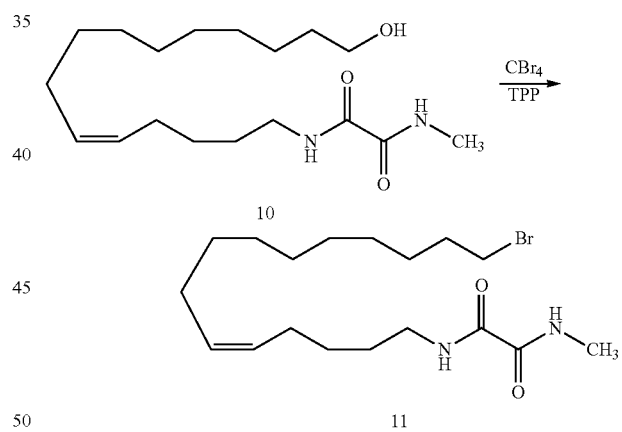

To a solution of TPP (745 mg, 1.2 equiv) in CH$_2$Cl$_2$ (80 mL) under an argon atmosphere was added a solution of common intermediate 10 (740 mg, 2.37 mmol, 1 equiv) in CH$_2$Cl$_2$ (40 mL) followed by carbon tetrabromide (CBr$_4$, 1.2 equiv, 942 mg) in one portion. After 24 h, the reaction mixture was concentrated under vacuum and the residue was purified via silica gel column chromatography using 20-25% EtOAc/hexanes to give 11 (597 mg, 67%) as a white solid, mp 77.5-77.6° C.

TLC: 50% EtOAc/hexanes, R$_f$~0.7. $^1$H NMR (400 MHz, CDCl$_3$) δ 7.45 (br s, 2H), 5.42-5.27 (m, 2H), 3.41 (t, J=6.8 Hz, 2H), 3.31 (app q, J=6.8 Hz, 2H), 2.91 (d, J=5.6 Hz, 3H), 2.09-1.96 (m, 4H), 1.85 (app quintet, J=7.2 Hz, 2H), 1.62-1.52 (m, 2H), 1.47-1.37 (m, 4H), 1.37-1.23 (m, 10H); $^{13}$C NMR (100 MHz, CDCl$_3$) δ

160.8, 159.9, 130.9, 129.1, 39.8, 34.3, 33.0, 29.9, 29.6(2), 29.5, 29.0, 28.9, 28.4, 27.4, 27.1, 26.9, 26.4.

Step B. Synthesis of dimethyl 15-(2-(methylamino)-2-oxoacetamido)pentadec-10(Z)-enylphosphonate (12)

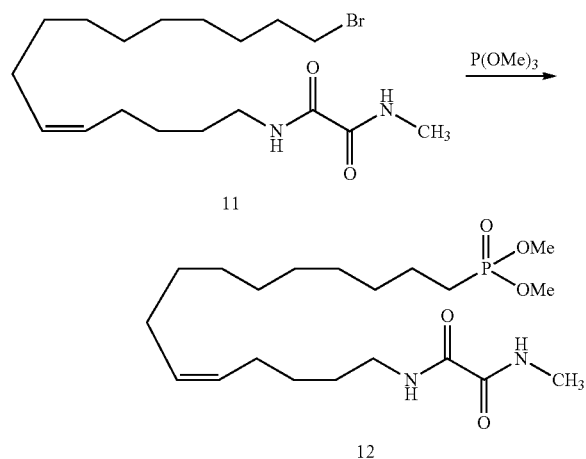

A solution of 11 (375 mg, 1.1 mmol) and trimethyl phosphite [P(OMe)$_3$] (16 mL) in dry THF (16 mL) was heated in a sealed tube at 120° C. After 3 d, the THF was evaporated in vacuo and the P(OMe)$_3$ was distilled off under reduced pressure. The crude 12 (240 mg, 54%) was subjected to the next reaction without further purification. An analytical sample was purified by preparative TLC.

TLC: 50% EtOAc/hexanes, $R_f$=0.2. $^1$H NMR (500 MHz, CDCl$_3$) δ 7.48 (br s, 2H), 5.39-5.26 (m, 2H), 3.72 (d, $J_{P,H}$=10.5 Hz, 6H), 3.30 (app q, J=7.0 Hz, 2H), 2.90 (d, J=5.0 Hz, 3H), 2.04 (app q, J=7.5 Hz, 2H), 1.98 (app q, J=7.5 Hz, 2H), 1.81-1.67 (m, 2H), 1.63-1.51 (m, 4H), 1.43-1.21 (m, 14H); $^{31}$P NMR (202 MHz, CD$_3$OD; rel 85% H$_3$PO$_4$) δ 36.48 (s).

Step C. Synthesis of disodium 15-(2-(methylamino)-2-oxoacetamido)pentadec-10(Z)-enylphosphonate (C41)

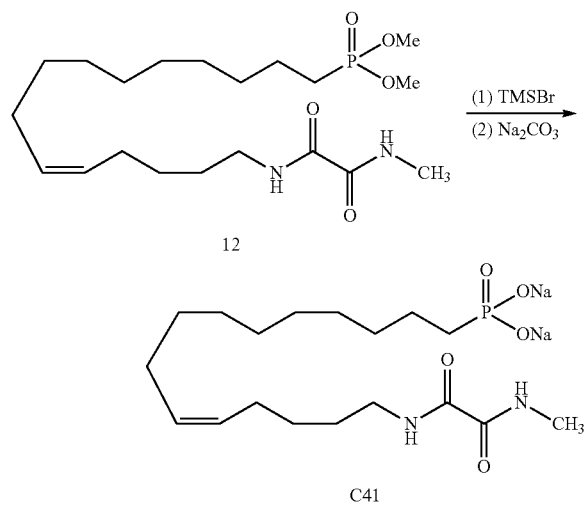

Following literature precedent,[2] TMSBr (10 equiv, 0.5 mL) was added dropwise to a 0° C. solution of 12 (150 mg, 0.371 mmol) in anhydrous CH$_2$Cl$_2$ (10 mL). After 75 min, the reaction was quenched with methanol (5 mL), concentrated in vacuo, and the residue was triturated with CH$_2$Cl$_2$ (2×10 mL). The residue, mp 130.6-130.7° C., was dissolved in aq. Na$_2$CO$_3$ solution (0.01 M, pH 10). Bio-Rad™ SM-2 Bio-Beads (20-50 mesh, 5 g) were added to the solution. After gently stirring for 30 min, the beads were collected on a fritted funnel and washed with water (20 mL). Methanol was then used to strip C41 from the Bio-Beads. Evaporation of the methanol afforded C41 (48 mg, 30%) as a white powder, mp 240° C. (dec).

Free acid of C41: $^1$H NMR (500 MHz, CD$_3$OD) δ 8.58 (br s, 3H), 5.44-5.24 (m, 2H), 3.26 (app q, J=6.5 Hz, 2H), 2.82 (s, 1H), 2.81 (s, 2H), 2.12-1.98 (m, 4H), 1.88-1.72 (m, 2H), 1.71-1.50 (m, 4H), 1.47-1.24 (m, 14H); $^{31}$P NMR (202 MHz, CD$_3$OD; rel 85% H$_3$PO$_4$) δ 31.37 (s).

C41: $^1$H NMR (500 MHz, CD$_3$OD) δ 5.43-5.28 (m, 2H), 3.26 (t, J=7.0 Hz, 2H), 2.82 (s, 3H), 2.14-1.95 (m, 4H), 1.88-1.71 (m, 2H), 1.69-1.42 (m, 4H), 1.42-1.24 (m, 14H).

Example 2A

Preparation of Example Compounds C52 and C53

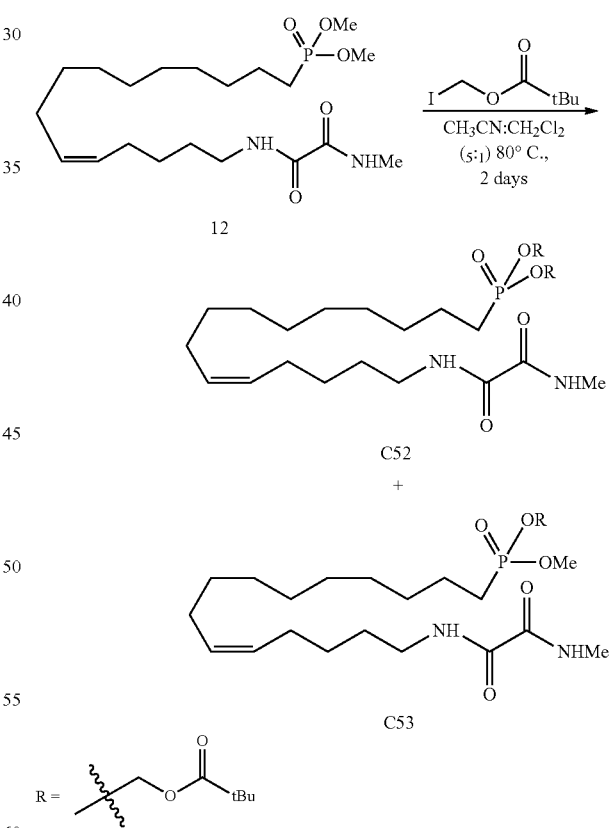

To a stirring, rt solution of dimethyl phosphonate 12 (1.0 mmol, 0.418 g) in dry CH$_3$CN (10 mL) and CH$_2$Cl$_2$ (2 mL) under an argon atmosphere was added pivaloyloxymethyl iodide (POM-I; purchased from Enamine LLC, Princeton Corporate Plaza, 7 Deer Park Drive, Ste. M-3, Monmouth Jct., N.J. 08852 USA) (5.0 mmol, 0.76 mL). After 2 days, most the starting phosphonate was consumed (TLC analysis: 5% MeOH/CH$_2$Cl$_2$). The volatiles were evaporated in vacuo and the crude product was purified by SiO$_2$ flash column chromatography using a gradient of 1-2% MeOH in CH$_2$Cl$_2$ to give pure mono-POM ester C53 (20 mg, 4%) as an oil and di-POM ester C52 with some impurities. A second purification using preparative TLC (5% MeOH/CH$_2$Cl$_2$) furnished pure di-POM ester C52 (21 mg, 3%) as an oil.

C52. TLC: R$_f$-0.5, 5% MeOH/CH$_2$Cl$_2$; $^1$H NMR (400 MHz, CDCl$_3$) δ 7.46 (br s, 2H), 5.64 (d, J$_{H-P}$=13.1 Hz, 4H), 5.40-5.23 (m, 2H), 3.28 (app q, J=7.0 Hz, 2H), 2.88 (d, J=5.2 Hz, 3H), 2.02 (app q, J=6.9 Hz, 2H), 1.97 (app q, J=6.9 Hz, 2H), 1.84-1.74 (m, 2H), 1.64-1.49 (m, 4H), 1.40-1.17 (m, 14H), 1.21 (s, 18H); $^{13}$C NMR (101 MHz, CDCl$_3$) δ 176.86, 160.53, 159.64, 130.57, 128.83, 81.24 (d, $^2J_{C-O-P}$=6.2 Hz), 39.52, 38.70, 30.40 (d, $^2J_{C-C-P}$=18.0 Hz), 29.64, 29.40, 29.27, 29.21, 29.02 ($^4J_{C-P}$=1.4 Hz), 28.78, 27.20, 26.84, 26.82, 26.65, 26.23 (d, $^1J_{C-P}$=84.0 Hz), 26.12, 21.91 (d, $^3J_{C-P}$=5.4 Hz).

C53. TLC: R$_f$-0.4, 5% MeOH/CH$_2$Cl$_2$; $^1$H NMR (500 MHz, CDCl$_3$) δ 7.48 (br s, 2H), 5.68 (d, J$_{H-P}$=13.2 Hz, 2H), 5.43-5.27 (m, 2H), 3.74 (d, J$_{H-P}$=11.2 Hz, 3H), 3.32 (app q, J=6.9 Hz, 2H), 2.92 (d, J=5.2 Hz, 3H), 2.06 (app q, J=6.9 Hz, 2H), 2.00 (app q, J=6.9 Hz, 2H), 1.83-1.76 (m, 2H), 1.64-1.51 (m, 4H), 1.44-1.20 (m, 14H), 1.21 (s, 9H); $^{13}$C NMR (101 MHz, CDCl$_3$) δ 177.00, 160.55, 159.67, 130.59, 128.84, 81.66 (d, $^2J_{C-O-P}$=6.0 Hz), 51.81 (d, $^2J_{C-O-P}$=7.2 Hz), 39.53, 38.72, 30.49 (d, $^2J_{C-C-P}$=17.5 Hz), 29.66, 29.42, 29.28, 29.22, 29.04 (d, $^4J_{C-P}$=1.3 Hz), 28.79, 27.20, 26.90, 26.83, 26.66, 25.83 (d, $^1J_{C-P}$=139.4 Hz), 26.14, 22.10 (d, $^3J_{C-P}$=5.4 Hz).

Example 3

Preparation of Example Compound C38

Step A. Synthesis of N$^1$-(15-cyanopentadec-5(Z)-enyl)-N$^2$-methyloxalamide (13)

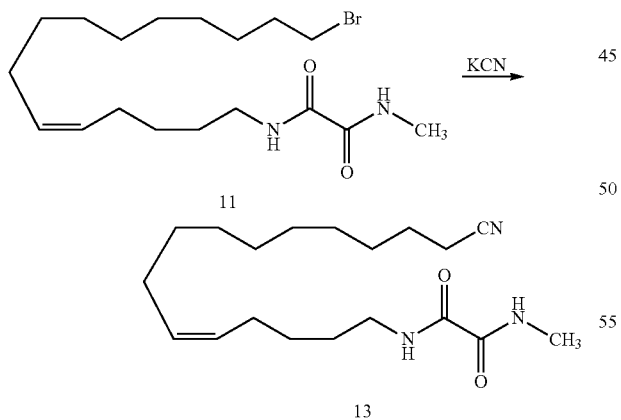

To a solution of bromide 11 (550 mg, 1.47 mmol) in DMSO (30 mL) was added KCN (500 mg, 5 equiv) in one portion. After 24 h at rt, the reaction mixture was diluted with water (60 mL) and extracted with EtOAc (20 mL×3). The combined organic extracts were washed with water (25 mL×2) and then with brine (30 mL). The extracts were dried over anhydrous Na$_2$SO$_4$, filtered, and then concentrated in vacuo. The residue was purified via SiO$_2$ column chromatography using 20-25% EtOAc/hexanes to give 13 (490 mg, 99%) as a white powder, mp 88.8-88.9° C.

TLC: 50% EtOAc/hexanes, R$_f$-0.55. $^1$H NMR (400 MHz, CDCl$_3$) δ 7.43 (br s, 2H), 5.44-5.23 (m, 2H), 3.31 (app q, J=6.8 Hz, 2H), 2.91 (d, J=5.2 Hz, 3H), 2.34 (t, J=7.2 Hz, 2H), 2.09-1.96 (m, 4H), 1.71-1.61 (m, 2H), 1.61-1.49 (m, 4H), 1.49-1.36 (m, 4H), 1.36-1.22 (m, 8H); $^{13}$C NMR (100 MHz, CDCl$_3$) δ 160.8, 159.9, 130.8, 129.1, 120.1, 39.8, 29.8, 29.6, 29.5, 29.4, 29.0, 28.9, 28.8, 27.4, 27.1, 26.9, 26.4, 25.6, 17.3.

Step B. Synthesis of N$^1$-16-amino-16-(hydroxyimino)hexadec-5(Z)-enyl-N$^2$-methyloxalamide (14)

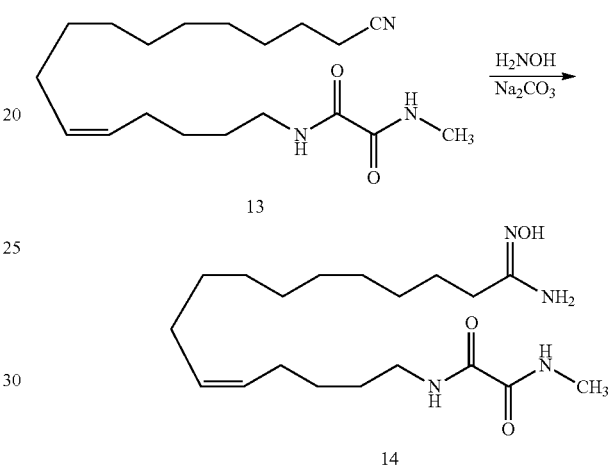

Following literature precedent,[3] a solution of nitrile 13 (100 mg, 0.311 mmol), NH$_2$OH.HCl (108 mg, 5 equiv), and Na$_2$CO$_3$ (181 mg, 5.5 equiv) in anhydrous methanol (2 mL) was heated in a sealed tube at 84° C. After 2 d, the reaction mixture was cooled to rt, filtered, and concentrated in vacuo. The residue was triturated with EtOAc (60 mL×3) and then water (70 mL). The white solid residue (76 mg, 69%) was used in the next reaction without further purification. An analytical sample was purified by preparative TLC (5% MeOH/CH$_2$Cl$_2$, R$_f$-0.35), mp 118.1-118.5° C.

$^1$H NMR (400 MHz, CD$_3$OD) δ 5.35 (td, J=5.9, 4.6 Hz, 2H), 3.25 (t, J=7.1 Hz, 2H), 2.82 (s, 3H), 2.12-1.98 (m, 6H), 1.90 (s, 1H), 1.56 (app quintet, J=7.3 Hz, 4H), 1.44-1.26 (m, 16H); $^{13}$C NMR (100 MHz, CD$_3$OD) δ 161.2, 160.4, 156.5, 130.1, 129.1, 39.19, 30.61, 29.63, 29.43, 29.38, 29.25, 29.12, 28.97, 28.67, 27.14, 26.94, 26.85, 26.58, 25.08.

Step C. Synthesis of N$^1$-methyl-N$^2$-(15-(2-oxido-3H-1,2,3,5-oxathiadiazol-4-yl)pentadec-5(Z)-en-1-yl)oxalamide (C38)

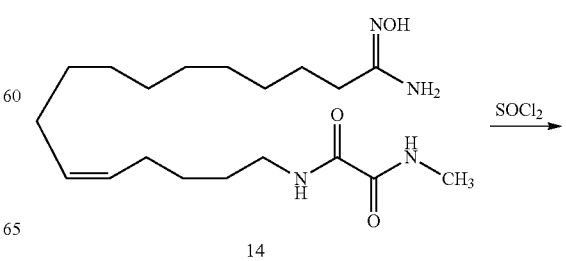

-continued

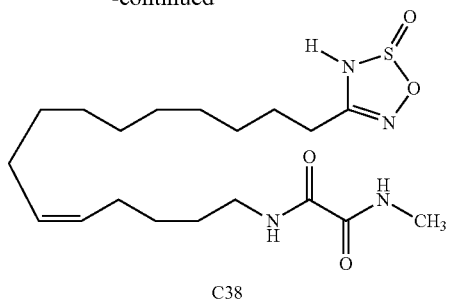

C38

Following literature precedent,[3] pyridine (43.6 μL, 2.6 equiv) followed by a solution of SOCl₂ (20 μL, 1.3 equiv) in CH₂Cl₂ (1 mL) were added to a 0° C. solution of 14 (74 mg, 0.21 mmol) in THF (4 mL). After 1 hr 40 min, all volatiles were removed in vacuo and the residue was diluted with water (10 mL), and extracted with EtOAc (15 mL×5). The combined organic extracts were dried over Na₂SO₄, filtered, concentrated and purified by preparative TLC (10% MeOH/CH₂Cl₂) to give C38 (55 mg, 63%) as a white solid, mp 92.7-92.9° C.

TLC: 5% MeOH/CH₂Cl₂, $R_f$~0.6. ¹H NMR (500 MHz, CDCl₃) δ 8.38 (s, 1H), 7.50 (s, 2H), 5.41-5.28 (m, 2H), 3.41-3.21 (m, 2H), 2.91 (d, J=5.2 Hz, 3H), 2.62 (t, J=7.7 Hz, 2H), 2.06 (app q, J=7.0 Hz, 4H), 2.01 (app q, J=7.0 Hz, 4H), 1.69 (app quintet, J=7.7 Hz, 2H), 1.63-1.55 (m, 3H), 1.46-1.13 (m, 9H); ¹³C NMR (100 MHz, CDCl₃) δ 160.72, 159.91, 152.89, 130.89, 129.19, 39.95, 29.43, 29.32, 29.21, 29.12, 29.04, 28.97, 28.88, 27.08 (2), 26.88, 26.58, 26.53, 23.95.

Example 4

Preparation of Example Compound C42

Step A. Synthesis of W-(15-iodopentadec-5(Z)-en-1-yl)-N²-methyloxalamide (15)

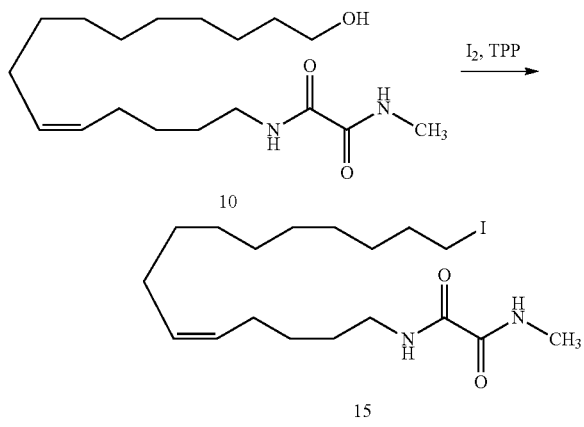

To a solution of 10 (1.80 g, 5.76 mmol), TPP (1.66 g, 1.1 equiv) and imidazole (784 mg, 2 equiv) in dry THF (180 mL) at 0° C. was added I₂ (1.75 g, 1.2 equiv). The reaction was allowed to warm to rt and stirred. After 15 h, the reaction was quenched with sat. NaHSO₃ solution and washed twice with water. The aqueous phase was re-extracted with EtOAc (20 mL×2). The combined organic extracts were dried over Na₂SO₄, filtered, and concentrated under vacuum. The residue was purified via SiO₂ column chromatography using 20-25% EtOAc/hexanes to give 15 (1.77 g, 70%) as a white solid, mp 81.7° C.

TLC: 50% EtOAc/hexanes, $R_f$~0.65. ¹H NMR (CDCl₃, 500 MHz) δ 7.43 (br s, 2H), 5.42-5.27 (m, 2H), 3.31 (app q, J=6.9 Hz, 2H), 3.19 (t, J=7.0 Hz, 2H), 2.91 (d, J=5.2 Hz, 3H), 2.05 (dt, J=7.5, 7.0 Hz, 2H), 2.00 (app q, J=7.0 Hz, 2H), 1.82 (app quintet, J=7.2 Hz, 2H), 1.63-1.48 (m, 2H), 1.44-1.22 (m, 14H); ¹³C NMR (125 MHz, CDCl₃) δ 160.81, 159.94, 130.87, 129.12, 39.82, 33.80, 30.75, 29.93, 29.67, 29.63, 29.50, 29.06, 28.78, 27.48, 27.11, 26.94, 26.44, 7.68.

Step B. Synthesis of Sodium 15-(2-(methylamino)-2-oxoacetamido)pentadec-10(Z)-en-1-sulfonate (C42)

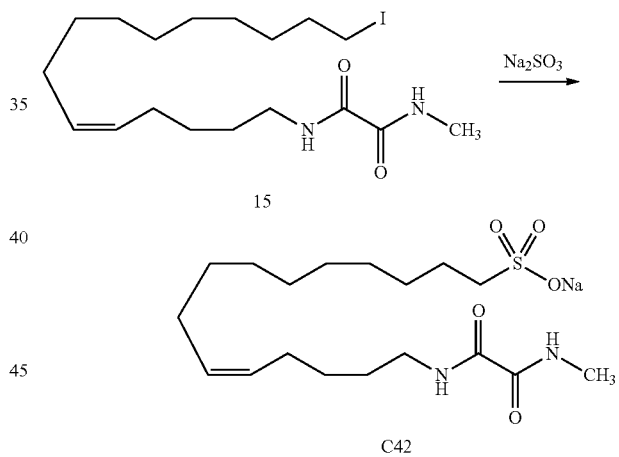

Iodide 15 (200 mg, 0.46 mmol), Na₂SO₃ (231 mg, 4 equiv), ethanol (95%, 3 mL), cyclohexene (0.93 mL, 20 equiv) and water (1.5 mL) were heated at 85° C. in a sealed tube. After 4 d, the reaction mixture was cooled to rt, concentrated under vacuum, dissolved in H₂O, and isolated by adsorption onto Bio-Rad SM-2 Bio-Beads as described for C41 to give C42 (51 mg, 27%) as an off-white solid, mp 202-210° C. (dec).

¹H NMR (500 MHz, DMSO-d₆) δ 8.86-8.55 (m, 2H), 5.45-5.18 (m, 2H), 3.18-2.99 (m, 2H), 2.65 (d, J=5.9 Hz, 3H), 2.34 (t, J=8.0 Hz, 2H), 2.05-1.87 (m, 4H), 1.60-1.35 (m, 4H), 1.35-1.10 (m, 14H); ¹³C NMR (100 MHz, DMSO-d₆) δ 161.26, 160.51, 130.34, 129.85, 52.20 (2), 39.23, 29.81, 29.70, 29.58, 29.59, 29.32, 29.10, 28.98, 27.28, 27.07, 26.94, 25.78.

Example 5

Preparation of Example Compound C43

Synthesis of $N^1$-(15-((2-acetamidobenzo[d]thiazol-7-yl)oxy)pentadec-5(Z)-en-1-yl)-$N^2$-methyloxalamide (C43)

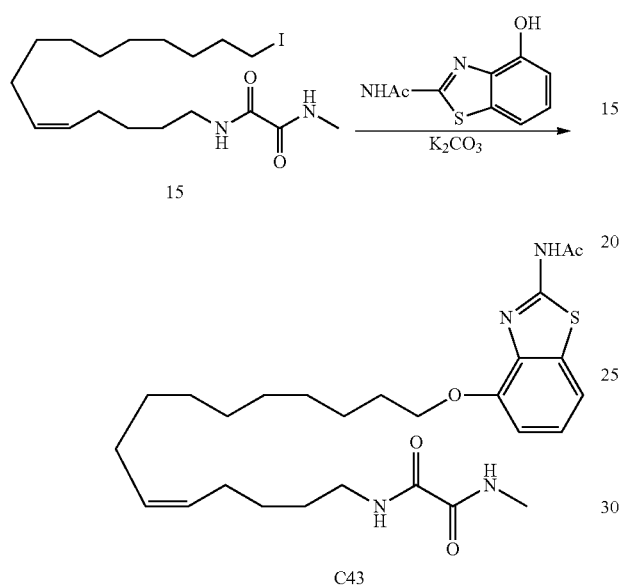

A sealed tube containing iodide 15 (200 mg, 0.458 mmol), N-(4-hydroxybenzo[d]thiazol-2-yl)acetamide[4] (122 mg, 1 equiv), and $K_2CO_3$ (95 mg, 1.5 equiv) was heated at 85° C. After 6 h, the reaction was cooled to rt, diluted with EtOAc (15 mL) and water (15 mL), and extracted with EtOAc (15 mL×3). The combined organic extracts were dried over $Na_2SO_4$, filtered, and concentrated under vacuum. The residue was purified on a Teledyne Isco Combiflash® RF chromatographic system (1.2 g $SiO_2$ column eluted with 50-60% EtOAc/hexane) to give C43 (68 mg, 29%) as a brown solid. The brown solid was dissolved in EtOH (1 mL) and sonicated at rt for 5 mins. Analog C43 precipitated as a white solid, upon standing and drying under high vacuum.

TLC: 50% EtOAc/hexanes, $R_f$~0.2. $^1$H NMR (CDCl$_3$, 500 MHz) δ 11.33 (br s, 1H), 7.85 (br s, 1H), 7.59 (br s, 1H), 7.40 (d, J=8.0 Hz,1H), 7.24 (app t, J=8.0 Hz,1H), 6.89 (d, J=8.0 Hz, 1H), 5.40-5.26 (m, 2H), 4.13 (t, J=6.5 Hz, 2H), 3.32 (app q, J=7.0 Hz, 2H), 2.89 (d, J=5.0 Hz, 3H), 2.24 (s, 3H), 2.04 (app q, J=7.0 Hz, 2H), 1.97 (app q, J=7.0 Hz, 2H), 1.88-1.79 (m, 2H), 1.62-1.51 (m, 2H), 1.49-1.34 (m, 4H), 1.34-1.17 (m, 10H); $^{13}$C NMR (125 MHz, CDCl$_3$) δ 169.20, 160.87, 160.15, 158.24, 151.58, 138.33, 133.73, 130.96, 129.07, 125.00, 113.63, 108.24, 69.00, 39.85, 29.83, 29.80, 29.70, 29.65, 29.50, 29.48, 29.02, 27.44, 27.07, 26.90, 26.53, 26.35, 23.59.

Example 6

Preparation of Example Compound C48

Step A.

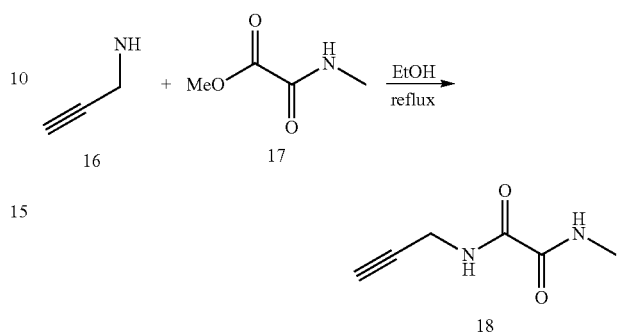

A solution of 16 (12 mmol) and 17 (10 mmol) in absolute EtOH (100 mL) was heated under reflux. After 12 h, the reaction mixture was cooled to rt and concentrated in vacuo to approximately 20% of the original volume when 18 began to precipitate as an off-white solid. The solid was collected by filtration and used in the next step without further purification.

TLC: EtOAc/hexanes (2:1), $R_f$~0.5; $^1$H NMR (400 MHz, CDCl$_3$) δ 2.26 (s, 1H), 2.90 (d, J=5.2 Hz, 3H), 4.06-4.13 (m, 2H), 7.44 (br s, 1H), 7.68 (br s, 1H).

Step B.

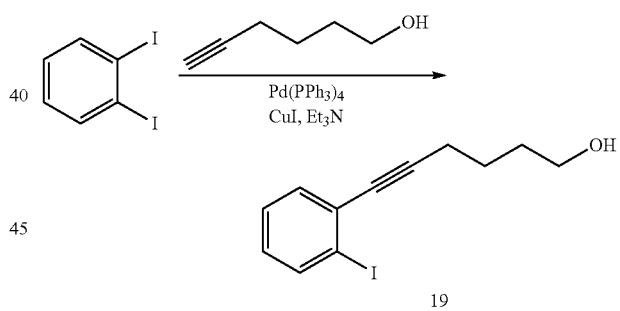

To a solution of Pd(PPh$_3$)$_4$ (3 mol %, 350 mg) and CuI (5 mol %, 100 mg) in Et$_3$N (40 mL) under an argon atmosphere was added a solution of 1,2-diiodobenzene (10 mmol, 3.3 g) and 5-hexyne-1-ol (10 mmol, 980 mg) in Et$_3$N (10 mL). The reaction was heated to 60° C. for 12 h, then cooled to rt and filtered through a pad of Celite®. The filtrate was concentrated in vacuo and the residue was purified using a Teledyne Isco Combiflash® RF chromatographic system [40 g SiO$_2$ column eluted with EtOAc/hexanes (1:2)] to give 19 (1.5 g, 50%) as a pale yellow oil.

TLC: EtOAc/hexanes (1:2), $R_f$~0.2. $^1$H NMR (500 MHz, CDCl$_3$) δ 1.73-1.81 (m, 2H), 1.82-1.88 (m, 2H), 2.55 (t, J=7.0 Hz, 2H), 3.76 (t, J=7.0 Hz, 2H), 6.98 (dd, J=7.0, 8.0 Hz, 1H), 7.29 (dd, J=7.0, 8.0 Hz, 1H), 7.42 (d, J=7.5 Hz, 1H), 7.84 (d, J=8.0 Hz, 1H).

Step C.

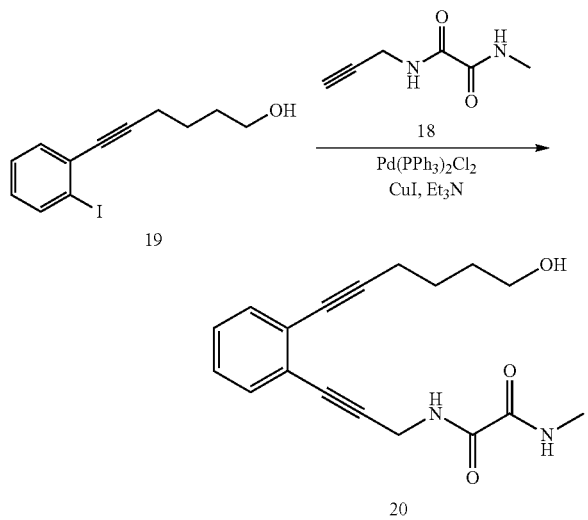

Et₃N (16.6 mmol, 2.3 mL) and alcohol 19 (1.66 mmol, 500 mg) were added sequentially to a solution of 18 (1.66 mmol, 232 mg), Pd(PPh₃)₂Cl₂ (3 mol %, 35 mg) and CuI (5 mol %, 16 mg) in dry CH₃CN (15 mL) under an argon atmosphere. After heating at 50° C. for 12 h, the reaction mixture was cooled to rt and filtered through a Celite® pad. The filtrate was concentrated in vacuo and the residue was purified using a Teledyne Isco Combiflashe RF chromatographic system [40 g SiO₂ column eluted with EtOAc/hexanes (2:1)] to afford 20 (362 mg, 70%) as a pale yellow oil.

TLC: EtOAc/hexanes (2:1), $R_f$~0.15. ¹H NMR (500 MHz, CDCl₃) δ 1.68-1.78 (m, 2H) 1.80-1.88 (m, 2H), 2.53 (t, J=7.0 Hz, 2H), 2.92 (d, J=5.0 Hz, 3H), 3.76 (t, J=6.5 Hz, 2H), 4.40 (d, J=6.0 Hz, 2H), 7.18-7.28 (m, 2H), 7.36-7.44 (m, 2H), 7.62 (br s, 1H), 8.24 (br s, 1H).

Step D.

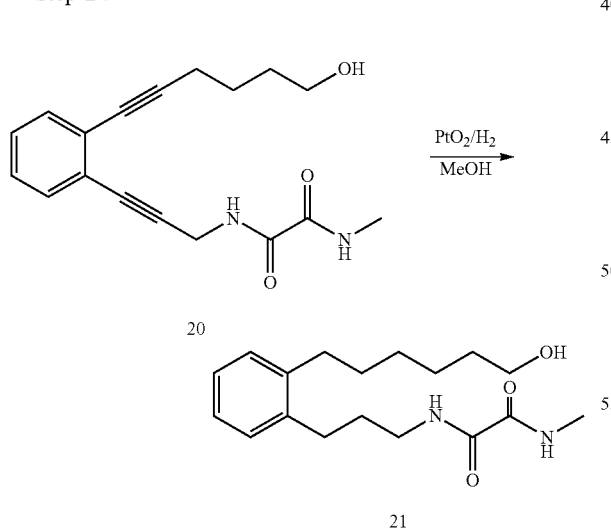

A mixture of diyne 20 (100 mg) and PtO₂ (10 mg) in dry MeOH (10 mL) was shaken in a Parr hydrogenation apparatus under a H₂ atmosphere (50 psi). After 12 h, the reaction mixture was filtered through a Celite® pad and the filtrate was concentrated in vacuo to give crude 21 as a white solid that was used in the next step without further purification.

Step E.

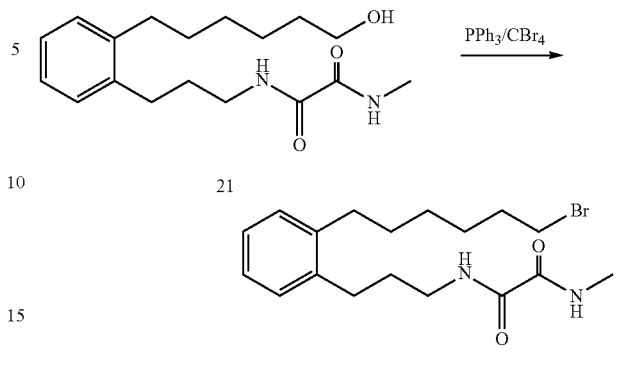

PPh₃ (0.38 mmol, 100 mg) was added in one portion to a 0° C. solution of 21 (0.32 mmol, 100 mg) and CBr₄ (0.48 mmol, 160 mg) in CH₂Cl₂ (5 mL). After stirring at rt for 12 h, the solvent was evaporated in vacuo and the residue was purified using a Teledyne Isco Combiflash® RF chromatographic system [24 g SiO₂ column eluted with EtOAc/hexanes (2:1)] to give bromide 22 (98 mg, 80%) as a white solid.

TLC: EtOAc/hexanes (4:1), $R_f$~0.7. ¹H NMR (400 MHz, CDCl₃) δ 1.35-1.50 (m, 4H), 1.54-1.62 (m, 2H), 1.80-1.90 (m, 4H), 2.58 (dd, J=8.0, 8.0 Hz, 2H), 2.65 (dd, J=8.0, 8.0 Hz, 2H), 2.91 (d, J=5.2 Hz, 3H), 3.38 (dd, J=7.2, 7.2 Hz, 2H), 3.40 (J=7.2, 7.2 Hz, 2H), 7.10-7.16 (m, 4H), 7.42 (br s, 1H), 7.47 (br s, 1H); ¹³C NMR (100 MHz, CDCl₃) δ 26.4, 28.3, 29.0, 30.0, 30.8, 31.2, 32.7, 32.9, 34.2, 39.7, 126.3, 126.5, 129.3, 129.5, 138.8, 140.4, 160.0, 160.7.

Step F.

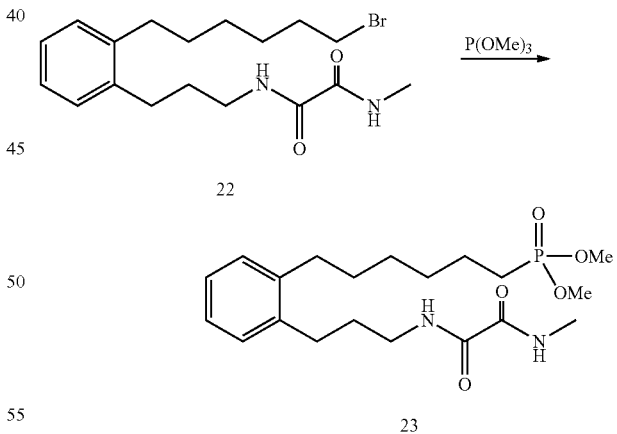

A mixture of bromide 22 (0.54 mmol, 200 mg) and P(OMe)₃ (16.2 mmol, 1.9 mL) was heated under reflux in a sealed tube for 48 h, then cooled to rt and the excess P(OMe)₃ was removed under vacuum. The residue was purified by PTLC using EtOAc/hexanes/MeOH (2:1:0.3) to give dimethyl phosphonate 23 (195 mg, 88%) as a white solid.

TLC: EtOAc/hexanes/MeOH (2:1:0.3), $R_f$~0.3. ¹H NMR (400 MHz, CDCl₃) δ 1.32-1.42 (m, 4H), 1.50-1.76 (m, 6H), 1.78-1.88 (m, 2H), 2.53-2.58 (m, 2H), 2.60-2.65

(m, 2H), 2.89 (d, J=5.2 Hz, 3H), 3.36 (dd, J=6.8, 6.8 Hz, 2H), 3.71 (d, J$_{P-H}$=10.4 Hz, 6H), 7.08-7.12 (m, 4H), 7.56 (br s, 2H).

Step G.

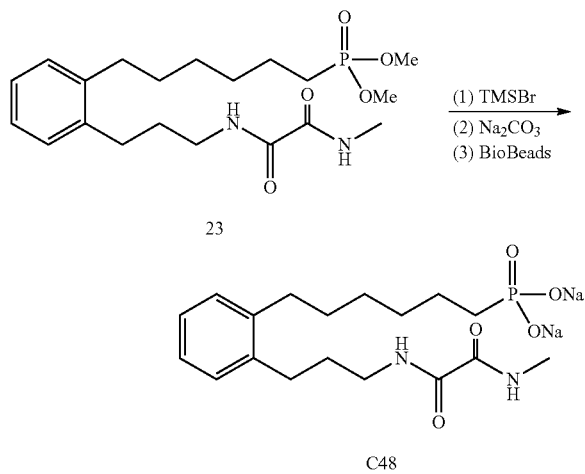

TMSBr (2 mmol, 260 uL) was added dropwise to a solution of crude diester 23 (0.19 mmol, 80 mg) in dry CH$_2$Cl$_2$ (3 mL) under an argon atmosphere. After 3 h, the reaction was quenched with MeOH (2 mL). After stirring for another 1 h, all volatiles were removed in vacuo and aq. Na$_2$CO$_3$ solution (0.5 M) was added to reach pH~10. Bio-Rad™ SM-2 Bio-Beads (20-50 mesh, 5 g) were added to the solution. After gently stirring for 30 min, the beads were collected on a fritted funnel and washed with water (20 mL). Methanol and EtOAc were then used to strip compound from the Bio-Beads. Evaporation of the organic washes gave C48 (37 mg, 45%) as an off-white solid, mp>300° C. (dec).

$^1$H NMR (400 MHz, CD$_3$OD) δ 1.34-1.66 (m, 10H), 1.74-1.84 (m, 2H), 2.58 (dd, J=8.0, 8.0 Hz, 2H), 2.63 (dd, J=8.0, 8.0 Hz, 2H), 2.81 (s, 3H), 3.26-3.34 (m, 2H), 7.02-7.12 (m, 4H); $^{13}$C NMR (100 MHz, CD$_3$OD) δ 24.4 (d, J$_{C-P}$=4.0 Hz), 24.9, 29.3, 29.5, 30.5, 30.6, 31.3, 31.6 (d, J$_{C-P}$=17.4 Hz), 32.4, 39.1, 125.4, 125.6, 128.7, 129.0, 138.9, 140.3, 160.3, 161.0; $^{31}$P NMR (162 MHz, CD$_3$OD; ref 85% H$_3$PO$_4$) δ 24.4.

Example 7

Preparation of Example Compound C49
Step A.

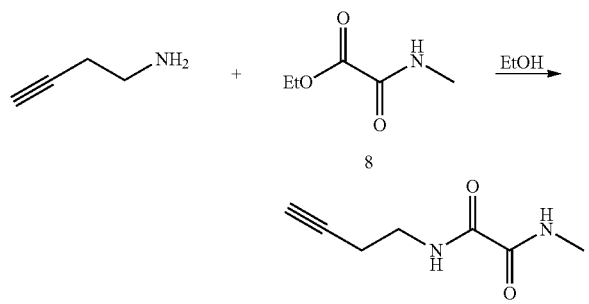

Crude 24 was prepared closely following the procedure used above to generate homolog 18 and was used without further purification.

Step B.

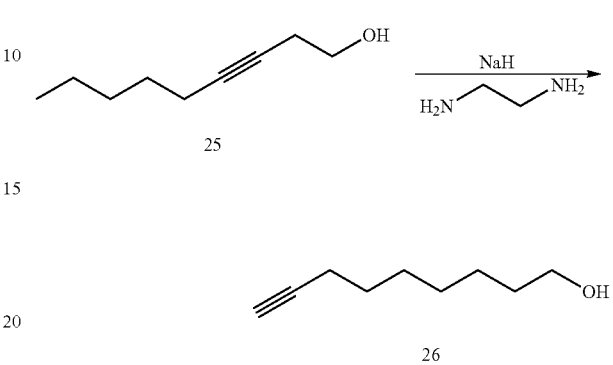

NaH (60 wt % in mineral oil, 714 mmol, 2.85 g) was added in one portion to ethylenediamine (35 mL) at 0° C. under an argon atmosphere. The reaction was stirred at rt for 1 h then at 60° C. for 1 h. After cooling to rt, alcohol 25 (17.85 mmol, 2.84 mL) was added dropwise. Upon complete addition, the reaction mixture was reheated to 60° C. After 1 h, the reaction mixture was cooled to 0° C. and quenched with 1 N HCl. The organic layer was extracted with ether (3×100 mL). The combined ethereal extracts were concentrated in vacuo and the residue was purified using a Teledyne Isco Combiflash® RF chromatographic system [40 g SiO$_2$ column eluted with EtOAc/hexanes (1:5)] to give 26 (1.4 g, 56%) as a light yellow oil.

Step C.

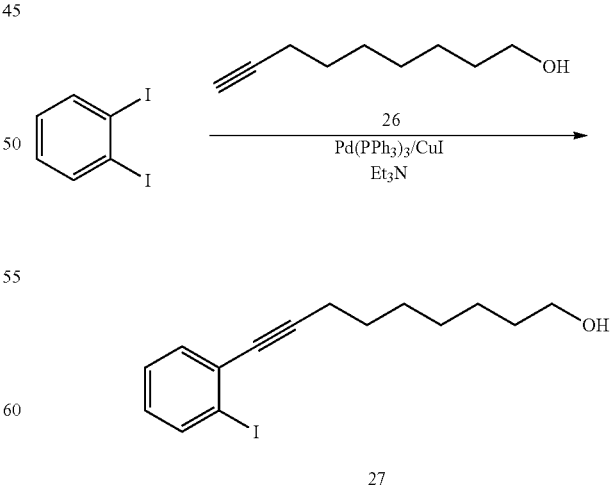

The cross-coupling to generate 27 was conducted as described for the synthesis of 19.

Step D.

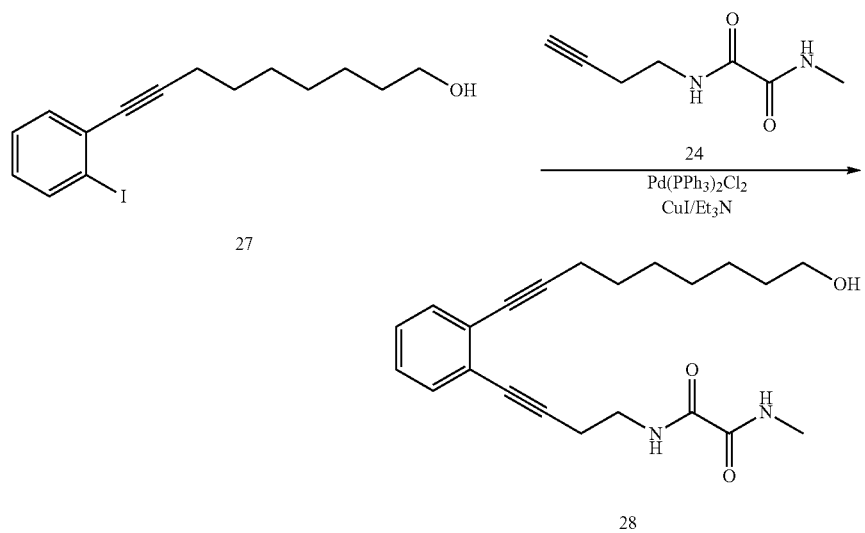

Following the procedure used to prepare 20, iodide 27 and acetylene 24 were transformed into 28, obtained as a pale yellow solid.

TLC: EtOAc/hexanes (2:1), $R_f$~0.1. $^1$H NMR (400 MHz, CDCl$_3$) δ 1.32-1.42 (m, 4H), 1.46-1.66 (m, 6H), 2.46 (t, J=6.8 Hz, 2H), 2.72 (t, J=6.8 Hz, 2H), 2.90 (d, J=5.2 Hz, 3H), 3.58 (dd, J=5.2, 13.2 Hz, 2H), 3.64 (t, J=6.4 Hz, 2H), 7.15-7.22 (m, 2H), 7.34-7.40 (m, 2H), 7.46 (br s, 1H), 7.90 (br s , 1H).

Step E.

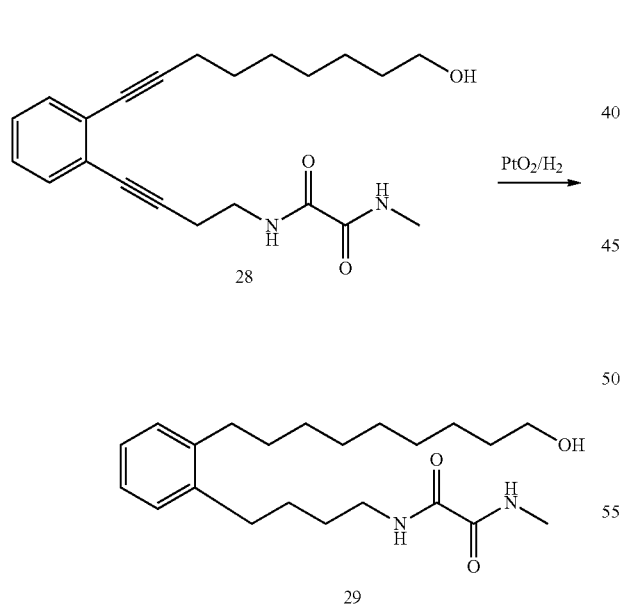

Following the procedure used to prepare 21, diyne 28 was transformed into 29, obtained as a white solid.

TLC: EtOAc/hexanes (2:1), $R_f$~0.15. $^1$H NMR (400 MHz, CDCl$_3$) δ 1.25-1.40 (m, 10H), 1.50-1.65 (m, 8H), 2.54-2.59 (m, 2H), 2.60-2.65 (m, 2H), 2.90 (d, J=5.2 Hz, 3H), 3.30-3.38 (m, 2H), 3.60-3.68 (m, 2H), 7.08-7.14 (m, 4H), 7.45 (br s, 2H).

Step F.

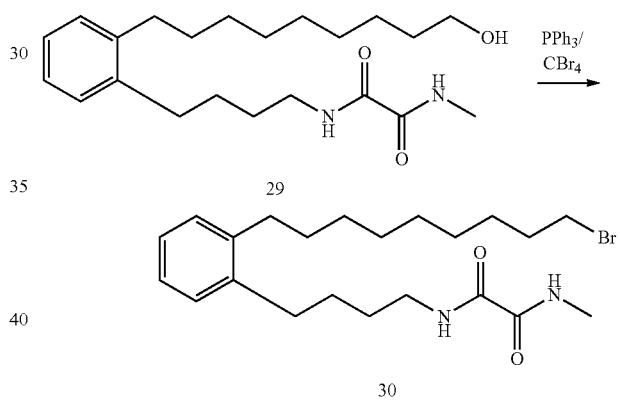

Following the procedure used to prepare 22, alcohol 29 was transformed into 30, obtained as a white solid.

TLC: EtOAc/hexanes (2:1), $R_f$~0.75. $^1$H NMR (400 MHz, CDCl$_3$) δ 1.22-1.48 (m, 12H), 1.50-1.70 (m, 6H), 1.80-1.90 (m, 2H), 2.52-2.68 (m, 4H), 2.89 (d, J=4.8 Hz, 3H), 3.26-3.46 (m, 4H), 7.08-7.16 (m, 4H), 7.53 (br s, 2H); $^{13}$C NMR (100 MHz, CDCl$_3$) δ 26.4, 28.4, 28.6, 29.0, 29.5, 29.6, 29.7, 29.9, 31.5, 32.3, 32.9, 33.0, 34.3, 39.8, 126.0, 126.2, 129.3, 129.4, 139.7, 140.7, 159.9, 160.8.

Step G.

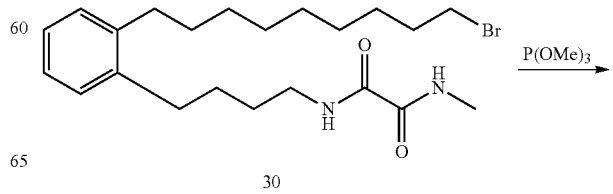

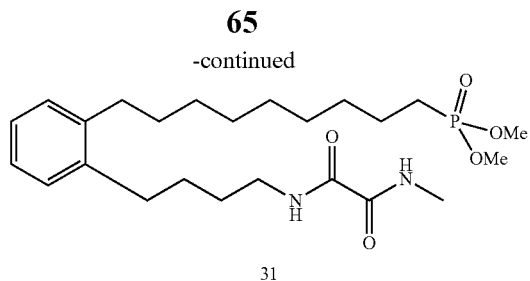

31

Following the procedure used to prepare 23, bromide 30 was transformed into 31, obtained as a white solid.

TLC: EtOAc/hexanes/MeOH (1:1:0.2), $R_f$~0.2. $^1$H NMR (400 MHz, CDCl$_3$) δ 1.20-1.80 (m, 20H), 2.56-2.70 (m, 4H), 2.93 (s, 3H), 3.30-3.42 (m, 2H), 3.76 (d, $J_{P-H}$=10.0 Hz, 6H), 7.08-7.18 (m, 4H), 7.52 (br s, 2H).

Step H.

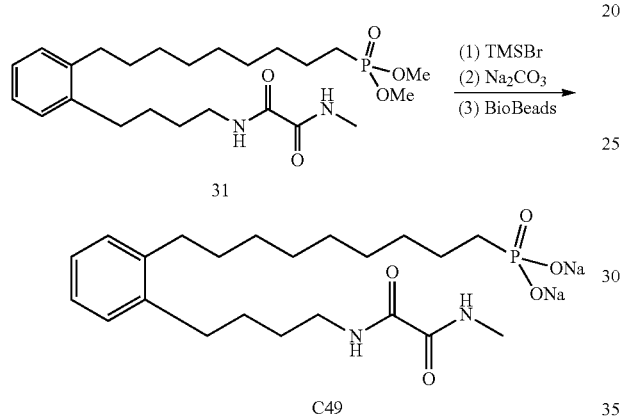

Following the procedure used to prepare C48, dimethyl phosphonate 31 was converted into disodium salt C49, obtained as a white solid, mp>300° C. (dec).

$^1$H NMR (400 MHz, CD$_3$OD) δ 1.25-1.40 (m, 10H), 1.45-1.65 (m, 10H), 2.56-2.66 (m, 4H), 2.80 (s, 3H), 3.25-3.30 (m, 2H), 7.02-7.12 (m, 4H); $^{13}$C NMR (100 MHz, CD$_3$OD) δ 24.1 (d, $J_{C-P}$=4.2 Hz), 24.8, 28.4, 28.7, 28.8, 29.2, 29.3, 29.4, 30.1, 31.3, 31.4 (d, $J_{C-P}$=17.4 Hz), 31.8, 32.2, 38.9, 125.4, 125.5, 128.8, 128.9, 139.5, 140.1, 160.2, 161.0; $^{31}$P NMR (162 MHz, CD$_3$OD) d 24.6.

Example 8

Preparation of Example Compound C50

Synthesis of N$^1$-(16-phenylsulfonamido-16-oxo-hexadec-5(Z)-en-1-yl)-N$^2$-methyloxalamide C50

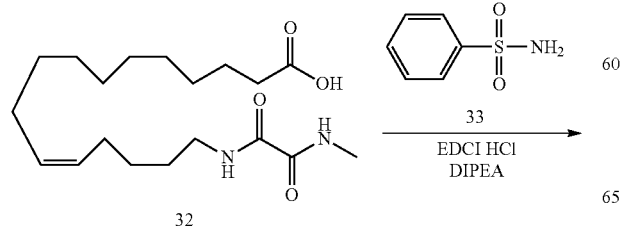

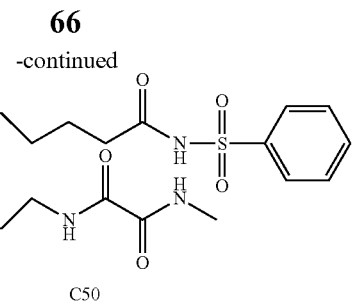

C50

16-(2-(methylamino)-2-oxoacetamido)hexadec-11(Z)-enoic acid 32 was prepared following literature precedent.[5] (Z)-16-(2-(methylamino)-2-oxoacetamido)hexadec-11-enoic acid 32 (30 mg, 0.091 mmol) and benzenesulfonamide 33 (13 mg, 0.091 mmol) were taken in a dried round bottom flask in 5 mL anhydrous DMF under an argon atmosphere. Dimethylaminopyridine (DMAP, 13 mg, 0.12, 1.2 equiv) and 1-ethyl-3-(3-dimethylaminopropyl)carbodiimide (16 mg, 0.12 mmol; EDCI. HCl) were added as a solid. After stirring for 12 h at room temperature, the reaction mixture was diluted with water (20 mL) and the combined aqueous layers were extracted with EtOAc (3×20 mL), organic layers were washed with water (2×10 mL) and brine (10 mL). The combined organic extracts were dried over Na$_2$SO$_4$, concentrated under reduced pressure, and the residue was purified by PTLC using 100% EtOAc as eluent to give amide (35 mg, 84%) as a white solid.

TLC: 100% EtOAc, Rf: 0.30. $^1$H NMR (CDCl$_3$, 500 MHz): δ 8.05 (d, J=7.5 Hz, 2H), 7.85 (bs, 1H, NH), 7.65 (bs, 1H, NH), 7.60 (t, J=7.5 Hz, 1H), 7.55 (t, J=7.5 Hz, 2H), 5.26-5.42 (m, 2H), 3.28_3.35 (m, 2H), 2.90 (s, 3H), 2.36 (t, 2H, J=7.3 Hz), 1.97-2.08 (m, 4H), 1.51-1.64 (m, 4H), 1.22-1.42 (m, 14H). mp: 72° C.-73° C.

Example 9

Preparation of Example Compound C44

Synthesis of (Z)—N$^1$-(15-((2-hydroxyphenyl)thio)pentadec-5-en-1-yl)-N$^2$-methyloxalamide C44

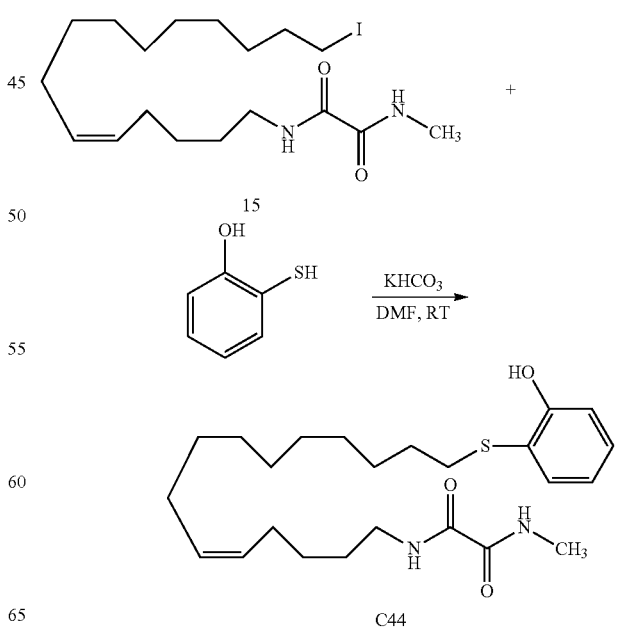

C44

To a suspension of (Z)—N$^1$-(15-iodopentadec-5-en-1-yl)-N$^2$-methyloxalamide (15) (400 mg, 0.92 mmol) and KHCO$_3$ (1.2 equiv, 1.10 mmol, 111 mg) in anhydrous DMF (3.5 mL) was added 2-mercaptophenol (1 equiv, 116 mg) dropwise. The reaction was stirred overnight at room temperature. Note: The reaction went from a white suspension to a clear solution by the next day. After the reaction was judged complete by TLC analysis, the reaction was quenched with water, extracted with ethyl acetate (3×30 mL), dried over anhydrous Na$_2$SO$_4$, filtered, and concentrated under vacuum. The crude product was purified using a Teledyne Isco Combiflash® RF chromatographic system (12 g SiO$_2$ column eluted with 15-20% EtOAc/hexane) to give the title phenol (317 mg, 79%) as a pale yellow solid.

TLC: 50% EtOAc/hexanes, R$_f$=0.65. $^1$H NMR (CDCl$_3$, 500 MHz) δ 7.46 (dd, J=7.5, 1.5 Hz, 2H), 7.45-7.39 (brs, 1H), 7.29-7.22 (m, 1H), 6.98 (dd, J=8.3, 1.3 Hz, 1H), 6.87 (td, J=7.5, 1.3 Hz, 1H), 6.78 (s, 1H), 5.42-5.26 (m, 2H), 3.31 (q, J=6.9 Hz, 2H), 2.91 (d, J=5.2 Hz, 3H), 2.72-2.65 (m, 2H), 2.10-1.91 (m, 5H), 1.62-1.49 (m, 5H), 1.44-1.23 (m, 12H); $^{13}$C NMR (125 MHz, CDCl$_3$) δ 160.69, 159.81, 156.99, 135.93, 130.95, 130.72, 128.96, 120.74, 119.37, 114.78, 39.68, 36.85, 29.77, 29.73, 29.52, 29.51, 29.34, 29.19, 28.91, 28.67, 27.32, 26.96, 26.79, 26.28. mp: 62.4-62.7° C.

REFERENCES

1. Meddad-Belhabich, N.; Aoun, D.; Djimdé, A.; Redeuilh, C.; Dive, G.; Massicot, F.; Chau, F.; Heymans, F.; Lamouri, A. Design of new potent and selective secretory phospholipase A$_2$ inhibitors. 6-Synthesis, structure-activity relationships and molecular modeling of 1-substituted-4-[4,5-dihydro-1,2,4-(4H)-oxadiazol-5-one-3-yl(methyl)]-functionalized aryl piperazin/one/dione derivatives. *Bioorg. Med. Chem.* 2010, 18, 3588-3600.
2. Borbas, K. E.; Ling Kee, H.; Holten, D.; Lindsey, S. J. A compact water-soluble porphyrin bearing an iodoacetamido bioconjugatable site. *Org. Biomol. Chem.,* 2008, 6, 187-194.
3. Ellingboe, J. W.; Lombardo, L. J.; Alessi, T. R.; Nguyen, T. T.; Guzzo, F.; Guinosso, C. J.; Bullington, J.; Browne, E. N. C.; Bagli, J. F. Antihyperglycemic activity of novel naphthalenylmethyl-3H-1,2,3,5-oxathiadiazole 2-oxides. *J. Med. Chem.* 1993, 36, 2485-2493.
4. Thiel, O. R.; Bernard, C.; King, T.; Dilmeghani-Seran, M.; Bostick, T.; Larsen, R. D.; Margaret M. Faul, M. M. *J. Org. Chem.* 2008, 73, 3508-3515.
5. Falck, J. R.; Wallukat, G.; Puli, N.; Gall, M.; Arnold, C.; Konkel, A.; Rothe, M.; Fischer, R.; Müller, D. N.; Schunck, W. H. 17(R),18(S)-epoxyeicosatetraenoic acid, a potent eicosapentaenoic acid (EPA) derived regulator of cardiomyocyte contraction: structure-activity relationships and stable analogues. *J. Med. Chem.* 2011, 54, 4109-4118.
6. Y. Hamada et al./*Bioorg. Med. Chem. Lett.* 18: 1649-1653, 2008.

Example 10

Determination of Biological Activities of Selected Example Compounds of the Present Invention Materials and Methods:

The structures of all compounds tested are given in FIG. 1. The compounds include analogues synthesized as described in Examples 2-9. EPA and 17,18-EEQ (purchased from Cayman Chemical) were used as controls. Before use the compounds to be tested were prepared as 1000-fold stock solutions in ethanol.

In order to measure the biological activities of the novel compounds an established cell model was used (Kang, J. X. and A. Leaf, *Effects of long-chain polyunsaturated fatty acids on the contraction of neonatal rat cardiac myocytes.* Proc Natl Acad Sci USA, 1994. 91(21): p. 9886-90.). The spontaneously beating neonatal rat cardiomyocytes (NRCMs) are a model system to investigate anti-arrhythmic effects of test-compounds. Irregular and asynchronous beating of the cells in response to arrhythmic substances serve as an in vitro equivalent to cardiac fibrillation in vivo, which can be reversed by synthetic 17,18-EEQ analogs/test compounds.

Isolation and cultivation of NRCMs were performed as described previously (Wallukat, G; Wollenberger, A. *Biomed Biochim Acta.* 1987;78:634-639; Wallukat G, Homuth V, Fischer T, Lindschau C, Horstkamp B, Jupner A, Baur E, Nissen E, Vetter K, Neichel D, Dudenhausen J W, Haller H, Luft F C. *J Clin Invest.* 1999; 103: 945-952). Briefly, neonatal Wistar rats (1-2 days old) were killed in conformity to the recommendations of the Community of Health Service of the City of Berlin and the cardiomyocytes were dissociated from the minced ventricles with a 0.2% solution of crude trypsin. The isolated cells were then cultured as monolayers on the bottom (12.5 cm$^2$) of Falcon flasks in 2.5 ml of Halle SM 20-I medium equilibrated with humidified air. The medium contained 10% heat-inactivated FCS and 2 µmol/l fluoro-deoxyuridine (Serva, Heidelberg, Germany), the latter to prevent proliferation of non-muscle cells. The NRCMs (2.4×10$^6$ cells/flask) were cultured at 37° C. in an incubator. After 5 to 7 days, the NRCMs formed spontaneously beating cell clusters. The cells in each cluster showed synchronized contraction with a beating rate of 120 to 140 beats per minute. On the day of the experiment, the culture medium was replaced by 2.0 ml fresh serum-containing medium. Two hours later, the beating rates were monitored at 37° C. using an inverted microscope equipped with a heating stage. To determine the basal rate, 6 to 8 individual clusters were selected and the number of contractions was counted for 15 sec. After that, the compound to be tested was added to the culture and the beating rate of the same clusters was monitored 5 min later again. Based on the difference between the basal and compound-induced beating rate of the individual clusters, the chronotropic effects (Δ beats/min) were calculated and are given as mean±SE values. N refers to the number of clusters monitored which originated, in general, from at least three independent NRCM cultures.

Results:

The results of these experiments are presented in FIG. 1. All compounds tested were added to the NRCMs at a final concentration of 30 nM and the measurement was performed after 5 min of incubation; except EPA that was used at a final concentration of 3.3 µM and the effect was monitored after 30 min of incubation. Under the same conditions, the vehicle control (0.1% ethanol) showed no effect on the spontaneous beating rate.

As summarized in FIG. 1, synthetic analogues tested showed a negative chronotropic effect similar to that of EPA and 17,18-EEQ. Therefore, the carboxy group can be replaced with different carboxylic acid bioisoters (C38, C41, C42, C43, C44, C49, C50, C52) without a change in the negative chronotropic effect of these synthetic analogs.

Since C44 showed the lowest activity (−7.5±4.5; n=12) it seems to harbor the least effective carboxylic acid bioisostere.

C38, C41, C42, C43, C44, C50 and C52 provide examples for compounds according to the general formula (IV) in claim-1. The location of the double bond in these compounds is in agreement with previous structure-activity relationship studies showing that the 11,12-double bond is essential for the biological activity of 17,18-EEQ and its agonists (Falck J R, Wallukat G, Puli N, Goli M, Arnold C, Konkel A, Rothe M, Fischer R, Müller D N, Schunck W H. 17(R),18(S)-epoxyeicosatetraenoic acid, a potent eicosapentaenoic acid (EPA) derived regulator of cardiomyocyte contraction: structure-activity relationships and stable analogues. J Med Chem. 2011 Jun. 23; 54(12):4109-18). C48 and C49 contain aromatic ring structure in those part of the molecule that otherwise harbors the 11,12-double bond. The negative chronotropic effects of C48 and C49 demonstrate that also compounds according to the general formula (III) in claim-1 are bioactive.

The invention claimed is:
1. A compound of the general formula (IV):

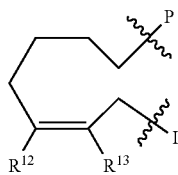

or a pharmaceutically acceptable salt thereof,
wherein P is a group represented by the general formula (II):

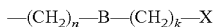

wherein X represents:

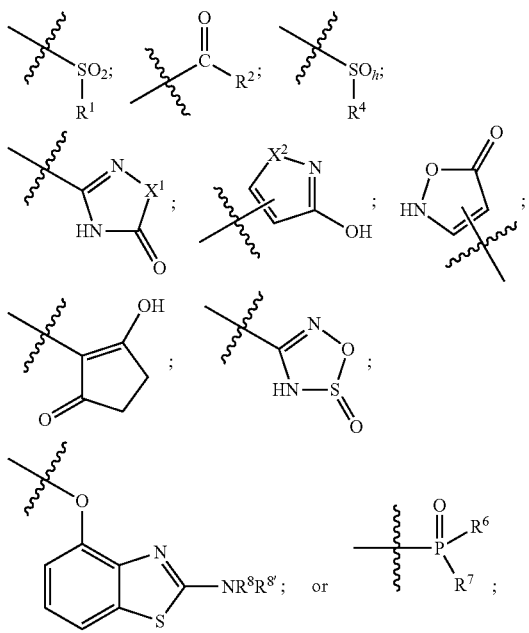

wherein k is 0 or 1; and
B represents a bond, —O—, or —S—;
n is 0 or an integer of from 3 to 8; and
k is 0 or 1, provided that when n is 0 or 3, then k is 1 and when n is 3, B is —O— or —S—;
wherein
 $R^1$ represents a hydroxyl group, $C_1$-$C_6$alkoxy, —NHCN, —NH($C_1$-$C_6$alkyl), —NH($C_3$-$C_6$cycloalkyl), —NH(aryl), or —O($C_1$-$C_6$alkyldiyl)O(C=O)$R^{11}$;
 $R^{11}$ is a $C_1$-$C_6$alkyl group which is optionally substituted with one or more fluorine or chlorine atom(s), or with a $C_3$-$C_6$cycloalkyl group which is optionally substituted with one or more fluorine or chlorine atom(s) or hydroxyl group(s);
 $R^2$ represents —NHR$^3$, —NR$^{20}$R$^{21}$, —OR$^{22}$, or —(OCH$_2$—CH$_2$)$_i$—R$^{23}$;
wherein
 $R^3$ represents (SO$_2$R$^{30}$), (OR$^{31}$), —$C_1$$C_6$alkanediyl(SO$_2$R$^{32}$), or —$C_1$-$C_6$alkanediyl(CO$_2$H);
 $R^{30}$ is a $C_1$-$C_6$alkyl group which is optionally substituted with —NH$_2$, —NH($C_1$-$C_6$)alkyl, —N($C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, one, two or three fluorine or chlorine atoms, or a hydroxyl group,
 or an aryl group which is optionally substituted with one, two or three substituents independently selected from the group consisting of $C_1$-$C_6$alkyl, $C_1$-$C_6$alkoxy, $C_1$-$C_6$alkylthio, fluorine or chlorine atom, hydroxyl group, amino group, —NH($C_1$-$C_6$alkyl), and —N($C_1$-$C_6$)dialkyl;
 $R^{31}$ is a $C_1$-$C_6$alkyl group which is optionally substituted with one or more fluorine or chlorine atom(s) or hydroxyl group(s);
 or a $C_3$-$C_6$cycloalkyl group which is optionally substituted with one or more fluorine or chlorine atom(s) or hydroxyl group(s);
 $R^{32}$ is a $C_1$-$C_6$alkyl group which is optionally substituted with one or more fluorine or chlorine atom(s) or hydroxyl group(s),
 or a $C_3$-$C_6$cycloalkyl group which is optionally substituted with one or more fluorine or chlorine atom(s) or hydroxyl group(s);
 $R^{20}$ and $R^{21}$ each independently represents a hydrogen atom, a $C_1$-$C_6$alkyl group which is optionally substituted with one or more fluorine or chlorine atom(s) or hydroxyl group(s), a $C_3$-$C_6$cycloalkyl group which is optionally substituted with one or more fluorine or chlorine atom(s) or hydroxyl group(s) or —$C_1$-$C_6$alkyldiyl(CO$_2$H);
 $R^{22}$ is a hydrogen atom, a $C_1$-$C_6$alkyl group or a $C_3$-$C_6$cycloalkyl group, wherein the $C_1$-$C_6$alkyl group or the $C_3$-$C_6$cycloalkyl group is optionally substituted with —NH$_2$, —NH($C_1$-$C_6$)alkyl, —N($C_1$-$C_6$)dialkyl, —NH($C_1$-$C_6$)alkyldiyl, —$C_1$-$C_6$alkoxy, one, two or three fluorine or chlorine atom(s), hydroxy, or $C_1$-$C_6$alkoxy;
 $R^{23}$ is —OH, —O($C_1$-$C_3$)alkyl, or —N($C_1$-$C_3$)dialkyl;
 i is an integer of from 1 to 10;
 $R^4$ represents

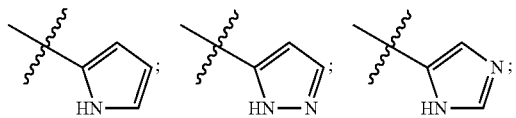

-continued

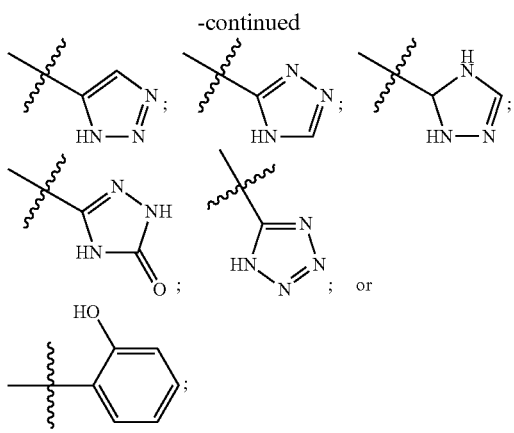

h is 0, 1, or 2;
R⁶ and R⁷ each independently represent a hydroxyl group, an —O(C₁-C₆)alkyl group, an —O(C₂-C₆)alkenyl group, a —O(C₁-C₆)alkyldiylO(C=O)(C₁-C₆)alkyl group or a —(C₁-C₆)alkyldiylO(C=O)(C₂-C₆)alkenyl group, wherein the C₁-C₆alkyl group and the C₂-C₆alkenyl group are optionally substituted with NH₂, —NH(C₁-C₆)alkyl, —N(C₁-C₆)dialkyl, C₁-C₅alkylcarbonyloxy-, C₁-C₆alkoxycarbonyloxy-, C₁-C₆alkylcarbonylthio-, C₁-C₆alkylaminocarbonyl-, di(C₁-C₆)alkylaminocarbonyl-; or with one, two or three fluorine or chlorine atom(s);
R⁸ and R⁸' each independently represents a hydrogen atom, a C₁-C₆alkyl group, —C(=O)C₁-C₆alkyl, —C(=O)C₃-C₆cycloalkyl, —C(=O)aryl; or —C(=O)heteroaryl, wherein the C₁-C₆alkyl, the C₃-C₆cycloalkyl, the aryl, or the heteroaryl group may be substituted with one, two or three substituents selected from the group consisting of fluorine atom, chlorine atom, hydroxy, —NH₂, —NH(C₁-C₆)alkyl, -N(C₁-C₆)dialkyl, —NH(C₁-C₆)alkanediyl-C₁-C₆alkoxy, and C₁-C₆alkoxy;
X¹ represents an oxygen atom; sulfur atom; or NH;
X² represents an oxygen atom; sulfur atom; NH; or N(CH₃);
wherein
R¹² and R¹³ of formula (IV) each independently is
a hydrogen atom, a fluorine atom, hydroxy, —NH₂, C₁-C₆alkyl, C₁-C₆alkoxy, —C(=O)-aryl, —C(=O) C₁-C₆alkyl, —SO₂(C₁-C₆alkyl) or —SO₂aryl,
wherein any of the foregoing C₁-C₆alkyl, C₁-C₆alkoxy, —(=O)-aryl, or —SO₂aryl are optionally substituted with one, two or three substituents independently selected from the group consisting of:
—NH₂, —NH(C₁-C₆)alkyl, —N(C₁-C₆)dialkyl, C₁-C₆alkylcarbonyloxy-, C₁-C₆alkoxycarbonyloxy-, C₁-C₆ alkylcarbonylthio-, C₁-C₆alkylaminocarbonyl-, di(C₁-C₆)alkylaminocarbonyl-, fluorine atom, chlorine atom, and hydroxy;
or R¹² and R¹³ form together a 5-membered or 6-membered ring, which is optionally substituted with one, two or three substituents independently selected from the group consisting of:
—NH₂, —NH(C₁-C₆)alkyl, —N(C₁-C₆)dialkyl, C₁-C₆alkylcarbonyloxy-, C₁-C₆ ₆alkoxycarbonyloxy-, C₁-C₆alkylcarbonylthio-, C₁-C₆alkylaminocarbonyl-, di(C₁-C₆)alkylaminocarbonyl-, fluorine atom, chlorine atom, and hydroxy;
I is —(CH₂)₃—Y, wherein
Y represents a group:

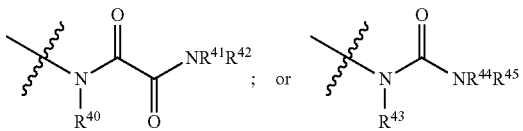

wherein
R⁴⁰, R⁴¹, R⁴³, and R⁴⁴ each represents a hydrogen atom;
R⁴² is a methyl group and R⁴⁵ is an ethyl group;
with the proviso that
when:
(i) n is 3 and each of R¹² and R¹³ is a hydrogen atom;
(ii) n is 4 and k is 1 and each of R¹² and R¹³ is a hydrogen atom;
or
(iii) n is 5, 6, 7, or 8, and each of R¹² and R¹³ is a hydrogen atom then, P represents one of the following groups:
—(CH₂)₃—O—(CH₂)—X⁸¹, —(CH₂)₃—S—(CH₂)—X⁸¹, —(CH₂)₅—O—(CH₂)—X⁸¹, —(CH₂)₅—S—(CH₂)—X⁸¹, —(CH₂)₅—O—X⁸², —(CH₂)₅—X⁸³; —(CH₂)₇—O—X⁸²; or —(CH₂)₇—X⁸³, wherein
X⁸¹ represents a group:

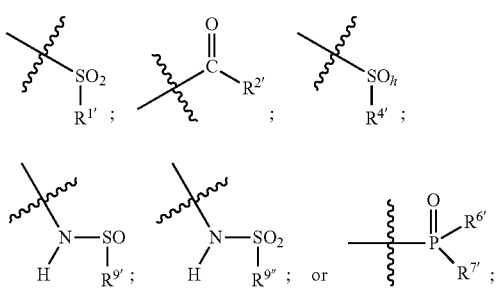

X⁸² represents a group:

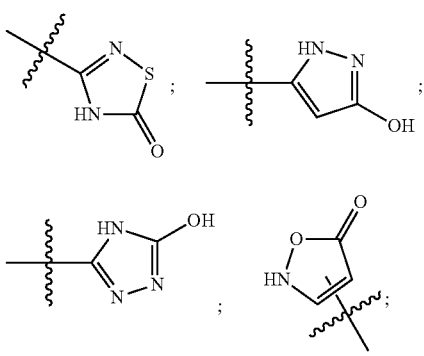

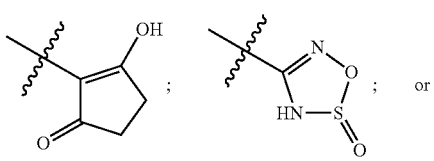

; or

-continued

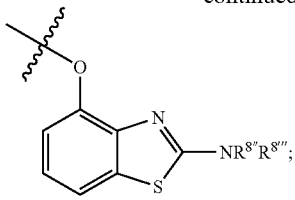

X⁸³ represents a group:

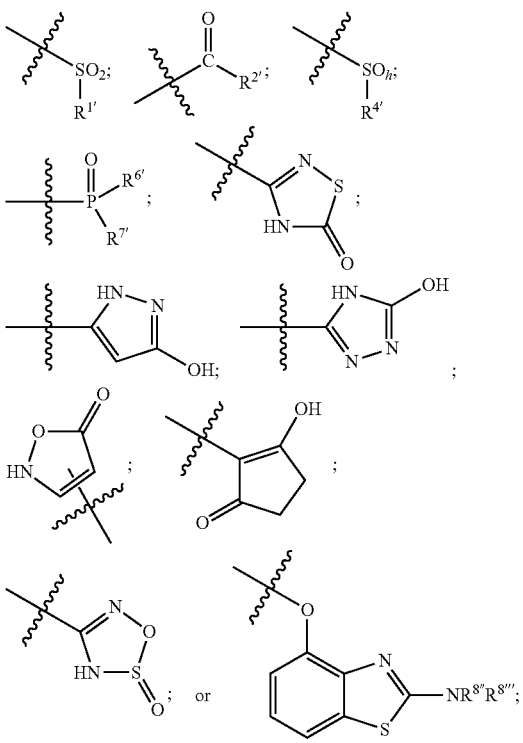

R¹' is defined as R¹ above;
R²' represents —NHR³', —OR²²', —(OCH₂—CH₂)ᵢ—R²³,
wherein
R³' represents (SO₂R³⁰), (OR³¹), —C₁-C₆alkanediyl(SO₂R³²), or —C₂-C₆alkanediyl(CO₂H),
R²²' is a C₃-C₆cycloalkyl group, which is optionally substituted with —NH₂, —NH(C₁-C₆)alkyl, —N(C₁-C₆)dialkyl, —NH(C₁-C₆)alkyldiyl-C₁-C₆alkoxy, one, two or three fluorine or chlorine atom(s), hydroxy, or C₁-C₆alkoxy,
R²³ and i are as defined above, provided that when i=3, R²³ is not —OH;
R⁴' is defined as R⁴ above; and h is defined as above;
R⁶' and R⁷' are defined as R⁶ and R⁷ above;
R⁸'' and R⁸''' are defined as R⁸ and R⁸' above;
R⁹' is defined as R⁹ above; R⁹'' represents aryl which is optionally substituted with one, two or three substituents independently selected from the group consisting of C₁-C₆alkyl, C₁-C₆alkoxy, C₁-C₆alkylthio, fluorine or chlorine atom, hydroxyl group, amino group, —NH(C₁-C₆alkyl), —N(C₁-C₆)dialkyl, and an oxo substituent.

2. The compound according to any one of claim 1, wherein X is

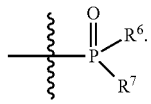

3. The compound according to claim 1, wherein one of R¹² and R¹³ represents a hydrogen atom and the other represents a fluorine atom, hydroxy, —NH₂, C₁-C₆alkyl, C₁-C₆alkoxy, —C(=O)-aryl, —C(=O)C₁-C₆alkyl, or —SO₂(C₁-C₆alkyl); or —SO₂aryl; wherein any of the foregoing C₁-C₆alkyl, C₁-C₆alkoxy, or aryl are optionally substituted with one, two or three substituents independently selected from the group consisting of —NH₂, —NH(C₁-C₆)alkyl, —N(C₁-C₆)dialkyl, C₁-C₆alkylcarbonyloxy-, C₁-C₆ alkoxycarbonyloxy-, C₁-C₆alkylcarbonylthio-, C₁-C₆alkylaminocarbonyl-, di(C₁-C₆)alkylaminocarbonyl-, fluorine or chlorine atom, and hydroxy; or R¹² and R¹³ are taken together to form a 5-membered or 6-membered ring, which ring is optionally substituted with one, two or three substituents independently selected from the group consisting of —NH₂, —NH(C₁-C₆)alkyl, —N(C₁-C₆)dialkyl, C₁-C₆ alkylcarbonyloxy-, C₁-C₆alkoxycarbonyloxy-, C₁-C₆ alkylcarbonylthio-, C₁-C₆alkylaminocarbonyl-, di(C₁-C₆)alkylaminocarbonyl-, fluorine or chlorine atom, and hydroxy.

4. The compound according to claim 1, wherein P is —(CH₂)₃—O—(CH₂)—X⁸¹; —(CH₂)₅—O—(CH₂)—X⁸¹; —(CH₂)₃—S—(CH₂)—X⁸¹; —(CH₂)₅—S—(CH₂)—X⁸¹; —(CH₂)₅—O—X⁸²; —(CH₂)₇—O—X⁸²; —(CH₂)₅—X⁸³ or —(CH₂)₇—X⁸³.

5. (Withdrawn- Currently Amended) The compound according to claim 4, wherein P represents —(CH₂)₅—X⁸³ or —(CH₂)₇—X⁸³.

6. The compound according to claim 1, wherein X⁸³ represents a group selected from the groups consisting of:

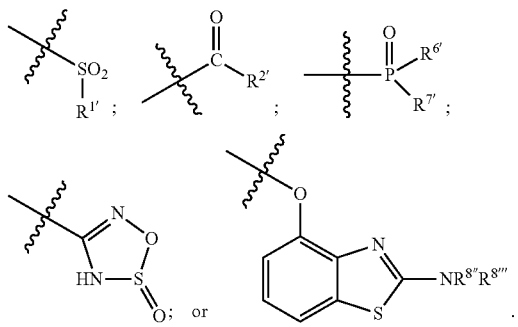

7. The compound according to claim 1, wherein n is 3 and R¹' is a hydroxyl group; and R²' represents —NHR³'
wherein
R³' is (SO₂R³⁰), R³⁰ is —C₁-C₆alkyl or phenyl;
R⁶' and R⁷' each independently represents a hydroxyl group; an —O(C₁-C₆)alkyl group; or an —O(CH₂)O(C=O)(C₁-C₆)alkyl group;
R⁸''' is hydrogen atom; and R⁸'''' is —C(=O)C₁-C₆alkyl.

8. A compound selected from the group consisting of:

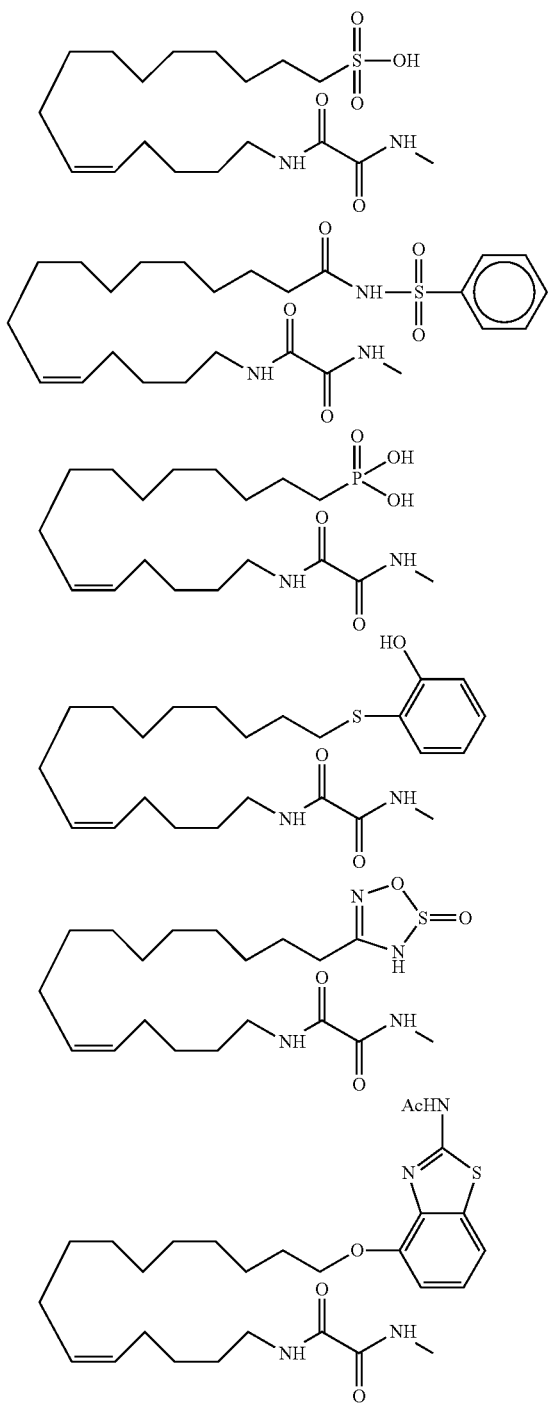

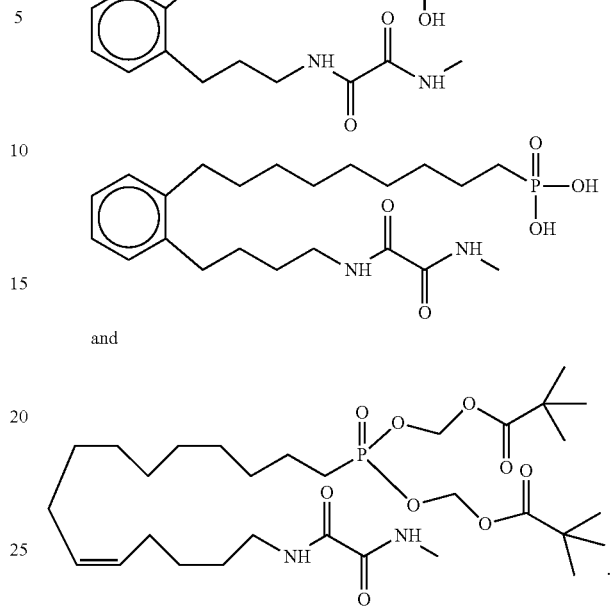

and

9. A pharmaceutical composition that comprises at least one compound according to claim 1, and, optionally, a carrier substance and/or an adjuvant.

10. The compound according to claim 1, wherein said compound is part of a medicament.

11. A method comprising:
administering to a patient that suffers from a cardiovascular disease or has suffered in the past from a cardiovascular disease an effective amount of at least one of the compounds of claim 1.

12. The method of claim 11, wherein the cardiovascular disease is ventricular arrhythmia or atrial fibrillation.

13. The method of claim 12, wherein at least 0.5 mg of the at least one compound is administered to the patient in one day.

14. A method for providing omega-3 (n-3) polyunsaturated fatty acids (PUFA) derivatives to a persons at risk to develop a condition or disease associated with inflammation, proliferation, hypertension, coagulation, immune function, pathologic angiogenesis, or cardiac disease comprising:
providing orally or parenterally to the person at risk at least one of the compounds of claim 1 in an amount considered effective to reduce the risk of developing said condition or disease.

* * * * *